(12) United States Patent
Bardroff et al.

(10) Patent No.: US 11,987,644 B2
(45) Date of Patent: May 21, 2024

(54) METHOD OF MANUFACTURING BISPECIFIC ANTIBODIES, BISPECIFIC ANTIBODIES AND THERAPEUTIC USE OF SUCH ANTIBODIES

(71) Applicant: NOVARTIS AG, Basel (CH)

(72) Inventors: Michael Otto Bardroff, Loerrach (DE); Tina Buch, Efringen-Kirchen (DE); Christian Graf, Munich (DE); Daniel Heitmann, Zürich (CH); Thomas Jostock, Neuenburg am Rhein (DE); Hans-Peter Knopf, Schallstadt (DE); Rolf Koehler, Basel (CH); Jiri Kovarik, Zürich (CH); Stephen John Oliver, Basel (CH); Dhavalkumar Patel, Basel (CH); Maximilian Woisetschlaeger, Oberwil (CH)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 16/844,999

(22) Filed: Apr. 9, 2020

(65) Prior Publication Data

US 2020/0308309 A1 Oct. 1, 2020

Related U.S. Application Data

(63) Continuation of application No. 16/005,088, filed on Jun. 11, 2018, now abandoned.

(60) Provisional application No. 62/518,090, filed on Jun. 12, 2017.

(51) Int. Cl.

| | |
|---|---|
| *C07K 16/00* | (2006.01) |
| *A61P 1/00* | (2006.01) |
| *A61P 9/00* | (2006.01) |
| *A61P 9/10* | (2006.01) |
| *A61P 9/14* | (2006.01) |
| *C07K 16/24* | (2006.01) |
| *C07K 16/28* | (2006.01) |
| *C07K 16/46* | (2006.01) |

(52) U.S. Cl.
CPC ............ *C07K 16/468* (2013.01); *A61P 1/00* (2018.01); *A61P 9/10* (2018.01); *A61P 9/14* (2018.01); *C07K 16/00* (2013.01); *C07K 16/244* (2013.01); *C07K 16/245* (2013.01); *C07K 16/2863* (2013.01); *C07K 16/2887* (2013.01); *C07K 16/46* (2013.01); *C07K 2317/24* (2013.01); *C07K 2317/31* (2013.01); *C07K 2317/51* (2013.01); *C07K 2317/515* (2013.01); *C07K 2317/526* (2013.01); *C07K 2317/53* (2013.01); *C07K 2319/00* (2013.01)

(58) Field of Classification Search
CPC .... C07K 16/468; C07K 16/244; C07K 16/46; C07K 2317/31; C07K 2317/53; C07K 2319/00

See application file for complete search history.

(56) References Cited

U.S. PATENT DOCUMENTS

| | | | |
|---|---|---|---|
| 7,993,878 B2 | 8/2011 | Gram et al. | |
| 9,212,230 B2 | 12/2015 | Schuurman et al. | |
| 9,376,489 B2 | 6/2016 | Bardroff et al. | |
| 9,527,927 B2 | 12/2016 | Chowdhury et al. | |
| 10,882,922 B2 | 1/2021 | Yang | |
| 2003/0148463 A1 | 8/2003 | Kufer et al. | |
| 2009/0081191 A1 | 3/2009 | Kufer et al. | |
| 2010/0047204 A1* | 2/2010 | Yoo | A61P 3/10 424/85.2 |
| 2014/0010814 A1 | 1/2014 | Benhar et al. | |
| 2014/0112915 A1* | 4/2014 | Bardroff | C12P 21/005 424/133.1 |
| 2014/0242080 A1 | 8/2014 | Jaeger et al. | |
| 2014/0377253 A1* | 12/2014 | Harding | A61P 29/00 424/133.1 |
| 2015/0232673 A1 | 8/2015 | Jing et al. | |
| 2017/0002060 A1* | 1/2017 | Bolen | C07K 16/00 |
| 2017/0320967 A1* | 11/2017 | Yang | A61K 45/06 |
| 2019/0218311 A1* | 7/2019 | Loew | C07K 16/40 |

FOREIGN PATENT DOCUMENTS

| | | | |
|---|---|---|---|
| AU | 2018284303 B2 | 4/2021 | |
| RU | 2587616 C2 | 12/2019 | |
| WO | 1996027011 A1 | 9/1996 | |
| WO | 02/16436 A2 | 2/2002 | |
| WO | 2002/16436 A2 | 2/2002 | |
| WO | 2007050607 A2 | 5/2007 | |
| WO | 2008145664 A1 | 12/2008 | |
| WO | WO 09/149185 A2 | 12/2009 | |
| WO | 2010006060 A2 | 1/2010 | |
| WO | 2010097240 A1 | 9/2010 | |
| WO | WO 2011/116387 * | 9/2011 | ............ A61K 39/00 |
| WO | 2012/023053 A2 | 2/2012 | |
| WO | 2012135345 A1 | 10/2012 | |
| WO | 2013/096291 A2 | 6/2013 | |

(Continued)

OTHER PUBLICATIONS

Paul, Fundamental Immunology, 3rd Edition, 1993, pp. 292-295.*
MacCallum et al., J. Mol. Biol., 262, 732-745, 1996.*
Pascalis et al., Journal of Immunology, 2002, vol. 169, pp. 3076-3084.*
Casset et al., Biochemical and Biophysical Research Communications, 2003, vol. 307, pp. 198-205.*
Vajdos et al., Journal of Molecular Biology, 2002, vol. 320, pp. 415-428.*
Christian Klein et al. "Progress in overcoming the chain association issue in bispecific heterodimeric IgG antibodies" Landes Bioscience, mAbs, (2012), vol. 4, No. 6, pp. 653-663.

(Continued)

*Primary Examiner* — Mark Halvorson
(74) *Attorney, Agent, or Firm* — David Goetz

(57) ABSTRACT

The invention relates to bivalent bispecific monoclonal antibodies (bbmAb) or variants thereof, and methods of manufacturing such antibodies by co-expressing modified Fc-mutated derivatives of two different monoclonal antibodies in mammalian cell lines.

4 Claims, 17 Drawing Sheets

Specification includes a Sequence Listing.

(56) References Cited

FOREIGN PATENT DOCUMENTS

| WO | 2014/037899 A2 | 3/2014 |
|---|---|---|
| WO | 2015/198240 A2 | 12/2015 |
| WO | 2016/026943 A1 | 2/2016 |
| WO | 2017/011773 A2 | 1/2017 |
| WO | 2017/059551 A1 | 4/2017 |
| WO | 2018/057955 A1 | 3/2018 |

OTHER PUBLICATIONS

Roland E. Kontermann et al. "Bispecific Antibodies" Drug Discovery Today, (2015), vol. 20, No. 7, pp. 838-847.
A. Margaret Merchant, et al. "An efficient route to human bispecific IgG" Nature Publishing Group, Nature BioTechnology, (1998), vol. 16, pp. 677-681.
John B.B. Ridgway, et al. "'Knobs-into-holes' engineering of antibody CH3 domains for heavy chain heterodimerization" Protein Engineering, (1996), vol. 9, No. 7, pp. 617-621.
Brinkmann et al., The Making of Bispecific Antibodies, MABS, 9(2):182-212 (2017).
Fischer et al., Exploiting light chains for the scalable generation and platform purification of native human bispecific IgG, Nature Communications, Nature Publishing Group, vol. 6 (2015).
Magistrelli et al., Optimizing assembly and production of native bispecific antibodies by codon de-optimization, MABS, 9(2):231-239 (2016).
Klein, Christian et al., "Progress in Overcoming the Chain Association Issue in Bispecific Heterodimeric IgG Antibodies," Landes Bioscience, mAbs, 2012, vol. 4, No. 6; pp. 653-663.
Kontermann et al., Roland E., "Bispecific Antibodies," Drug Discovery Today, 2015, vol. 20, No. 7, pp. 838-847.
Merchant, A. Margaret et al., "An Efficient Route to Human Bispecific IgG," Nature Publishing Group, Nature Bio Technology, 1998, vol. 16, pp. 677-681.
Ridgway, John B. et al., "Knobs-into-holes Engineering of Antibody CH3 Domains for Heavy Chain Heterodimerization," Protein Engineering, 1996, vol. 9, No. 7, pp. 617-621.
Brinkman et al., "The Making of Bispecific Antibodies," MABS, 2017, vol. 9, No. 2, pp. 182-212.
Fisher et al., "Exploiting Light Chains for the Scalable Generation and Platform Purification of Native Human Bispecific IgG," Nature Communications, Nature Publishing Group, 2015, vol. 6.
Magistrelli, et al., Optimizing Assembly and Production of Native Bispecific Antibodies by Codon De-Optimization, MABS, 2016, vol. 9, No. 2, pp. 231-239.
Liu et al., "Recovery and Purification Process Development for Monoclonal Antibody Production," mAbs, 2010, vol. 2, No. 5, pp. 480-499.
Chowdhur et al., "Insights Into the Molecular Basis of a Bispecific Antibody's Target Selectivity," MAbs, 2015, vol. 7, pp. 461-669, PMID:25730144, http:11dx.doi.orel10.1080119420862.
Labrijn, et al., Bispecific antibodies: a mechanistic review of the pipeline, Nature Reviews, Aug. 2019, 585-608, 18.

* cited by examiner

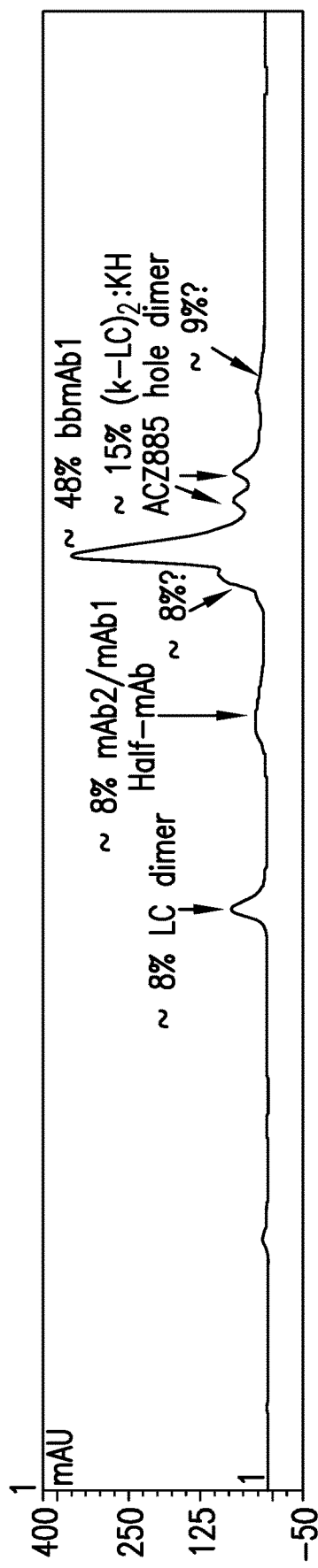
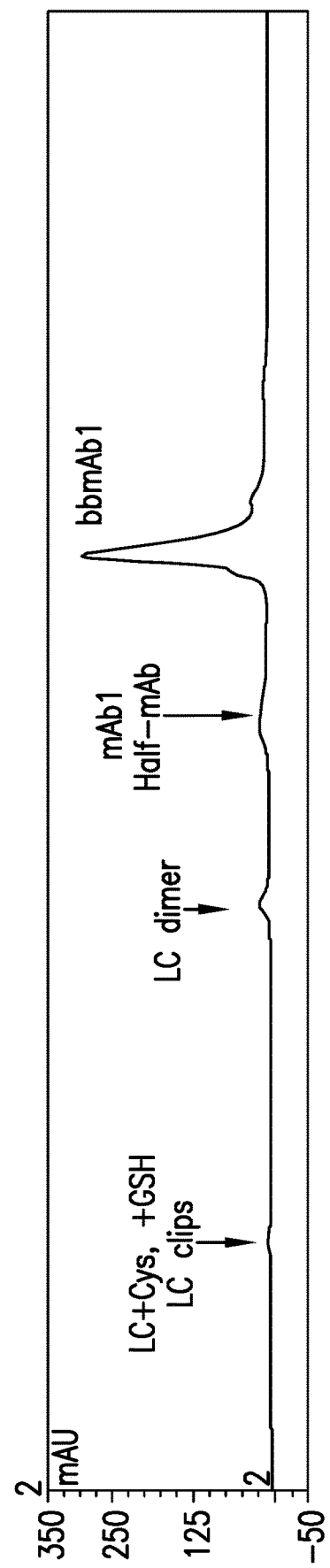
FIG.3A
FIG.3B

SEQUENCE LISTING

<160> NUMBER OF SEQ ID NOS: 104

<210> SEQ ID NO 1
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Ser Tyr Ala Ile Ser
1               5

<210> SEQ ID NO 2
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Asn Ile Ile Pro Met Thr Gly Gln Thr Tyr Tyr Ala Gln Lys Phe Gln
1               5                   10                  15

Gly

<210> SEQ ID NO 3
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

```
Ala Ala Tyr His Pro Leu Val Phe Asp Asn
1               5                   10
```

<210> SEQ ID NO 4
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

```
Gly Gly Thr Phe Lys Ser Tyr
1               5
```

<210> SEQ ID NO 5
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

```
Ile Pro Met Thr Gly Gln
1               5
```

<210> SEQ ID NO 6
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

```
Ala Ala Tyr His Pro Leu Val Phe Asp Asn
1               5                   10
```

<210> SEQ ID NO 7
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

```
Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Lys Ser Tyr
            20                  25                  30

Ala Ile Ser Trp Val Arg Gln Ala Pro Gly Gln Gly Leu Glu Trp Met
        35                  40                  45

Gly Asn Ile Ile Pro Met Thr Gly Gln Thr Tyr Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Ala Tyr His Pro Leu Val Phe Asp Asn Trp Gly Gln Gly
```

Thr Leu Val Thr Val Ser Ser
            115

<210> SEQ ID NO 8
<211> LENGTH: 356
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 8
gaggtgcagc tggtgcagag cggcgccgag gtgaagaagc ccggcagcag cgtgaaggtg      60
agctgcaagg ccagcggcgg caccttcaag agctacgcca tcagctgggt gaggcaggcc     120
cccggccagg gcctggagtg gatgggcaac atcatcccca tgaccggcca gacctactac     180
gcccagaagt tccagggcag ggtgaccatc accgccgacg agagcaccag caccgcctac     240
atggagctga gcagcctgag gagcgaggac accgccgtgt actactgcgc cagggccgcc     300
taccaccccc tggtgttcga caactgggcc agggcaccct ggtgaccgtg agcagc         356

<210> SEQ ID NO 9
<211> LENGTH: 449
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Lys Ser Tyr
            20                  25                  30

Ala Ile Ser Trp Val Arg Gln Ala Pro Gly Gln Gly Leu Glu Trp Met
        35                  40                  45

Gly Asn Ile Ile Pro Met Thr Gly Gln Thr Tyr Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Ala Tyr His Pro Leu Val Phe Asp Asn Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 10
<211> LENGTH: 1347
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 10
gaggtgcagc tggtgcagag cggcgccgag gtgaagaagc ccggcagcag cgtgaaggtg    60
agctgcaagg ccagcggcgg caccttcaag agctacgcca tcagctgggt gaggcaggcc   120
cccggccagg gcctggagtg gatgggcaac atcatcccca tgaccggcca gacctactac   180
gcccagaagt tccagggcag ggtgaccatc accgccgacg agagcaccag caccgcctac   240
atggagctga gcagcctgag gagcgaggac accgccgtgt actactgcgc cagggccgcc   300
taccaccccc tggtgttcga caactggggc cagggcaccc tggtgaccgt gagcagcgcc   360
agcaccaagg gccccagcgt gttccccctg cccccagca gcaagagcac cagcggcggc   420
accgccgccc tgggctgcct ggtgaaggac tacttcccccg agcccgtgac cgtgagctgg   480
aacagcggcg ccctgaccag cggcgtgcac accttccccg ccgtgctgca gagcagcggc   540
ctgtacagcc tgagcagcgt ggtgaccgtg cccagcagca gcctgggcac ccagacctac   600

-continued

```
atctgcaacg tgaaccacaa gcccagcaac accaaggtgg acaagagggt ggagcccaag    660
agctgcgaca agacccacac ctgccccccc tgccccgccc ccgaggccgc cggcggcccc    720
agcgtgttcc tgttcccccc caagcccaag acaccctga tgatcagcag gaccccgag     780 gtgacctgcg tggtggtgga cgtgagccac gaggaccccg aggtgaagtt caactggtac    840
gtggacggcg tggaggtgca caacgccaag accaagccca gggaggagca gtacaacagc    900
acctacaggg tggtgagcgt gctgaccgtg ctgcaccagg actggctgaa cggcaaggag    960
tacaagtgca aggtgagcaa caaggccctg cccgccccca tcgagaagac catcagcaag    1020
gccaagggcc agcccaggga gccccaggtg tacaccctgc cccccagcag ggaggagatg    1080
accaagaacc aggtgagcct gacctgcctg gtgaagggct tctacccag cgacatcgcc    1140 gtggagtggg agagcaacgg ccagcccgag aacaactaca agaccacccc ccccgtgctg    1200
gacagcgacg gcagcttctt cctgtacagc aagctgaccg tggacaagag caggtggcag    1260
cagggcaacg tgttcagctg cagcgtgatg cacgaggccc tgcacaacca ctacacccag    1320
aagagcctga gcctgagccc cggcaag                                        1347
```

<210> SEQ ID NO 11
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 11

Ser Gly Ser Ser Ser Asn Ile Gly Asn His Tyr Val Asn
1               5                   10

<210> SEQ ID NO 12
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 12

Arg Asn Asn His Arg Pro Ser
1               5

<210> SEQ ID NO 13
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 13

Gln Ser Trp Asp Tyr Ser Gly Phe Ser Thr Val
1               5                   10

<210> SEQ ID NO 14
<211> LENGTH: 9
<212> TYPE: PRT
<213> ORGANISM: Artificial Sequence
<220> FEATURE:
<221> NAME/KEY: source

```
<223> OTHER INFORMATION: /note="Description of Artificial Sequence:
      Synthetic peptide"

<400> SEQUENCE: 14

Ser Ser Ser Asn Ile Gly Asn His Tyr
1               5

<210> SEQ ID NO 15
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Arg Asn Asn
1

<210> SEQ ID NO 16
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Trp Asp Tyr Ser Gly Phe Ser Thr
1               5

<210> SEQ ID NO 17
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Asp Ile Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Asn His
            20                  25                  30

Tyr Val Asn Trp Tyr Gln Gln Leu Pro Gly Thr Ala Pro Lys Leu Leu
        35                  40                  45

Ile Tyr Arg Asn Asn His Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Gln Ser Trp Asp Tyr Ser Gly
                85                  90                  95

Phe Ser Thr Val Phe Gly Gly Gly Thr Lys Leu Thr Val Leu
            100                 105                 110

<210> SEQ ID NO 18
<211> LENGTH: 330
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic polynucleotide"

<400> SEQUENCE: 18

```
gatatcgtcc tgactcagcc ccctagcgtc agcggcgctc ccggtcagag agtgactatt    60
agctgtagcg gctctagctc taatatcggt aatcactacg tgaactggta tcagcagctg   120
cccggcaccg cccctaagct gctgatctat agaaacaatc accggcctag cggcgtgccc   180
gataggttta gcggatctaa gtcaggcact agcgctagtc tggctatcac cggactgcag   240
tcagaggacg aggccgacta ctactgtcag tcctgggact atagcggctt tagcaccgtg   300
ttcggcggag gcactaagct gaccgtgctg                                     330
```

<210> SEQ ID NO 19
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 19

Asp Ile Val Leu Thr Gln Pro Pro Ser Val Ser Gly Ala Pro Gly Gln
1               5                   10                  15

Arg Val Thr Ile Ser Cys Ser Gly Ser Ser Asn Ile Gly Asn His
            20                  25                  30

Tyr Val Asn Trp Tyr Gln Gln Leu Pro Gly Thr Ala Pro Lys Leu Leu
        35                  40                  45

Ile Tyr Arg Asn Asn His Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Gln Ser Trp Asp Tyr Ser Gly
                85                  90                  95

Phe Ser Thr Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 20
<211> LENGTH: 648
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

-continued

<400> SEQUENCE: 20

```
gatatcgtcc tgactcagcc ccctagcgtc agcggcgctc ccggtcagag agtgactatt      60
agctgtagcg gctctagctc taatatcggt aatcactacg tgaactggta tcagcagctg     120
cccggcaccg cccctaagct gctgatctat agaaacaatc accggcctag cggcgtgccc     180
gataggttta gcggatctaa gtcaggcact agcgctagtc tggctatcac cggactgcag     240
tcagaggacg aggccgacta ctactgtcag tcctgggact atagcggctt tagcaccgtg     300
ttcggcggag gcactaagct gaccgtgctg ggtcagccta aggctgcccc cagcgtgacc     360
ctgttccccc ccagcagcga ggagctgcag gccaacaagg ccaccctggt gtgcctgatc     420
agcgacttct acccaggcgc cgtgaccgtg gcctggaagg ccgacagcag ccccgtgaag     480
gccggcgtgg agaccaccac ccccagcaag cagagcaaca caagtacgc cgccagcagc      540
tacctgagcc tgaccccga gcagtggaag agccacaggt cctacagctg ccaggtgacc      600
cacgagggca gcaccgtgga aaagaccgtg gccccaaccg agtgcagc                  648
```

<210> SEQ ID NO 21
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Val Tyr Gly Met Asn
1               5

<210> SEQ ID NO 22
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Ile Ile Trp Tyr Asp Gly Asp Asn Gln Tyr Tyr Ala Asp Ser Val Lys
1               5                   10                  15

Gly

<210> SEQ ID NO 23
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Asp Leu Arg Thr Gly Pro Phe Asp Tyr
1               5

<210> SEQ ID NO 24
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Gly Phe Thr Phe Ser Val Tyr
1               5

<210> SEQ ID NO 25
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Trp Tyr Asp Gly Asp Asn
1               5

<210> SEQ ID NO 26
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Asp Leu Arg Thr Gly Pro Phe Asp Tyr
1               5

<210> SEQ ID NO 27
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Val Tyr
            20                  25                  30

Gly Met Asn Trp Val Arg Gln Ala Pro Gly Lys Gly Leu Glu Trp Val
        35                  40                  45

Ala Ile Ile Trp Tyr Asp Gly Asp Asn Gln Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Gly Leu Arg Ala Glu Asp Thr Ala Val Tyr Tyr Cys
                85                  90                  95

Ala Arg Asp Leu Arg Thr Gly Pro Phe Asp Tyr Trp Gly Gln Gly Thr
            100                 105                 110

Leu Val Thr Val Ser Ser
        115

<210> SEQ ID NO 28
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 28

```
caggtgcagc tggtggagag cggcggcggc gtggtgcagc ccggcaggag cctgaggctg    60
agctgcgccg ccagcggctt caccttcagc gtgtacggca tgaactgggt gaggcaggcc   120
cccggcaagg gcctggagtg ggtggccatc atctggtacg acggcgacaa ccagtactac   180
gccgacagcg tgaagggcag gttcaccatc agcagggaca cagcaagaa caccctgtac    240 ctgcagatga acggcctgag ggccgaggac accgccgtgt actactgcgc cagggacctg   300
aggaccggcc ccttcgacta ctggggccag ggcaccctgg tgaccgtgag cagc          354
```

<210> SEQ ID NO 29
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Val Tyr
            20                  25                  30

Gly Met Asn Trp Val Arg Gln Ala Pro Gly Lys Gly Leu Glu Trp Val
        35                  40                  45

Ala Ile Ile Trp Tyr Asp Gly Asp Asn Gln Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Gly Leu Arg Ala Glu Asp Thr Ala Val Tyr Tyr Cys
            85                  90                  95

Ala Arg Asp Leu Arg Thr Gly Pro Phe Asp Tyr Trp Gly Gln Gly Thr
        100                 105                 110

Leu Val Thr Val Ser Ser Ala Ser Thr Lys Gly Pro Ser Val Phe Pro
    115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
        180                 185                 190

Ser Leu Gly Thr Gln Thr Tyr Ile Cys Asn Val Asn His Lys Pro Ser
    195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255
```

```
Thr Pro Glu Val Thr Cys Val Val Asp Val Ser His Glu Asp Pro
            260                 265                 270
Glu Val Lys Phe Asn Trp Tyr Val Asp Gly Val Glu Val His Asn Ala
        275                 280                 285
Lys Thr Lys Pro Arg Glu Glu Gln Tyr Asn Ser Thr Tyr Arg Val Val
    290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Arg Glu Glu Met Thr Lys Asn Gln Val Ser Leu Thr Cys
        355                 360                 365
Leu Val Lys Gly Phe Tyr Pro Ser Asp Ile Ala Val Glu Trp Glu Ser
    370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly Lys
        435                 440                 445
```

<210> SEQ ID NO 30
<211> LENGTH: 1344
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 30

```
caggtgcagc tggtggagag cggcggcggc gtggtgcagc ccggcaggag cctgaggctg      60
agctgcgccg ccagcggctt caccttcagc gtgtacggca tgaactgggt gaggcaggcc     120
cccggcaagg gcctggagtg ggtggccatc atctggtacg acggcgacaa ccagtactac     180
gccgacagcg tgaagggcag gttcaccatc agcagggaca cagcaagaa caccctgtac     240
ctgcagatga acggcctgag ggccgaggac accgccgtgt actactgcgc cagggacctg     300
aggaccggcc ccttcgacta ctggggccag ggcaccctgg tgaccgtgag cagcgccagc     360
accaagggcc ccagcgtgtt ccccctggcc ccagcagca agagcaccag cggcggcacc     420
gccgccctgg gctgcctggt gaaggactac ttccccgagc ccgtgaccgt gagctggaac     480
agcggcgccc tgaccagcgg cgtgcacacc ttccccgccg tgctgcagag cagcggcctg     540
tacagcctga gcagcgtggt gaccgtgccc agcagcagcc tgggcaccca gacctacatc     600
tgcaacgtga accacaagcc cagcaacacc aaggtggaca gagggtgga gcccaagagc     660
tgcgacaaga cccacacctg ccccccctgc cccgccccg agctgctggg cggccccagc     720
gtgttcctgt tccccccaa gcccaaggac accctgatga tcagcaggac ccccgaggtg     780
acctgcgtgg tggtggacgt gagccacgag ccccgagg tgaagttcaa ctggtacgtg     840
gacggcgtga aggtgcacaa cgccaagacc aagcccaggg aggagcagta caacagcacc     900
tacagggtgg tgagcgtgct gaccgtgctg caccaggact ggctgaacgg caaggagtac     960
```

```
aagtgcaagg tgagcaacaa ggccctgccc gcccccatcg agaagaccat cagcaaggcc   1020
aagggccagc ccagggagcc ccaggtgtac accctgcccc ccagcaggga ggagatgacc   1080
aagaaccagg tgagcctgac ctgcctggtg aagggcttct accccagcga catcgccgtg   1140
gagtgggaga gcaacggcca gcccgagaac aactacaaga ccaccccccc cgtgctggac   1200
agcgacggca gcttcttcct gtacagcaag ctgaccgtgg acaagagcag gtggcagcag   1260
ggcaacgtgt tcagctgcag cgtgatgcac gaggccctgc acaaccacta cacccagaag   1320
agcctgagcc tgagccccgg caag                                           1344
```

<210> SEQ ID NO 31
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Arg Ala Ser Gln Ser Ile Gly Ser Ser Leu His
1               5                   10

<210> SEQ ID NO 32
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Tyr Ala Ser Gln Ser Phe Ser
1               5

<210> SEQ ID NO 33
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

His Gln Ser Ser Ser Leu Pro Phe Thr
1               5

<210> SEQ ID NO 34
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Ser Gln Ser Ile Gly Ser Ser
1               5

<210> SEQ ID NO 35
<211> LENGTH: 3
<212> TYPE: PRT

<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 35

Tyr Ala Ser
1

<210> SEQ ID NO 36
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 36

Ser Ser Ser Leu Pro Phe
1               5

<210> SEQ ID NO 37
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 37

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
            20                  25                  30

Leu His Trp Tyr Gln Gln Lys Pro Asp Gln Ser Pro Lys Leu Leu Ile
        35                  40                  45

Lys Tyr Ala Ser Gln Ser Phe Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Ala Tyr Tyr Cys His Gln Ser Ser Ser Leu Pro Phe
                85                  90                  95

Thr Phe Gly Pro Gly Thr Lys Val Asp Ile Lys
            100                 105

<210> SEQ ID NO 38
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 38
gagatcgtgc tgacccagtc acccgacttt cagtcagtga cccctaaaga aaaagtgact    60
atcacctgta gggcctccca gtctatcggc tctagcctgc actggtatca gcagaagccc   120
gatcagtcac ctaagctgct gattaagtac gcctctcagt cctttagcgg cgtgccctct   180
aggtttagcg gctcaggctc aggcaccgac ttcaccctga ctatcaatag cctggaagcc   240
gaggacgccg ctgcctacta ctgtcatcag tcaagtagcc tgcccttcac cttcggccct        300
ggcactaaag tggatattaa g        321

<210> SEQ ID NO 39
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
            20                  25                  30

Leu His Trp Tyr Gln Gln Lys Pro Asp Gln Ser Pro Lys Leu Leu Ile
        35                  40                  45

Lys Tyr Ala Ser Gln Ser Phe Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Ala Tyr Tyr Cys His Gln Ser Ser Ser Leu Pro Phe
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 40
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 40
gagatcgtgc tgacccagtc acccgacttt cagtcagtga cccctaaaga aaaagtgact        60
atcacctgta gggcctccca gtctatcggc tctagcctgc actggtatca gcagaagccc       120
gatcagtcac ctaagctgct gattaagtac gcctctcagt cctttagcgg cgtgccctct       180
aggtttagcg gctcaggctc aggcaccgac ttcaccctga ctatcaatag cctggaagcc       240
gaggacgccg ctgcctacta ctgtcatcag tcaagtagcc tgcccttcac cttcggccct       300

-continued

```
ggcactaaag tggatattaa gcgtacggtg gccgctccca gcgtgttcat cttcccccc    360 agcgacgagc agctgaagag cggcaccgcc agcgtggtgt gcctgctgaa caacttctac    420
ccccgggagg ccaaggtgca gtggaaggtg acaacgccc tgcagagcgg caacagccag     480
gagagcgtca ccgagcagga cagcaaggac tccacctaca gcctgagcag cacccctgacc  540 ctgagcaagg ccgactacga gaagcataag gtgtacgcct gcgaggtgac ccaccagggc   600
ctgtccagcc ccgtgaccaa gagcttcaac aggggcgagt gc                       642
```

<210> SEQ ID NO 41
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 41

Gly Phe Thr Phe Ser Val Tyr Gly Met Asn
1               5                   10

<210> SEQ ID NO 42
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 42

Ile Ile Trp Tyr Asp Gly Asp Asn Gln Tyr Tyr Ala Asp Ser Val Lys
1               5                   10                  15
Gly

<210> SEQ ID NO 43
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 43

Asp Leu Arg Thr Gly Pro Phe Asp Tyr
1               5

<210> SEQ ID NO 44
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 44

Val Tyr Gly Met Asn
1               5

<210> SEQ ID NO 45
<211> LENGTH: 17
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Ile Ile Trp Tyr Asp Gly Asp Asn Gln Tyr Tyr Ala Asp Ser Val Lys
1               5                   10                  15
Gly

<210> SEQ ID NO 46
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Asp Leu Arg Thr Gly Pro Phe Asp Tyr
1               5

<210> SEQ ID NO 47
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

Gly Phe Thr Phe Ser Val Tyr
1               5

<210> SEQ ID NO 48
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

Trp Tyr Asp Gly Asp Asn
1               5

<210> SEQ ID NO 49
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Asp Leu Arg Thr Gly Pro Phe Asp Tyr
1               5

<210> SEQ ID NO 50
<211> LENGTH: 8
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 50

Gly Phe Thr Phe Ser Val Tyr Gly
1               5

<210> SEQ ID NO 51
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Ile Trp Tyr Asp Gly Asp Asn Gln
1               5

<210> SEQ ID NO 52
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Ala Arg Asp Leu Arg Thr Gly Pro Phe Asp Tyr
1               5                   10

<210> SEQ ID NO 53
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 53

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Val Tyr
            20                  25                  30

Gly Met Asn Trp Val Arg Gln Ala Pro Gly Lys Gly Leu Glu Trp Val
        35                  40                  45

Ala Ile Ile Trp Tyr Asp Gly Asp Asn Gln Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Gly Leu Arg Ala Glu Asp Thr Ala Val Tyr Tyr Cys
                85                  90                  95

Ala Arg Asp Leu Arg Thr Gly Pro Phe Asp Tyr Trp Gly Gln Gly Thr
            100                 105                 110

Leu Val Thr Val Ser Ser
        115

<210> SEQ ID NO 54
<211> LENGTH: 354
<212> TYPE: DNA
```

<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 54

```
caggtgcagc tggtggaatc aggcggcgga gtggtgcagc tggtagatc actgagactg      60 agctgcgctg ctagtggctt caccttagc gtctacggaa tgaactgggt ccgacaggcc     120
cctgggaaag gcctggagtg gtggcaatt atctggtacg acggcgataa tcagtactac     180
gccgatagcg tgaagggacg gttcactatc tctagggata actctaagaa cacccctgta    240
ctgcagatga acggcctgag agccgaggac accgccgtct actactgcgc tagggacctg    300
agaaccggcc ccttcgacta ctggggacag ggcaccctgg tcaccgtgtc tagc          354
```

<210> SEQ ID NO 55
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 55

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Val Tyr
            20                  25                  30

Gly Met Asn Trp Val Arg Gln Ala Pro Gly Lys Gly Leu Glu Trp Val
        35                  40                  45

Ala Ile Ile Trp Tyr Asp Gly Asp Asn Gln Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Gly Leu Arg Ala Glu Asp Thr Ala Val Tyr Tyr Cys
                85                  90                  95

Ala Arg Asp Leu Arg Thr Gly Pro Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser His Glu Asp Pro
        260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Cys Thr Leu
            340                 345                 350

Pro Pro Ser Arg Glu Glu Met Thr Lys Asn Gln Val Ser Leu Ser Cys
        355                 360                 365

Ala Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 56
<211> LENGTH: 1344
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 56
caggtgcagc tggtggaatc aggcggcgga gtggtgcagc tggtagatc actgagactg      60 agctgcgctg ctagtggctt cacctttagc gtctacggaa tgaactgggt ccgacaggcc    120
cctgggaaag gcctggagtg ggtggcaatt atctggtacg acggcgataa tcagtactac    180
gccgatagcg tgaagggacg gttcactatc tctagggata actctaagaa caccctgtac    240
ctgcagatga acggcctgag agccgaggac accgccgtct actactgcgc tagggacctg    300
agaaccggcc ccttcgacta ctggggacag ggcaccctgg tcaccgtgtc tagcgcctct    360
actaagggcc caagcgtgtt ccccctggcc cctagctcta gtctactag cggaggcacc    420 gccgctctgg gctgcctggt caaggactac ttccccgagc ccgtgaccgt cagctggaat    480
agcggcgctc tgactagcgg agtgcacacc ttccccgccg tgctgcagtc tagcggcctg    540
tatagcctgt ctagcgtcgt gaccgtgcct agctctagcc tgggcactca gacctatatc    600
tgtaacgtga accacaagcc ctctaacact aaggtggaca gcgggtgga acctaagtcc     660 tgcgataaga ctcacacctg tcctccctgc cctgccctg aggctgccgg aggacctagc     720
gtgttcctgt tcccacctaa gcctaaagac accctgatga tctctaggac ccccgaagtg    780
acctgcgtgg tggtggacgt ctcacacgag gaccctgaag tgaagtttaa ttggtacgtg    840
gacggcgtgg aagtgcacaa cgctaagact aagcctagag aggaacagta taactctacc    900

```
tatagggtcg tcagcgtgct gacagtgctg caccaggact ggctgaacgg gaaagagtat    960
aagtgtaaag tgtctaacaa ggccctgcca gccctatcg aaaagactat ctctaaggct   1020
aaggggcagc ctagagaacc ccaagtgtgc actctgcccc ctagtagaga agagatgact   1080
aagaatcagg tgtcactgag ctgtgccgtg aagggcttct accctagcga tatcgccgtg   1140
gagtgggaga gcaacggcca gcccgagaac aactacaaga ccaccccccc agtgctggac   1200
agcgacggca gcttcttcct ggtgagcaag ctgaccgtgg acaagtccag gtggcagcag   1260
ggcaacgtgt tcagctgcag cgtgatgcac gaggccctgc acaaccacta cacccagaag   1320
tccctgagcc tgagccccgg caag                                          1344
```

<210> SEQ ID NO 57
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 57

Arg Ala Ser Gln Ser Ile Gly Ser Ser Leu His
1               5                   10

<210> SEQ ID NO 58
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 58

Tyr Ala Ser Gln Ser Phe Ser
1               5

<210> SEQ ID NO 59
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 59

His Gln Ser Ser Ser Leu Pro Phe Thr
1               5

<210> SEQ ID NO 60
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 60

Arg Ala Ser Gln Ser Ile Gly Ser Ser Leu His
1               5                   10

<210> SEQ ID NO 61
<211> LENGTH: 7

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 61

Tyr Ala Ser Gln Ser Phe Ser
1               5

<210> SEQ ID NO 62
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62

His Gln Ser Ser Ser Leu Pro Phe Thr
1               5

<210> SEQ ID NO 63
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

Ser Gln Ser Ile Gly Ser Ser
1               5

<210> SEQ ID NO 64
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 64

Tyr Ala Ser
1

<210> SEQ ID NO 65
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 65

Ser Ser Ser Leu Pro Phe
1               5

<210> SEQ ID NO 66
<211> LENGTH: 6
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic peptide"

<400> SEQUENCE: 66

Gln Ser Ile Gly Ser Ser
1               5

<210> SEQ ID NO 67
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 67

Tyr Ala Ser Gln Ser Phe Ser Gly Val Pro
1               5                   10

<210> SEQ ID NO 68
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 68

His Gln Ser Ser Ser Leu Pro Phe Thr
1               5

<210> SEQ ID NO 69
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 69

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
            20                  25                  30

Leu His Trp Tyr Gln Gln Lys Pro Asp Gln Ser Pro Lys Leu Leu Ile
        35                  40                  45

Lys Tyr Ala Ser Gln Ser Phe Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Ala Tyr Tyr Cys His Gln Ser Ser Ser Leu Pro Phe
                85                  90                  95

Thr Phe Gly Pro Gly Thr Lys Val Asp Ile Lys
            100                 105

<210> SEQ ID NO 70
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic polynucleotide"

<400> SEQUENCE: 70

```
gagatcgtgc tgacccagtc acccgacttt cagtcagtga cccctaaaga aaaagtgact    60
atcacctgta gggcctccca gtctatcggc tctagcctgc actggtatca gcagaagccc   120
gatcagtcac ctaagctgct gattaagtac gcctctcagt cctttagcgg cgtgccctct   180
aggtttagcg gctcaggctc aggcaccgac ttcaccctga ctatcaatag cctggaagcc   240
gaggacgccg ctgcctacta ctgtcatcag tcaagtagcc tgcccttcac cttcggccct   300
ggcactaaag tggatattaa g                                              321
```

<210> SEQ ID NO 71
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 71

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
            20                  25                  30

Leu His Trp Tyr Gln Gln Lys Pro Asp Gln Ser Pro Lys Leu Leu Ile
        35                  40                  45

Lys Tyr Ala Ser Gln Ser Phe Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Ala Tyr Tyr Cys His Gln Ser Ser Ser Leu Pro Phe
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 72
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

-continued

<400> SEQUENCE: 72

```
gagatcgtgc tgacccagtc acccgacttt cagtcagtga cccctaaaga aaaagtgact    60
atcacctgta gggcctccca gtctatcggc tctagcctgc actggtatca gcagaagccc   120
gatcagtcac ctaagctgct gattaagtac gcctctcagt cctttagcgg cgtgccctct   180
aggtttagcg gctcaggctc aggcaccgac ttcaccctga ctatcaatag cctggaagcc   240
gaggacgccg ctgcctacta ctgtcatcag tcaagtagcc tgcccttcac cttcggccct   300
ggcactaaag tggatattaa gcgtacggtg gccgctccca gcgtgttcat cttccccccc   360
agcgacgagc agctgaagag cggcaccgcc agcgtggtgt gcctgctgaa caacttctac   420
ccccgggagg ccaaggtgca gtggaaggtg acaacgccc tgcagagcgg caacagccag   480
gagagcgtca ccgagcagga cagcaaggac tccacctaca gcctgagcag caccctgacc   540
ctgagcaagg ccgactacga gaagcataag gtgtacgcct gcgaggtgac ccaccagggc   600
ctgtccagcc ccgtgaccaa gagcttcaac aggggcgagt gc                      642
```

<210> SEQ ID NO 73
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 73

```
Gly Gly Thr Phe Lys Ser Tyr Ala Ile Ser
1               5                   10
```

<210> SEQ ID NO 74
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 74

```
Asn Ile Ile Pro Met Thr Gly Gln Thr Tyr Tyr Ala Gln Lys Phe Gln
1               5                   10                  15

Gly
```

<210> SEQ ID NO 75
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 75

```
Ala Ala Tyr His Pro Leu Val Phe Asp Asn
1               5                   10
```

<210> SEQ ID NO 76
<211> LENGTH: 5
<212> TYPE: PRT
<213> ORGANISM: Artificial Sequence
<220> FEATURE:
<221> NAME/KEY: source

```
<223> OTHER INFORMATION: /note="Description of Artificial Sequence:
      Synthetic peptide"

<400> SEQUENCE: 76

Ser Tyr Ala Ile Ser
1               5

<210> SEQ ID NO 77
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 77

Asn Ile Ile Pro Met Thr Gly Gln Thr Tyr Tyr Ala Gln Lys Phe Gln
1               5                   10                  15

Gly

<210> SEQ ID NO 78
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 78

Ala Ala Tyr His Pro Leu Val Phe Asp Asn
1               5                   10

<210> SEQ ID NO 79
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 79

Gly Gly Thr Phe Lys Ser Tyr
1               5

<210> SEQ ID NO 80
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 80

Ile Pro Met Thr Gly Gln
1               5

<210> SEQ ID NO 81
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 81

Ala Ala Tyr His Pro Leu Val Phe Asp Asn
1               5                   10

<210> SEQ ID NO 82
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 82

Gly Gly Thr Phe Lys Ser Tyr Ala
1               5

<210> SEQ ID NO 83
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 83

Ile Ile Pro Met Thr Gly Gln Thr
1               5

<210> SEQ ID NO 84
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 84

Ala Arg Ala Ala Tyr His Pro Leu Val Phe Asp Asn
1               5                   10

<210> SEQ ID NO 85
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 85

Glu Val Gln Leu Val Gln Ser Gly Ala Glu Val Lys Lys Pro Gly Ser
1               5                   10                  15

Ser Val Lys Val Ser Cys Lys Ala Ser Gly Thr Phe Lys Ser Tyr
            20                  25                  30

Ala Ile Ser Trp Val Arg Gln Ala Pro Gly Gln Gly Leu Glu Trp Met
        35                  40                  45

Gly Asn Ile Ile Pro Met Thr Gly Gln Thr Tyr Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys

```
                    85                  90                  95
Ala Arg Ala Ala Tyr His Pro Leu Val Phe Asp Asn Trp Gly Gln Gly
                100                 105                 110

Thr Leu Val Thr Val Ser Ser
        115

<210> SEQ ID NO 86
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 86
gaggtgcagc tggtgcagtc aggcgccgaa gtgaagaaac ccggctctag cgtgaaagtc    60
agctgtaaag ctagtggcgg caccttcaag tcctacgcta ttagctgggt cagacaggcc   120
ccaggtcagg gcctggagtg gatgggcaat attatcccta tgaccggtca gacctactac   180
gctcagaaat tcagggtag agtgactatc accgccgacg agtctactag caccgcctat   240
atggaactgt ctagcctgag atcagaggac accgccgtct actactgcgc tagagccgcc   300
tatcaccccc tggtgttcga taactggggt cagggcaccc tggtcaccgt gtctagc      357

<210> SEQ ID NO 87
<211> LENGTH: 449
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 87

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Lys Ser Tyr
            20                  25                  30

Ala Ile Ser Trp Val Arg Gln Ala Pro Gly Gln Gly Leu Glu Trp Met
        35                  40                  45

Gly Asn Ile Ile Pro Met Thr Gly Gln Thr Tyr Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Ala Tyr His Pro Leu Val Phe Asp Asn Trp Gly Gln Gly
                100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190
```

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Cys Arg Glu Glu Met Thr Lys Asn Gln Val Ser Leu Trp
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 88
<211> LENGTH: 1347
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 88
gaggtgcagc tggtgcagtc aggcgccgaa gtgaagaaac ccggctctag cgtgaaagtc    60
agctgtaaag ctagtggcgg caccttcaag tcctacgcta ttagctgggt cagacaggcc   120
ccaggtcagg gcctggagtg gatgggcaat attatcccta tgaccggtca gacctactac   180
gctcagaaat ttcagggtag agtgactatc accgccgacg agtctactag caccgcctat   240
atggaactgt ctagcctgag atcagaggac accgccgtct actactgcgc tagagccgcc   300
tatcaccccc tggtgttcga taactggggt cagggcaccc tggtcaccgt gtctagcgct   360
agcactaagg gcccctcagt gttcccccctg gcccctagcc taagtctac tagcggcggc   420 accgccgctc tgggctgcct ggtgaaagac tacttccccg agcccgtgac cgtgtcatgg   480

```
aatagcggcg ctctgactag cggagtgcac accttccccg ccgtgctgca gtctagcggc    540
ctgtatagcc tgtctagcgt ggtgaccgtg cctagctcta gcctgggcac tcagacctac    600
atctgtaacg tgaaccacaa gccctctaac actaaggtgg acaagcgggt ggaacctaag    660
tcctgcgata agactcacac ctgtcccccc tgccctgccc ctgaggctgc cggaggacct    720
agcgtgttcc tgttcccacc taagcctaag dacaccctga tgatctctag gaccccgaa     780 gtgacctgcg tggtggtgga tgtgtctcac gaggaccctg aagtgaagtt caattggtac    840
gtggacggcg tggaagtgca caacgctaag actaagccta gagaggaaca gtataactcc    900
acctatagag tggtgtcagt gctgaccgtg ctgcatcagg actggctgaa cggcaaagag    960
tataagtgta aagtctctaa caaggccctg ccagcccta tcgaaaagac tatctctaag    1020
gctaagggcc agcctagaga acctcaggtg tacaccctgc cccctgtag agaagagatg    1080 actaagaatc aggtgtccct gtggtgtctg gtgaaaggct tctaccctag cgatatcgcc    1140
gtggaatggg agtctaacgg ccagcccgag aacaactata agactacccc ccctgtgctg    1200
gatagcgacg gctcattctt cctgtactct aagctgaccg tggacaagtc taggtggcag    1260
cagggcaatg tgtttagctg tagcgtgatg cacgaggccc tgcataatca ctacactcag    1320
aagtcactga gcctgagccc cggcaag                                       1347
```

<210> SEQ ID NO 89
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 89

Ser Gly Ser Ser Ser Asn Ile Gly Asn His Tyr Val Asn
1               5                   10

<210> SEQ ID NO 90
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 90

Arg Asn Asn His Arg Pro Ser
1               5

<210> SEQ ID NO 91
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 91

Gln Ser Trp Asp Tyr Ser Gly Phe Ser Thr Val
1               5                   10

<210> SEQ ID NO 92
<211> LENGTH: 13
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 92

Ser Gly Ser Ser Ser Asn Ile Gly Asn His Tyr Val Asn
1               5                   10

<210> SEQ ID NO 93
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 93

Arg Asn Asn His Arg Pro Ser
1               5

<210> SEQ ID NO 94
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 94

Gln Ser Trp Asp Tyr Ser Gly Phe Ser Thr Val
1               5                   10

<210> SEQ ID NO 95
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 95

Ser Ser Ser Asn Ile Gly Asn His Tyr
1               5

<210> SEQ ID NO 96
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 96

Arg Asn Asn
1

<210> SEQ ID NO 97
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
```

```
        Synthetic peptide"

<400> SEQUENCE: 97

Trp Asp Tyr Ser Gly Phe Ser Thr
1               5

<210> SEQ ID NO 98
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
        Synthetic peptide"

<400> SEQUENCE: 98

Ser Ser Asn Ile Gly Asn His Tyr
1               5

<210> SEQ ID NO 99
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
        Synthetic peptide"

<400> SEQUENCE: 99

Arg Asn Asn
1

<210> SEQ ID NO 100
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
        Synthetic peptide"

<400> SEQUENCE: 100

Gln Ser Trp Asp Tyr Ser Gly Phe Ser Thr Val
1               5                   10

<210> SEQ ID NO 101
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
        Synthetic polypeptide"

<400> SEQUENCE: 101

Asp Ile Val Leu Thr Gln Pro Pro Ser Val Ser Gly Ala Pro Gly Gln
1               5                   10                  15

Arg Val Thr Ile Ser Cys Ser Gly Ser Ser Asn Ile Gly Asn His
            20                  25                  30

Tyr Val Asn Trp Tyr Gln Gln Leu Pro Gly Thr Ala Pro Lys Leu Leu
            35                  40                  45

Ile Tyr Arg Asn Asn His Arg Pro Ser Gly Val Pro Asp Arg Phe Ser
        50                  55                  60

Gly Ser Lys Ser Gly Thr Ser Ala Ser Leu Ala Ile Thr Gly Leu Gln
65                  70                  75                  80
```

```
Ser Glu Asp Glu Ala Asp Tyr Tyr Cys Gln Ser Trp Asp Tyr Ser Gly
                85                  90                  95

Phe Ser Thr Val Phe Gly Gly Gly Thr Lys Leu Thr Val Leu
            100                 105                 110
```

<210> SEQ ID NO 102
<211> LENGTH: 330
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 102

```
gatatcgtcc tgactcagcc ccctagcgtc agcggcgctc ccggtcagag agtgactatt      60
agctgtagcg gctctagctc taatatcggt aatcactacg tgaactggta tcagcagctg     120
cccggcaccg cccctaagct gctgatctat agaaacaatc accggcctag cggcgtgccc     180
gataggttta gcggatctaa gtcaggcact agcgctagtc tggctatcac cggactgcag     240
tcagaggacg aggccgacta ctactgtcag tcctgggact atagcggctt tagcaccgtg     300
ttcggcggag gcactaagct gaccgtgctg                                      330
```

<210> SEQ ID NO 103
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 103

```
Asp Ile Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Asn His
            20                  25                  30

Tyr Val Asn Trp Tyr Gln Gln Leu Pro Gly Thr Ala Pro Lys Leu Leu
        35                  40                  45

Ile Tyr Arg Asn Asn His Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Gln Ser Trp Asp Tyr Ser Gly
                85                  90                  95

Phe Ser Thr Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
```

```
              195                 200                 205
Thr Val Ala Pro Thr Glu Cys Ser
    210                 215

<210> SEQ ID NO 104
<211> LENGTH: 648
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 104
gatatcgtcc tgactcagcc ccctagcgtc agcggcgctc ccggtcagag agtgactatt      60
agctgtagcg gctctagctc taatatcggt aatcactacg tgaactggta tcagcagctg     120
cccggcaccg cccctaagct gctgatctat agaaacaatc accggcctag cggcgtgccc     180
gataggttta gcggatctaa gtcaggcact agcgctagtc tggctatcac cggactgcag     240
tcagaggacg aggccgacta ctactgtcag tcctgggact atagcggctt tagcaccgtg     300
ttcggcggag gcactaagct gaccgtgctg ggtcagccta aggctgcccc cagcgtgacc     360
ctgttccccc ccagcagcga ggagctgcag gccaacaagg ccaccctggt gtgcctgatc     420
agcgacttct acccaggcgc cgtgaccgtg gcctggaagg ccgacagcag ccccgtgaag     480
gccggcgtgg agaccaccac ccccagcaag cagagcaaca acaagtacgc cgccagcagc     540
tacctgagcc tgacccccga gcagtggaag agccacaggt cctacagctg ccaggtgacc     600
cacgagggca gcaccgtgga aaagaccgtg gccccaaccg agtgcagc                  648
```

METHOD OF MANUFACTURING BISPECIFIC ANTIBODIES, BISPECIFIC ANTIBODIES AND THERAPEUTIC USE OF SUCH ANTIBODIES

STATEMENT OF RELATED APPLICATIONS

This application is a continuation of U.S. patent application Ser. No. 16/005,088 filed Jun. 11, 2018 which claims priority to U.S. provisional patent application No. 62/518,090, filed Jun. 12, 2017, the contents of which are incorporated herein by reference in their entirety.

SEQUENCE LISTING

The instant application contains a Sequence Listing which has been submitted electronically in ASCII format and is hereby incorporated by reference in its entirety. Said ASCII copy, created on May 30, 2018, is named PAT057716-WO-PCT_SL.txt and is 68,498 bytes in size.

TECHNICAL FIELD

The invention relates to bivalent bispecific monoclonal antibodies (bbmAb) or variants thereof, and methods of manufacturing such antibodies by co-expressing so called knob-into-hole modified FC-mutated derivatives of two different monoclonal antibodies in mammalian cell lines.

BACKGROUND OF THE DISCLOSURE

Bispecific antibodies, i.e. antibodies binding to two distinct epitopes, are well known in the art. One approach for generating bispecific antibodies is the so called knobs-into-holes (KiH) approach described e.g. by Merchant et al., Nat. Biotechnol., 16:677-681 (1998), where a first heavy chain IgG is modified to display a hole like structure by introducing point mutations like Y349C, T366S, L368A, Y407V; and where a second heavy chain IgG is modified to display a knob like structure, by introducing point mutations S354C, T366W ((Merchant et al., Nat. Biotechnol., 16:677-681 (1998), page 678, table 1). The two different IgG structures then interact to form a bivalent bispecific antibody (bbmAb), i.e. a hetero-tetrameric protein, consisting of two different light and two different heavy chains.

When expressing two KiH modified mAbs in the same host cell line, the desired bbmAb statistically makes up only 25% of the expressed protein, but 75% are so called product related impurities (Klein, Ch. et al., 2012).

Some approaches to overcome this are known in the art, such as facilitating correct formation of bbmAbs by apply further sequence modifications to enforce the correct H-L-binding (for overview see Klein, Ch. et al., 2012; Kontermann, R. and Brinkmann, U., 2015). However, such additional modifications might increase the risk of anti-drug antibodies.

Another approach to generate bbmAbs is disclosed in WO12023053A2 or WO04009618A2, utilizing a shared heavy or light chain in combination with different variable chains. However, keeping either the heavy chain constant significantly reduces the diversity of the antibody repertoire where the binders can be screened.

Yet another approach to generation of bbmAbs is disclosed in U.S. Pat. No. 9,212,230, and entails individual expression and purification of the mAbs carrying different modifications. The resulting mAbs are finally shuffled in vitro to form the intended bbmAb. Such in vitro shuffling is a complex additional process step which required careful validation and analytical assessment, and could significantly increase the costs.

Thus, existing methods for generating bbmAbs might either limit diversity of the antibody repertoire available to screen for binders or might not provide sufficient overall yield, purity and product quality at a sufficiently cost effective way to enable manufacturing in a scale feasible for clinical development and commercialization. In addition, any modification of protein chains inherently increases the risk to induce anti-drug antibodies. Therefore, approaches which only require minimal protein engineering might be clinically favorable.

SUMMARY OF THE DISCLOSURE

There is a need to provide an improved method for manufacturing of bivalent bispecific antibodies. Particularly, there is a need for a method for manufacturing of bivalent bispecific monoclonal antibodies (bbmAb), ensuring a sufficient overall yield, purity and product quality to proceed with clinical development and commercial manufacturing, at a reasonable cost.

The present invention provides inter alia a method for the generation of bbmAbs with one or more of the following advantages: it enables the use of a large antibody repertoire to identify binders as no shared light or heavy chains are required, it does not require any extensive protein engineering, beside the mutation driving the H-chain dimerization, and therefore limits the risk for anti-drug antibodies, it is cost effective as expression is done in a common cell line, therefore the bbmAb can be produced in one cell culture process without the need for a specific in vitro shuffling and it produces high quality material suitable for human use as product related impurities can be efficiently removed.

The present invention is useful for identifying antibodies of kappa and lambda type, where the light chains do not show a strong promiscuous binding towards the heavy chain of the counterpart. This makes the antibodies suitable for use in methods of the invention. An advantage of the method may be that antibody combinations where both light chains exchange the original heavy chain binding partner, which results in a product related impurity of the H1L2-H2L1 type, can be deselected. This is advantageous, because such product related impurities are not easy to deplete using state of the art purification processes.

As will be shown below, embodiments of the invention enable manufacturing of bbmAb by the use of a CHO co-expression at a yield and quality suitable for clinical development and commercialization of biologics.

In a first aspect of the invention a bispecific antibody suitable for co-expression in a common host cell is provided, wherein the antibody comprises a) a first part which is an immunoglobulin with a variable light chain of lambda wild type (VL1) and a variable heavy chain of wild type (VH1), that binds specifically to a first target, and a first constant heavy chain (CH1) with a hetero-dimerization modification, and b) a second part which is an immunoglobulin with a variable light chain of kappa wild type (L2) and a variable heavy chain of wild type (H2), that binds specifically to a second target, different from the first target, and a second constant heavy chain (CH2) with a hetero-dimerization modification which is complementary to the hetero-dimerization modification of the first constant heavy chain, wherein the first part and the second part, when co-expressed in a common host cell, form a bispecific antibody.

In a further embodiment of the first aspect, the bispecific antibody suitable for co-expression in a common host cell results, after purifying the bispecific antibody by removing mismatched fragments from the correctly matched bispecific antibody, in a bispecific antibody which is at least 60% (mass), 70% (mass), 80% (mass), 85% (mass) pure, such as at least 90% (mass) pure, 95% (mass), 96% (mass), 97% (mass), 98% (mass), or 99% (mass) pure.

The first and second constant heavy chain of the bispecific antibody may be human IgA, IgD, IgE, IgG, or IgM, preferably IgD, IgE or IgG. In a preferred embodiment, the first and second constant heavy chains are human IgG1, IgG2, IgG3, or IgG4, most preferably IgG1. In one embodiment, the first variable light chain is of lamba type, and the second variable light chain is of kappa type.

In a specifically preferred embodiment, the first variable light chain is of lamba1 type, and the second variable light chain is of kappa 6 type.

The first and second constant heavy chain may be IgG1, wherein the first constant heavy chain has point mutations generating a knob structure and the second constant heavy has point mutations generating a hole structure, or the first constant heavy chain has point mutations generating a hole structure and the second constant heavy has point mutations generating a knob structure. Optionally, the first and second constant heavy chains can additionally have mutations resulting in a disulfide bridge.

In one embodiment, the bispecific antibody comprises a first immunoglobulin VH1 domain, a first immunoglobulin VL1 domain, a second immunoglobulin VH2 domain and a second immunoglobulin VL2 domain, wherein the first immunoglobulin VH1 domain comprises (e.g. in sequence): hypervariable regions CDR1, CDR2 and CDR3, said CDR1 having the amino acid sequence SEQ ID NO:76, said CDR2 having the amino acid sequence SEQ ID NO:77, and said CDR3 having the amino acid sequence SEQ ID NO:78; or hypervariable regions CDR1, CDR2 and CDR3, said CDR1 having the amino acid sequence SEQ ID NO:79, said CDR2 having the amino acid sequence SEQ ID NO:80, and said CDR3 having the amino acid sequence SEQ ID NO:81; and the first immunoglobulin VL1 domain comprises (e.g. in sequence): hypervariable regions CDR1, CDR2 and CDR3, said CDR1 having the amino acid sequence SEQ ID NO:92, said CDR2 having the amino acid sequence SEQ ID NO:93, and said CDR3 having the amino acid sequence SEQ ID NO:94 or hypervariable regions CDR1, CDR2 and CDR3, said CDR1 having the amino acid sequence SEQ ID NO:95, said CDR2 having the amino acid sequence SEQ ID NO:96, and said CDR3 having the amino acid sequence SEQ ID NO:97; the second immunoglobulin VH2 domain comprises (e.g. in sequence): hypervariable regions CDR1, CDR2 and CDR3, said CDR1 having the amino acid sequence SEQ ID NO:44, said CDR2 having the amino acid sequence SEQ ID NO:45, and said CDR3 having the amino acid sequence SEQ ID NO:46; or hypervariable regions CDR1, CDR2 and CDR3, said CDR1 having the amino acid sequence SEQ ID NO:47, said CDR2 having the amino acid sequence SEQ ID NO:48, and said CDR3 having the amino acid sequence SEQ ID NO:49; and the second immunoglobulin VL2 domain comprises (e.g. in sequence): hypervariable regions CDR1, CDR2 and CDR3, said CDR1 having the amino acid sequence SEQ ID NO:60, said CDR2 having the amino acid sequence SEQ ID NO:61, and said CDR3 having the amino acid sequence SEQ ID NO:62 or hypervariable regions CDR1, CDR2 and CDR3, said CDR1 having the amino acid sequence SEQ ID NO:63, said CDR2 having the amino acid sequence SEQ ID NO:64, and said CDR3 having the amino acid sequence SEQ ID NO:65.

In one embodiment, the bispecific antibody comprises a first immunoglobulin VH1 domain, a first immunoglobulin VL1 domain, a second immunoglobulin VH2 domain and a second immunoglobulin VL2 domain, wherein: the first immunoglobulin VH1 domain comprises the amino acid sequence SEQ ID NO: 85, the first immunoglobulin VL1 domain comprises the amino acid sequence SEQ ID NO: 101, the second immunoglobulin VH2 domain comprises the amino acid sequence SEQ ID NO: 53, the second immunoglobulin VL2 domain comprises the amino acid sequence SEQ ID NO: 69.

In one embodiment, the bispecific antibody comprises a first immunoglobulin heavy chain, a first immunoglobulin light chain, a second immunoglobulin heavy chain and a second immunoglobulin light chain, wherein: the first immunoglobulin heavy chain comprises the amino acid sequence SEQ ID NO: 87, the first immunoglobulin light chain comprises the amino acid sequence SEQ ID NO: 103, the second immunoglobulin heavy chain comprises the amino acid sequence SEQ ID NO: 55, the second immunoglobulin light chain comprises the amino acid sequence SEQ ID NO: 71.

According to a second aspect, a method for selecting a bispecific antibody according to the first aspect is provided, said method comprising; a first step of selecting the first part, and the second part; a second step of co-expressing the first part and the second part in a common host cell, resulting in a bispecific antibody comprising the first part and the second part; a third step of purifying the bispecific antibody by removing mismatched fragments from the correctly matched bispecific antibody. In an embodiment, the third step of purification results in a bispecific antibody which is at least 60% (mass), 70% (mass), 80% (mass), 85% (mass) pure, such as at least 90% (mass) pure, 95% (mass), 96% (mass), 97% (mass), 98% (mass), or 99% (mass) pure.

According to a third aspect, a method for manufacturing a bispecific antibody according to the first aspect by co-expression in a common host cell is provided, said method comprising; a first step of generating at least one vector encoding the first part and the second part; a second step of introducing the at least one vector into the common host cell; a third step of selecting cells specifically expressing the bispecific antibody; a forth step of culturing the selected cells under conditions wherein the cells express the bispecific antibody; and a fifth step of purifying the bispecific antibody which is at least 60% (mass), 70% (mass), 80% (mass), 85% (mass) pure, such as at least 90% (mass) pure, 95% (mass), 96% (mass), 97% (mass), 98% (mass), or 99% (mass) pure.

In an embodiment, the first step comprises generating a first vector encoding the first part and a second vector encoding the second part.

According to a fourth aspect, an expression system comprising at least one vector comprising a polynucleotide encoding the first part or the second part of the bispecific antibody according to the first aspect, and a selectable marker.

In an embodiment, the expression system comprises a polynucleotide encoding a first selectable marker (sm I); and a polynucleotide encoding a second selectable marker (sm II), which differs from the first selectable marker (sm I).

In an embodiment, the first selectable marker (sm I) is a folate transporter or a polynucleotide encoding a mutated folate receptor, wherein the mutated folate receptor has a decreased folate binding affinity compared to the wildtype folate receptor and the second selectable marker (sm II) is DHFR.

In an embodiment, the first selectable marker (sm I) is Hygromycine and the second selectable marker (sm II) is Neo/G418.

In an embodiment, the expression system comprises two expression vectors wherein: a first vector comprising polynucleotide encoding at least a first selectable marker (sm I) and at least polynucleotides encoding the first part; and a second vector comprising polynucleotide encoding at least a second selectable marker (sm II) and at least polynucleotides encoding the second part.

The expression system may comprise a stop codon downstream of the polynucleotides encoding the heavy chain and a polynucleotide encoding an immunoglobulin membrane anchor located downstream of the stop codon.

According to a fifth aspect, a method for selecting a common host cell for use in a method according to previous aspects is provided, comprising a first step of providing a plurality of host cells, comprising the expression system according to previous aspects; and culturing said plurality of host cells under conditions selective for the selectable marker, thereby obtaining a host cell expressing the product of interest.

In an embodiment, the selective culture medium is selected from the group comprising a medium comprising a limiting concentration of folate; and/or comprising a folic acid in a concentration of 500 nM or less; and/or comprising a folic acid in a concentration selected from: 1000 nM-100 pM; 100 nM-1 nM; 15 nM-1 nM; 10 nM-1 nM; and 10 nM-2.5 nM; and/or comprising a DHFR inhibitor; and/or comprising an antifolate; and/or comprising an antifolate in a concentration of 500 nM or less; and/or comprising MTX in a concentration selected from: 500 nM-3 nM; 100 nM-10 nM; 50 nM-10 nM; and 50 nM; and/or comprising a concentration of antifolate up to 20-fold of the folate concentration; and/or comprising a concentration of antifolate 10-20 fold of the folate concentration; and/or comprising a folic acid in a concentration up to 15 nM and an equimolar concentration up to 20-fold of MTX.

In an embodiment, the host cell comprises the expression system wherein at least a portion of the first or second part is expressed as a fusion polypeptide comprising the immunoglobulin transmembrane anchor or fragment thereof, wherein said fusion polypeptide is being displayed on the surface of said host cell, further comprising a step of: contacting the plurality of host cells with a detection compound binding the fusion polypeptide; selecting at least one host cell based upon the presence or amount of the detection compound bound to the cell surface.

In an embodiment, the detection compound comprises the first or second target, or derivatives thereof, and a detection label.

In an embodiment, the fifth step of purifying the bispecific antibody comprises affinity chromatography and/or ion exchange chromatography.

In an embodiment, the chromatography comprises a first step of capturing; a second step of polishing; and optionally a third step of polishing.

In an embodiment, the first step of capturing is performed with a principle selected the group consisting of Fc-binding affinity chromatography, such as Protein A or Protein G, lambda light chain specific affinity chromatography, well known in the art, and readily available commercially, for example LambdaFabSelect™, kappa light chain specific affinity chromatography, well known in the art, and readily available commercially, for example KappaSelect™, anti-idiotypic affinity chromatography, such as the first part or the second part, a target based affinity chromatography, such as affinity chromatography using the first target or second target, ion exchange chromatography, well known in the art, and readily available commercially, for example Capto™ adhere, or Fractogel™ EMD $SO_3$, and hydrophobic interaction chromatography.

In an embodiment, the second step of polishing is performed with a principle selected the group consisting of Fc-binding affinity chromatography, such as Protein A or Protein G, lambda light chain specific affinity chromatography, such as LambdaFabSelect™, kappa light chain specific affinity chromatography, such as KappaSelect™, anti-idiotypic affinity chromatography, such as the first part or the second part, a target based affinity chromatography, such as affinity chromatography using the first target or second target, ion exchange chromatography, such as Capto™ adhere, or Fractogel™ EMD $SO_3$, hydrophobic interaction chromatography, and virus inactivation.

In an embodiment, the third step of polishing is performed with a principle selected the group consisting of Fc-binding affinity chromatography, such as Protein A or Protein G, lambda light chain specific affinity chromatography, such as LambdaFabSelect™, kappa light chain specific affinity chromatography, such as KappaSelect™, anti-idiotypic affinity chromatography, such as the first part or the second part, a target based affinity chromatography, such as affinity chromatography using the first target or second target, ion exchange chromatography, such as Capto™ adhere, or Fractogel™ EMD $SO_3$, hydrophobic interaction chromatography, and virus inactivation.

In an embodiment, the method comprises a first step of Protein A capturing, such as MabSelect™ SuRe™, a second step of lambda light chain affinity chromatography, such as LambdaFabSelect™, and a third step of kappa light chain affinity chromatography such as KappaSelect™; or a first step of Protein A, such as MabSelect™ SuRe™, a second step of kappa light chain affinity chromatography such as KappaSelect™, and a third step of lambda light chain affinity chromatography, such as LambdaFabSelect™; or a first step of kappa light chain affinity chromatography such as KappaSelect™ and a second step of lambda light chain affinity chromatography, such as LambdaFabSelect™; or a first step of lambda light chain affinity chromatography, such as LambdaFabSelect™ and a second step of kappa light chain affinity chromatography such as KappaSelect™.

In an embodiment, the cell line is selected from the group consisting of a CHO cell, a non-producing hybridoma, such as Sp 2/0 or NS0, a human derived cell line, such as HEK or PER.C6, a baby hamster kidney (BHK) derivative, a yeast or filamentous fungi, a prokaryotic bacteria, such as *E. coli* or *Pseudomonas* fluorescence, a plant derivative, an algae and a ciliate.

According to a sixth aspect, a pharmaceutical composition is provided, comprising the antibody according to the first aspect and a pharmaceutically acceptable carrier.

According to a seventh aspect, an antibody according to a first aspect, or the pharmaceutical composition according to the sixth aspect, for use as a medicament is provided.

According to a seventh aspect, an antibody according to a first aspect, or the pharmaceutical composition according to the sixth aspect, for use as in the treatment of an inflammasome related disease is provided.

According to an eight aspect, an antibody according to a first aspect, or the pharmaceutical composition according to the sixth aspect, for use as in the treatment of an inflammasome related disease is provided, wherein the inflammasome related disease is selected from the group consisting of sickle cell disease, vasculopathy, ischemia-reperfusion injury, cardiovascular disease, peripheral artery disease, atherosclerosis, vascular dysfunction, skeletal muscle ischemia, pulmonary sarcoidosis, fibrosis, malaria, hemodialysis-dependent, chronic kidney disease and Crohn's disease.

According to a ninth aspect, a method of treating an inflammasome related disorder comprising administering to a subject afflicted with a inflammasome related disorder an effective amount of an antibody according to the first aspect or a pharmaceutical composition according to the sixth aspect is provided.

The inflammasome related disorder may be sickle cell disease, vasculopathy, ischemia-reperfusion injury, cardiovascular disease, peripheral artery disease, atherosclerosis, vascular dysfunction, skeletal muscle ischemia, pulmonary sarcoidosis, fibrosis, malaria, hemodialysis-dependent, chronic kidney disease or Crohn's disease.

BRIEF DESCRIPTION OF THE FIGURES

FIG. 2A is a RP-UV chromatogram of a de-glycosylated intact bbmAb according to an embodiment. FIG. 2B is a de-convoluted mass spectrum of the intact de-glycosylated bbmAb1 according to an embodiment. FIG. 2C is a RP-UV chromatogram showing papain digested fragments of a bbmAb according to an embodiment. FIG. 2D is a RP-UV chromatogram showing IdeS digested fragments of a bbmAb according to an embodiment. FIG. 2E is a RP-UV chromatogram showing de-glycosylated and DTT reduced fragments of a bbmAb according to an embodiment.

FIG. 3A-3D shows RP-UV chromatograms according to an embodiment. FIG. 3A is a chromatogram showing the expression purity profile of a bbmAb according to an embodiment after cultivation. FIG. 3B is a chromatogram of a bbmAb according to an embodiment after capturing by LambdaFabSelect™. FIG. 3C is a chromatogram of a bbmAb according to an embodiment after capturing with MabSelect™ SuRe™ FIG. 3D is a chromatogram of a bbmAb according to an embodiment after capturing with LambdaFabSelect™, polish by Fractogel™ EMD SO₃ and ultrafiltration.

FIG. 4A is a schematic representation of a mAb1 knob (lambda) monomer, where number 1 represents the variable heavy domain, number 2 represents the first constant heavy domain, number 3 represents the second constant heavy domain and number 4 represents the third constant heavy domain. Number 5 represents the variable light domain and number 6 represents the variable heavy domain. FIG. 4B is a schematic representation of a mAb1 knob (lambda) homodimer. FIG. 4C is a schematic representation of a mAb2 hole (kappa) monomer, where number 7 represents the variable heavy domain, number 8 represents the first constant heavy domain, number 9 represents the second constant heavy domain, and number 10 represents the third constant heavy domain. Number 11 represents the variable light domain and number 12 represents the constant heavy domain. FIG. 4D is a schematic representation of a mAb2 hole (kappa) homodimer. FIG. 4E is a schematic representation of a mAb1 knob homodimer with one CH/LC mispairing. FIG. 4F is a schematic representation of a mAb1 knob homodimer with two CH/LC mispairings. FIG. 4G is a schematic representation of a mAb1 knob homodimer with one CH/LC mispairing. FIG. 4H is a schematic representation of a mAb2 hole homodimer with one CH/LC mispairing. FIG. 4I is a schematic representation of a mAb2 hole homodimer with two CH/LC mispairings. FIG. 4J is a schematic representation of a mAb2 hole homodimer with one CH/LC mispairing. FIG. 4K is a schematic representation of bbmAb1 with one kappa (CH/LC) mispairing. FIG. 4L is a schematic representation of bbmAb1 with one lambda (CH/LC) mispairing. FIG. 4M is a schematic representation of bbmAb1 with two CH/LC mispairings.

DETAILED DESCRIPTION OF THE DISCLOSURE

Figure 1:
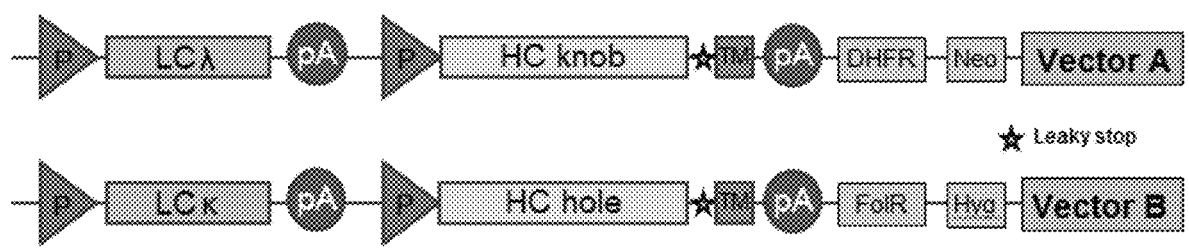
FIG. 1 is a schematic overview of the vector setup according to an embodiment.
Figure 2A:
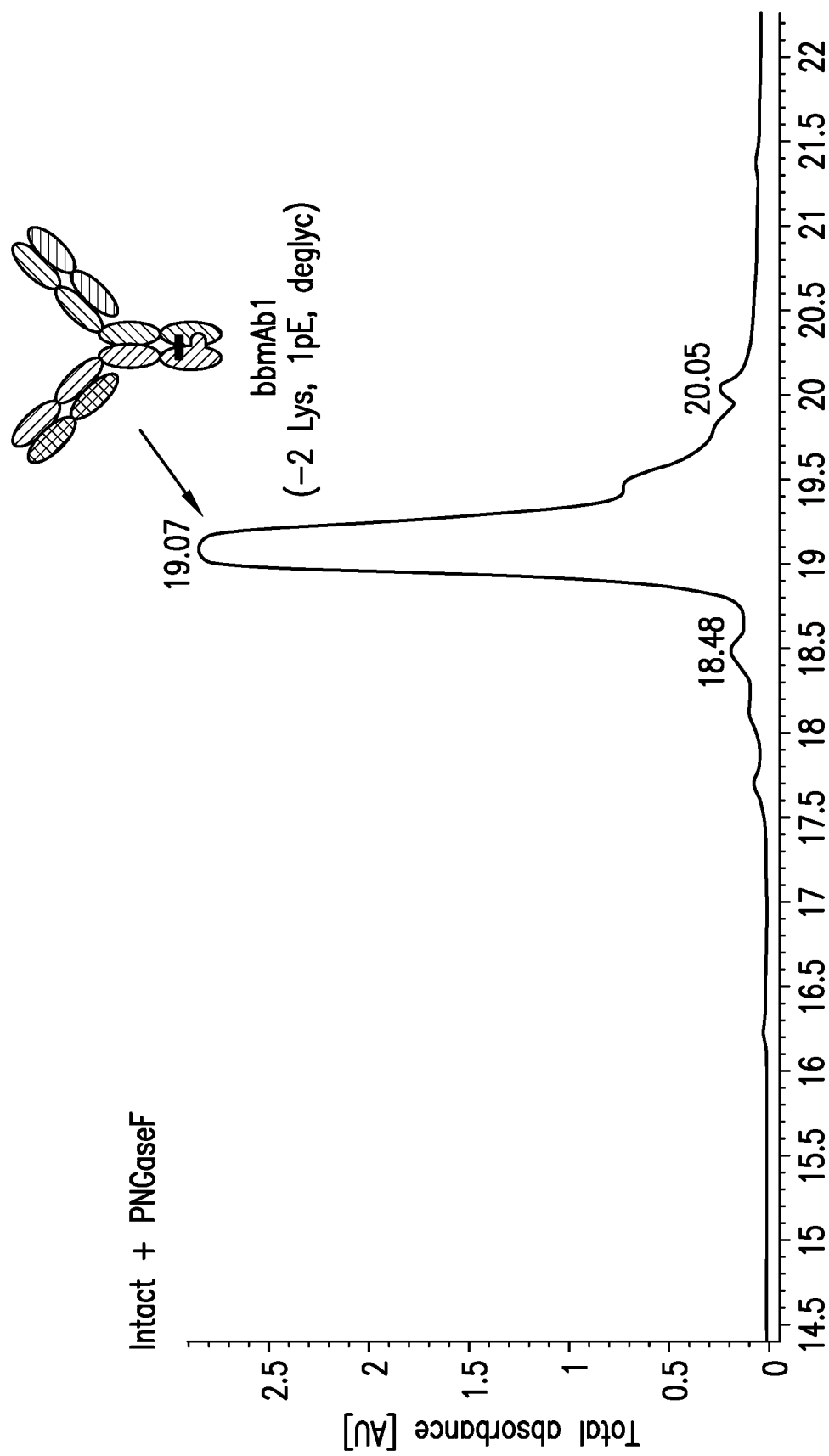
FIG. 2A-2E shows chromatograms according to an embodiment.
Figure 2B:
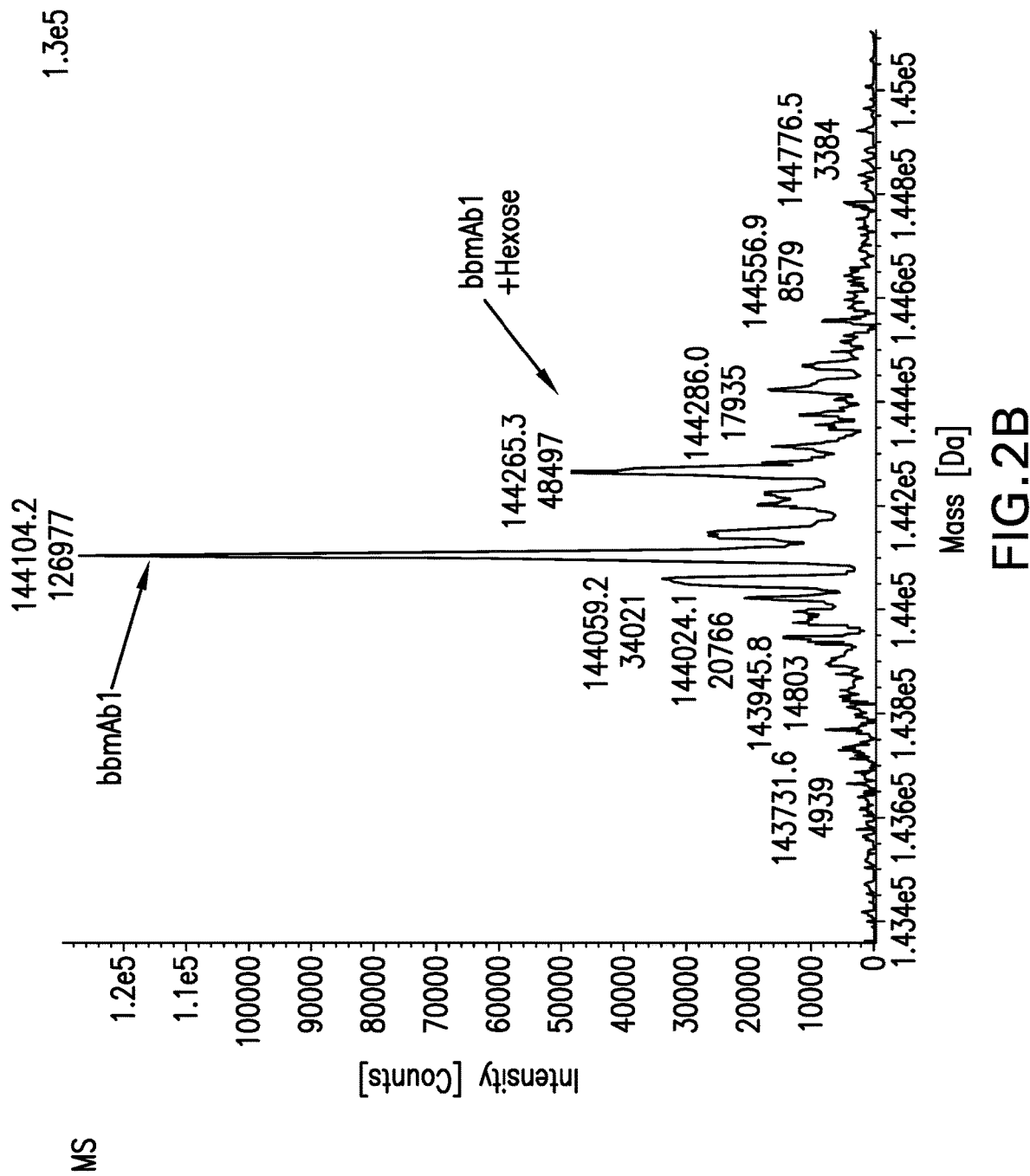
Figure 2C:
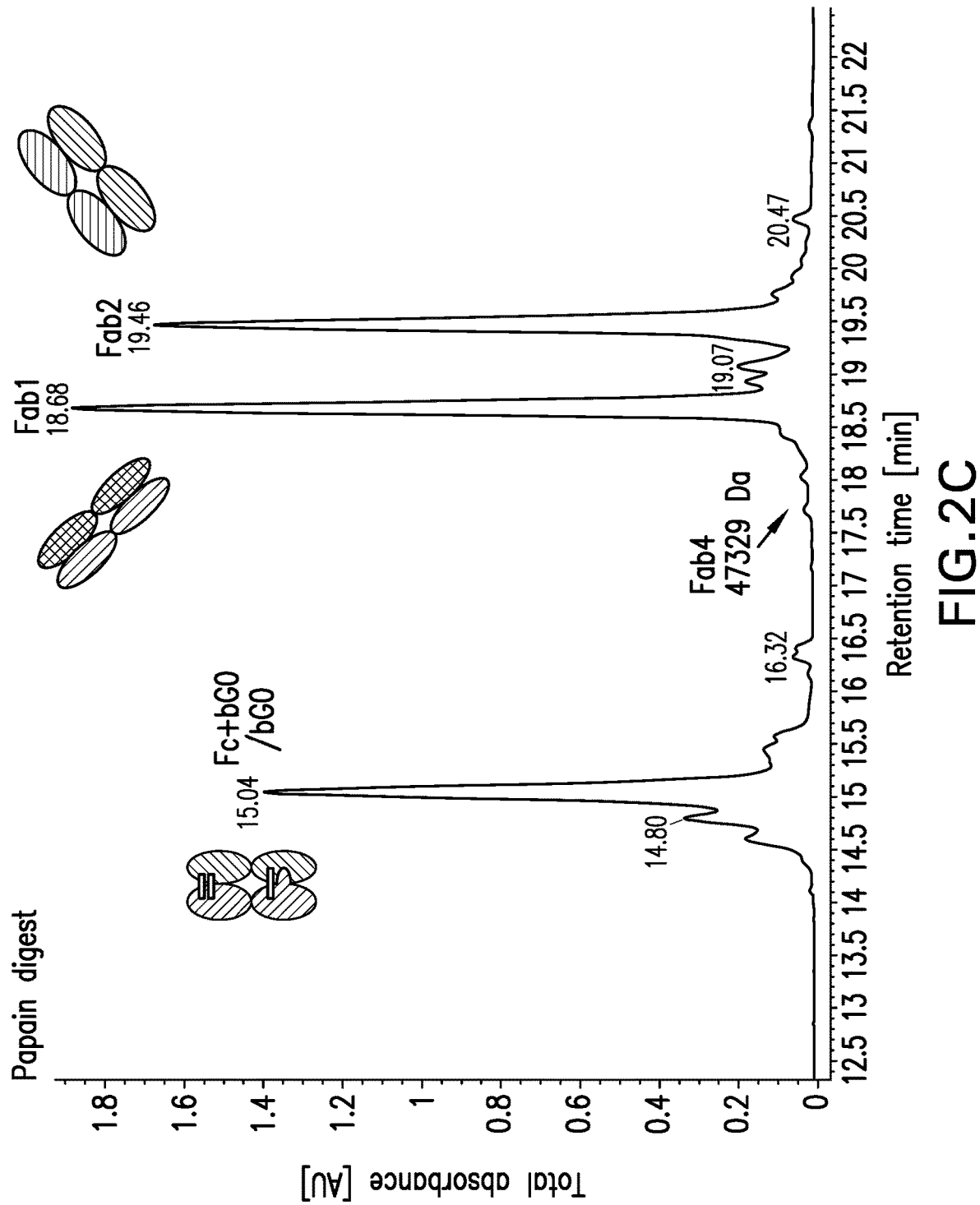
Figure 2D:
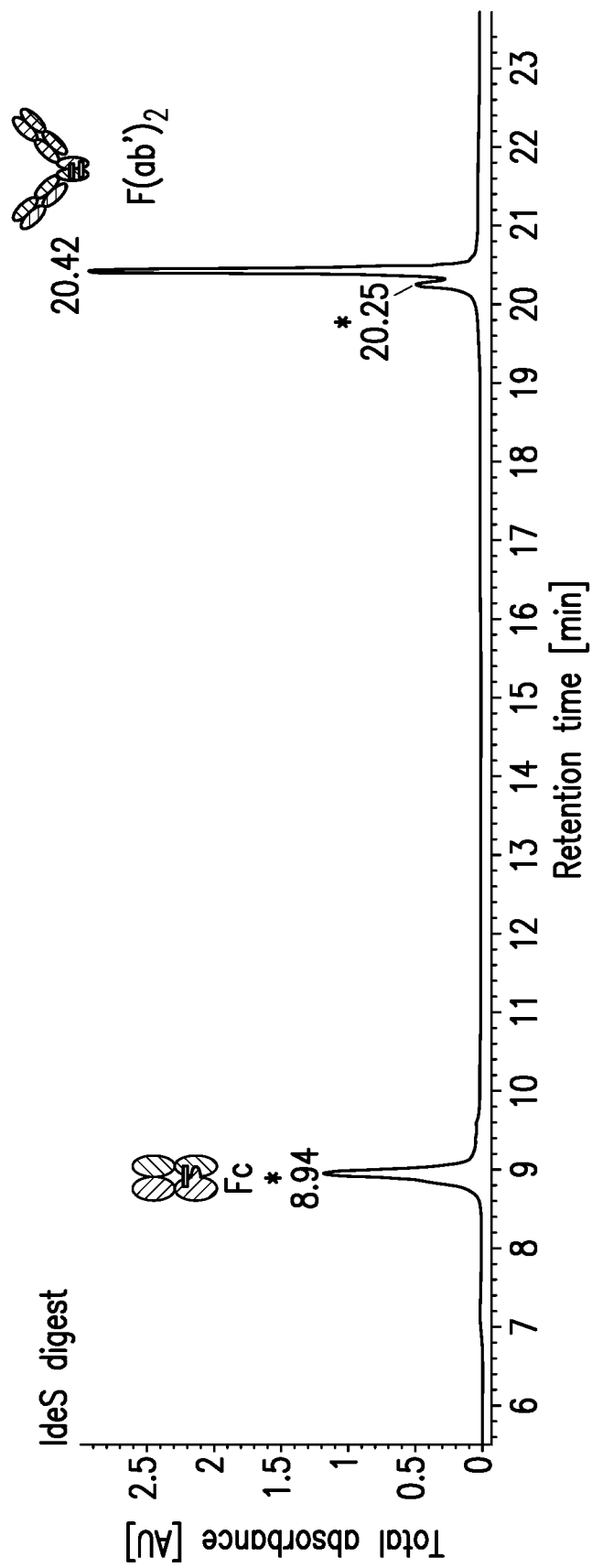
Figure 2E:
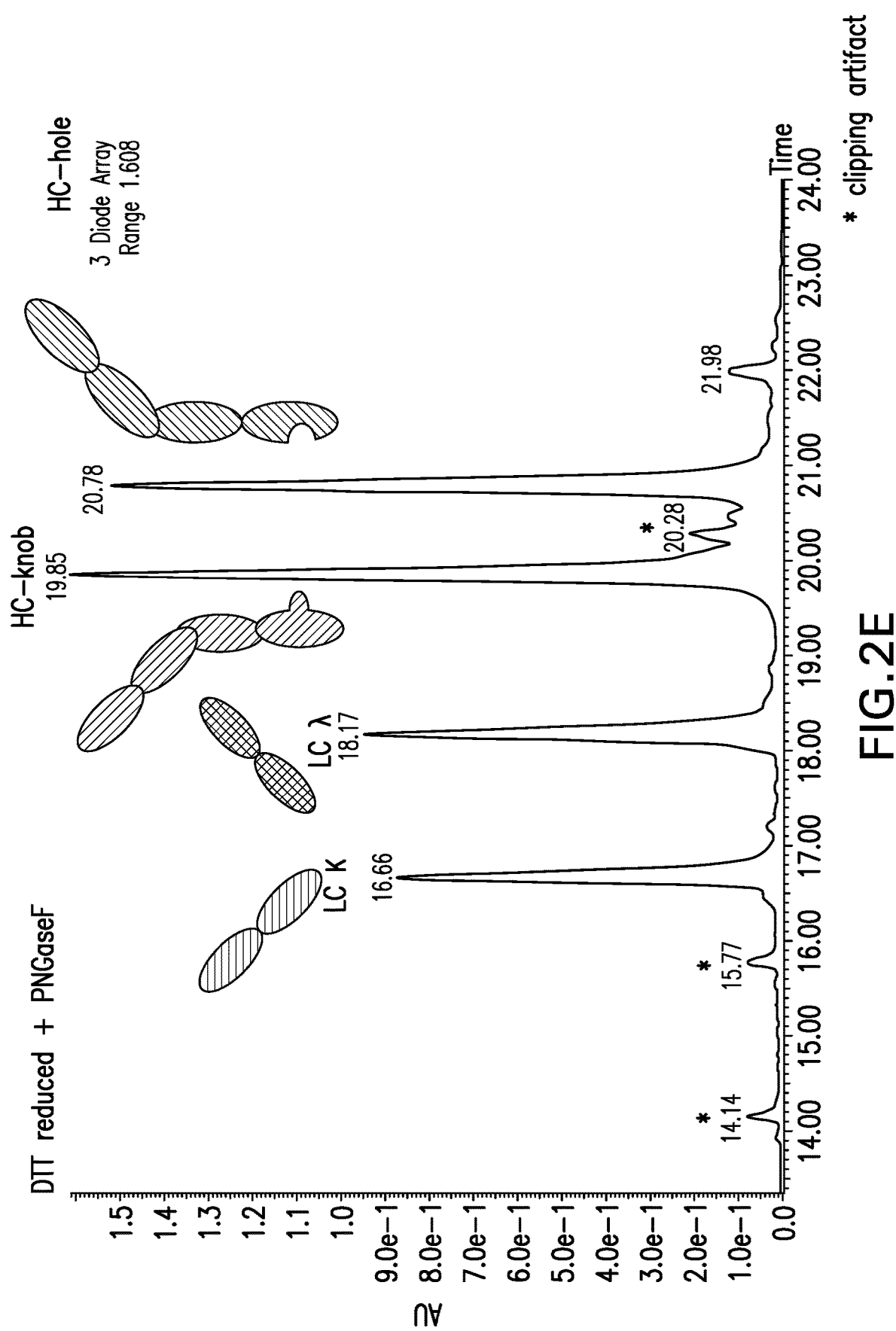

The present disclosure is inter alia based on the unexpected finding that certain antibodies with a light chain of lambda (λ) type are possible to co-express with certain antibodies with a light chain of kappa (κ) type, to form the desired bbmAb.

Without wishing to be bound by theory, the CDRs of each light chain and/or heavy chain could significantly influence which light chain of lambda (λ) type are possible to co-express with certain antibodies with a light chain of kappa (κ) type to successfully obtain the bbmab formed.

The antibodies with a light chain of lambda (λ) type that are possible to co-express with certain antibodies with a light chain of kappa (κ) type, to form the desired bbmAb, in the following also called monospecific binders, can be generated either by use of technologies offering the opportunity to obtain both types of antibodies of either kappa or lambda type antibodies, such as Phage display libraries, e.g. HuUCAL GOLD® or HuCAL PLATINUM® (MorphoSys), or by use of transgenic mice, where the relevant human immunoglobulin sequences have been introduced into the genome of an animal by genetic engineering, e.g. OmniAb antibodies (OMT), Kymouse™ (Kymab), Trianni Mouse™ (Trianni) or AlivaMab Mouse (Ablexis) (reference) can generate kappa or lambda type antibodies. The methods to generate such monospecific binders are well known in the expert field, and are widely applied to generate diverse sets of either kappa or lambda type monospecific binders towards the relevant target of interest. The individual monospecific binders are characterized with respect to relevant biological parameters such as affinity or potency, and also screened for e.g. physicochemical characteristics relevant to judge the so called developability characteristics which are also very well known in the field (e.g. Lorenz et al., American Pharmaceutical Review, August 2014). Monospecific binders showing the best characteristics are finally co-expressed in e.g. CHO cells as described in more detail below. Only combinations are tested by co-expression where a kappa type antibody binding to the first target is combined with a lambda type antibody binding to the second target, and vice versa. The resulting co-expression product and the relevant product related impurities are characterized in detail with the intend to select a combination which results in the best profile, especially the ones which show only a low amount of promiscuous binding of one light chain (e.g. L1, light chain 1, e.g. lambda), towards the wrong heavy chain (e.g. H2, heavy chain 2). An advantage of the method may be that antibody combinations where both light chains exchange the original heavy chain binding partner, which results in a product related impurity of H1L2-H2L1 type, can be deselected. This is advantageous, because such product related impurities are not easy to deplete using state of the art purification processes. The procedure how to co-express the individual antibodies and how to analyze the co-expression product is outlined in more detail below.

Specific antibodies were used as examples, primarily mAb2 binding to IL-1β, with light chain Vκ6 and the mAb1 binding to IL-18, with light chain Vλ1.

In one preferred embodiment, a KiH modification of the Fc-portion of the two antibodies according to Ridgway et al., (1996) was used. Other antibodies were also tested.

As will be shown in the specific examples below, a preferred embodiment bbmAb1 is expressed with a single, common cell line ensuring a sufficient overall yield, purity and product quality required for biologic or diagnostics to proceed with clinical development and commercialization.

1. Definitions

For purposes of interpreting this specification, the following definitions will apply and whenever appropriate, terms used in the singular will also include the plural and vice versa. Additional definitions are set forth throughout the detailed description.

The term "IL-18" is synonym to IL-18 polypeptide, Interleukin-18 polypeptide, IFN-gamma inducing factor or Interferon-gamma-inducing-factor or INF-γ inducing factor. The term "IL-18" refers to human IL-18, unless another species is indicated. IL-18 is well known to a person skilled in the art, and for example obtainable from MBL® International Corporation under product reference #6001-5. Throughout this specification, the term IL-18 encompasses both pro-IL-18 (precursor of mature IL-18 prior protease cleavage) and mature IL-18 (post protease cleavage) interchangeably unless it is specified that the pro- or mature form is meant.

The term "IL-1β" or "IL-1β" is synonym to IL-1βpolypeptide and Interleukin-1β polypeptide. The term "IL-1β" refers to human IL-1β unless another species is indicated. IL-1β is well known to a person skilled in the art, and for example obtainable from Sino Biological under product reference #10139-HNAE-5.

The term "antibody" refers to an intact immunoglobulin or a functional fragment thereof. Naturally occurring antibodies typically comprise a tetramer which is usually composed of at least two heavy (H) chains and at least two light (L) chains. Each heavy chain is comprised of a heavy chain variable region (abbreviated herein as VH) and a heavy chain constant region, usually comprised of three domains (CH1, CH2 ad CH3). Heavy chains can be of any isotype, including IgG (IgG1, IgG2, IgG3 and IgG4 subtypes), IgA (IgA1 and IgA2 subtypes), IgM and IgE. Each light chain is comprised of a light chain variable region (abbreviated herein as VL) and a light chain constant region (CL). Light chain includes kappa (κ) chains and lambda (λ) chains. The heavy and light chain variable region is typically responsible for antigen recognition, whilst the heavy and light chain constant region may mediate the binding of the immunoglobulin to host tissues or factors, including various cells of the immune system (e.g. effector cells) and the first component (Clq) of the classical complement system. The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen.

The term "antigen-binding portion" of an antibody (or simply "antigen portion"), as used herein, refers to full length or one or more fragments of an antibody that retain the ability to specifically bind to IL-18 or IL-1βantigen. It has been shown that the antigen-binding function of an antibody can be performed by fragments of a full-length antibody. Examples of binding fragments encompassed within the term "antigen-binding portion" of an antibody include a Fab fragment, a monovalent fragment consisting of the VL, VH, CL and CH1 domains; a F(ab)2 fragment, a bivalent fragment comprising two Fab fragments linked by a disulfide bridge at the hinge region; a Fd fragment consisting of the VH and CH1 domains; a Fv fragment consisting of the VL and VH domains of a single arm of an antibody; a dAb fragment (Ward et al., (1989) Nature; 341:544-546), which consists of a VH domain; and an isolated complementarity determining region (CDR).

Furthermore, although the two domains of the Fv fragment, VL and VH, are coded for by separate genes, they can be joined, using recombinant methods, by a flexible linker that enables them to be made as a single protein chain in which the VL and VH regions pair to form monovalent molecules (known as single chain Fv (scFv); see e.g. Bird et al., (1988) Science 242:423-426; and Huston et al., (1988) Proc Natl Acad Sc.; 85:5879-5883). Such single chain antibodies are also intended to be encompassed within the term "antigen-binding portion" of an antibody. These antibody fragments are obtained using conventional techniques known to those of skill in the art, and the fragments are screened for utility in the same manner as are intact antibodies.

The term "isolated" means throughout this specification, that the immunoglobulin, antibody or polynucleotide, as the case may be, exists in a physical milieu distinct from that in which it may occur in nature.

Throughout this specification, complementarity determining regions ("CDR") are defined according to the Kabat definition unless specified that the CDR are defined according to another definition. The precise amino acid sequence boundaries of a given CDR can be determined using any of a number of well-known schemes, including those described by Kabat et al. (1991), "Sequences of Proteins of Immunological Interest," 5th Ed. Public Health Service, National Institutes of Health, Bethesda, MD ("Kabat" numbering scheme), Al-Lazikani et al., (1997) JMB 273, 927-948 ("Chothia" numbering scheme) and ImMunoGenTics (IMGT) numbering (Lefranc, M.-P., The Immunologist, 7, 132-136 (1999); Lefranc, M.-P. et al., Dev. Comp. Immunol., 27, 55-77 (2003) ("IMGT" numbering scheme). For example, for classic formats, under Kabat, the CDR amino acid residues in the heavy chain variable domain (VH) are numbered 31-35 (HCDR1), 50-65 (HCDR2), and 95-102 (HCDR3); and the CDR amino acid residues in the light chain variable domain (VL) are numbered 24-34 (LCDR1), 50-56 (LCDR2), and 89-97 (LCDR3). Under Chothia the CDR amino acids in the VH are numbered 26-32 (HCDR1), 52-56 (HCDR2), and 95-102 (HCDR3); and the amino acid residues in VL are numbered 26-32 (LCDR1), 50-52 (LCDR2), and 91-96 (LCDR3). By combining the CDR definitions of both Kabat and Chothia, the CDRs consist of amino acid residues 26-35 (HCDR1), 50-65 (HCDR2), and 95-102 (HCDR3) in human VH and amino acid residues 24-34 (LCDR1), 50-56 (LCDR2), and 89-97 (LCDR3) in human VL. Under IMGT the CDR amino acid residues in the VH are numbered approximately 26-35 (CDR1), 51-57 (CDR2) and 93-102 (CDR3), and the CDR amino acid residues in the VL are numbered approximately 27-32 (CDR1), 50-52 (CDR2), and 89-97 (CDR3) (numbering according to "Kabat"). Under IMGT, the CDR regions of an antibody can be determined using the program IMGT/DomainGap Align.

By convention, the CDR regions in the heavy chain are typically referred to as H-CDR1, H-CDR2 and H-CDR3 and in the light chain as L-CDR1, LCDR2 and L-CDR3. They are numbered sequentially in the direction from the amino terminus to the carboxy terminus. The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody", as used herein, is intended to include antibodies having variable regions in which both the framework and CDR regions are derived from sequences of human origin. Furthermore, if the antibody contains a constant region, the constant region also is derived from such human sequences, e.g. human germline sequences, or mutated versions of human germline sequences or antibody containing consensus framework sequences derived from human framework sequences analysis, for example, as described in Knappik, et al., (2000) J Mol Biol; 296:57-86).

The human antibodies of the invention may include amino acid residues not encoded by human sequences (e.g. mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "human monoclonal antibody" refers to antibodies displaying a single binding specificity which have variable regions in which both the framework and CDR regions are derived from human sequences.

The term "recombinant human antibody", as used herein, includes all human antibodies that are prepared, expressed, created or isolated by recombinant means, such as antibodies isolated from an animal (e.g. a mouse) that is transgenic or transchromosomal for human immunoglobulin genes or a hybridoma prepared therefrom, antibodies isolated from a host cell transformed to express the human antibody, e.g. from a transfectoma, antibodies isolated from a recombinant, combinatorial human antibody library, and antibodies prepared, expressed, created or isolated by any other means that involve splicing of all or a portion of a human immunoglobulin gene. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The phrases "an antibody recognizing an antigen" and "an antibody specific for an antigen" are used interchangeably herein with the term "an antibody which binds specifically to an antigen".

As used herein, a binding molecule that "specifically binds to IL-18" is intended to refer to a binding molecule that binds to human IL-18 with a $K_D$ of a 100 nM or less, 10 nM or less, 1 nM or less.

As used herein, a binding molecule that "specifically binds to IL-1β" is intended to refer to a binding molecule that binds to human IL-1β with a $K_D$ of a 100 nM or less, 10 nM or less, 1 nM or less.

A binding molecule that "cross-reacts with an antigen other than IL-18 is intended to refer to a binding molecule that binds that antigen with a $K_D$ of a 100 nM or less, 10 nM or less, 1 nM or less. A binding molecule that "cross-reacts with an antigen other than IL-1β is intended to refer to a binding molecule that binds that antigen with a $K_D$ of a 100 nM or less, 10 nM or less, 1 nM or less.

A binding molecule that "does not cross-react with a particular antigen" is intended to refer to a binding molecule that exhibits essentially undetectable binding against these proteins in standard binding assays.

As used herein, the term "antagonist" is intended to refer to a binding molecule that inhibits the signalling activity in the presence of activating compound. For example, in the case of IL-18, an IL-18 antagonist would be a binding molecule inhibiting the signalling activity in the presence of IL-18 in a human cell assay such as IL-18 dependent Interferon-gamma (IFN-□) production assay in human blood cells. Examples of an IL-18 dependent IFN-□ production assay in human blood cells are described in more details in the examples below.

The term bivalent bispecific antibody or bivalent bispecific antibodies refer to antibodies binding to two different targets, such as IL-18 and IL-1β.

The bispecific antibodies are "hetero-dimers", which means that one part comes from first antibody, specific for a first target, and another part comes from a second antibody, specific for a second target. A "hetero-dimerization modification" is a modification to one or both parts of the antibodies forming the hetero-dimeric bispecific antibody, intended to facilitate such formation. An example of hetero-dimerization modifications of the Fc domains of two IgG1 parts of antibodies intended to form a bispecific is a "knob" with a bulky amino acid (aa) side chain (S354C, T366W) in the first heavy chain and a "hole" with small aa side chains (Y349C, T366S, L368A, Y407V) were introduced in the second heavy chain as well as an additional disulfide bridge in the CH3 region connecting both heavy chains (Merchant et al., Nat. Biotechnol., 16:677-681 (1998), page 678, table 1).

As used herein, an antibody with "no agonistic activity" is intended to refer to a binding molecule that does not significantly increase target dependent signalling activity in the absence and/or presence of the target in a cell-based assay, such as in case of IL-18, does not significantly increase IL-18 dependent signalling activity in the absence and/or presence of IL-18 human blood cells IFN-γ production assay. Such assays are described in more details in the examples below.

The term "$K_{assoc}$" or "$K_a$", as used herein, is intended to refer to the association rate of a particular binding molecule-antigen interaction, whereas the term "$K_{dis}$" or "$K_d$," as used herein, is intended to refer to the dissociation rate of a particular binding molecule-antigen interaction. The term "$K_D$", as used herein, is intended to refer to the dissociation constant, which is obtained from the ratio of $K_d$ to $K_a$ (i.e. $K_d/K_a$) and is expressed as a molar concentration (M). $K_D$ values for antibodies can be determined using methods well established in the art. A method for determining the $K_D$ of an antibody is by using surface plasmon resonance, such as a Biacore® system.

As used herein, the term "affinity" refers to the strength of interaction between binding molecule and antigen at single antigenic sites.

As used herein, the term "high affinity" for an antibody refers to an antibody having a $K_D$ of 1 nM or less for a target antigen.

As used herein, the term "subject" includes any human or non-human animal.

The term "non-human animal" includes all vertebrates, e.g. mammals and non-mammals, such as non-human primates, sheep, dogs, cats, horses, cows, chickens, amphibians, reptiles, etc.

As used herein, the term, "optimized nucleotide sequence" means that the nucleotide sequence has been altered to encode an amino acid sequence using codons that are preferred in the production cell or organism, generally a eukaryotic cell, for example, a cell of *Pichia pastoris*, a Chinese Hamster Ovary cell (CHO) or a human cell. The optimized nucleotide sequence is engineered to retain completely the amino acid sequence originally encoded by the starting nucleotide sequence, which is also known as the "parental" sequence. The optimized sequences herein have been engineered to have codons that are preferred in CHO mammalian cells; however optimized expression of these sequences in other eukaryotic cells is also envisioned herein.

The term "identity" refers to the similarity between at least two different sequences. This identity can be expressed as a percent identity and determined by standard alignment algorithms, for example, the Basic Local Alignment Tool (BLAST) (Altshul et al., (1990) J Mol Biol; 215:403-410); the algorithm of Needleman et al., (1970) J Mol Biol; 48:444-453 or the algorithm of Meyers et al., (1988) Comput Appl Biosci; 4:11-17). A set of parameters may be the Blosum 62 scoring matrix with a gap penalty of 12, a gap extend penalty of 4, and a frameshift gap penalty of 5. The percent identity between two amino acid or nucleotide sequences can also be determined using the algorithm of E. Meyers and W. Miller, (1989) CABIOS; 4(1):1-17) which has been incorporated into the ALIGN program (version 2.0), using a PAM 120 weight residue table, a gap length penalty of 12 and a gap penalty of 4. The percent identity is usually calculated by comparing sequences of similar length.

The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

A "signal transduction pathway" or "signaling activity" refers to a biochemical causal relationship generally initiated by a protein-protein interaction such as binding of a growth factor to a receptor, resulting in transmission of a signal from one portion of a cell to another portion of a cell. In general, the transmission involves specific phosphorylation of one or more tyrosine, serine, or threonine residues on one or more proteins in the series of reactions causing signal transduction. Penultimate processes typically include nuclear events, resulting in a change in gene expression.

The term "neutralises" and grammatical variations thereof means throughout this specification, that the biological activity of the target is reduced either totally or partially in the presence of the binding protein or antibody, as the case may be.

The term "nucleic acid" or "polynucleotide" refers to deoxyribonucleic acid (DNA) or ribonucleic acid (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994))

The nucleotide in the "polynucleotide" or "nucleic acid" may comprise modifications including base modifications such as bromouridine and inosine derivatives, ribose modification such as phosphorothioate, phosphorodithioate, phosphoroselenoate, phosphorodiselenoate, phosphoroanilothioate, phosphoraniladate and phosphoroamidate.

The term "vector" means any molecule or entity (e.g. nucleic acid, plasmid, bacteriophage or virus) that is suitable for transformation or transfection of a host cell and contains nucleic acid sequences that direct and/or control (in conjunction with the host cell) expression of one or more heterologous coding regions operatively linked thereto.

The term "co-expression" means that different polypeptides are expressed together in a single host cell, common for all the polypeptides. Co-expression of a bispecific antibody means that the different parts forming the functional bispecific antibody are expressed in a single, common, host cell. Co-expression may be achieved by incorporating several expression vectors in the expression host cell, such as one for each of the halves of a bispecific antibody, or by incorporating one expression vector encoding all parts of the bispecific antibody.

The term "mismatched" means that different parts of an intended protein complex, such as a bispecific antibody, do not complex bind as intended, which means that the protein complex does not look or behave as intended. Examples of mismatching in the context of a bispecific antibody are shown in FIG. 4.

A "conservative variant" of a sequence encoding a binding molecule, an antibody or a fragment thereof refers to a sequence comprising conservative amino acid modifications. "Conservative amino acid modifications" are intended to refer to amino acid modifications that do not significantly affect or alter the binding characteristics of the antibody containing the amino acid sequence. Such conservative modifications include amino acid substitutions, additions and deletions. Conservative amino acid substitutions are ones in which the amino acid residue is replaced with an amino acid residue having a similar side chain. Families of amino acid residues having similar side chains have been defined in the art. These families include amino acids with basic side chains (e.g. lysine, arginine, histidine), acidic side chains (e.g. aspartic acid, glutamic acid), uncharged polar side chains (e.g. glycine, asparagine, glutamine, serine, threonine, tyrosine, cysteine, tryptophan), nonpolar side chains (e.g. alanine, valine, leucine, isoleucine, proline, phenylalanine, methionine), beta-branched side chains (e.g. threonine, valine, isoleucine) and aromatic side chains (e.g. tyrosine, phenylalanine, tryptophan, histidine). Modifications can be introduced into a binding protein of the invention by standard techniques known in the art, such as site-directed mutagenesis and PCR-mediated mutagenesis. Conservative amino acid substitution can also encompass non-naturally occurring amino acid residues which are typically incorporated by chemical peptide synthesis rather than by synthesis in biological systems. Non-naturally occurring amino acids include, but are not limited to, peptidomimetic, reversed or inverted forms of amino acid moieties.

The term "epitope" is the part of an antigen that is recognized by the immune system, such as an antibody or a fragment thereof. Within the present specification, the term "epitope" is used interchangeably for both conformational epitopes and linear epitopes. A conformational epitope is composed of discontinuous sections of the antigen's amino acid sequence, whilst a linear epitope is formed by a continuous sequence of amino acids from the antigen.

The term "treat", "treating", "treatment", "prevent", "preventing" or "prevention" includes therapeutic treatments, prophylactic treatments and applications in which one reduces the risk that a subject will develop a disorder or other risk factor. Treatment does not require the complete curing of a disorder and encompasses the reduction of the symptoms or underlying risk factors. As used herein, a human antibody or a fragment thereof comprises heavy or light chain variable regions or full length heavy or light chains that are "the product of" or "derived from" a particular germline sequence if the variable regions or full length chains of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody or fragment thereof that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody. A human antibody that is "the product of" or "derived from" a particular human germline immunoglobulin sequence may contain amino acid differences as compared to the germline sequence, due to, for example, naturally occurring somatic mutations or intentional introduction of site-directed mutation. However, a selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g. murine germline sequences). In certain cases, a human antibody may be at least 60%, 70%, 80%, 90%, or at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

Human antibodies may be produced by a number of methods known to those of skill in the art. Human antibodies can be made by the hybridoma method using human myeloma or mouse-human heteromyeloma cells lines (Kozbor, J Immunol; (1984) 133:3001; Brodeur, Monoclonal Isolated Antibody Production Techniques and Applications, pp 51-63, Marcel Dekker Inc, 1987). Alternative methods include the use of phage libraries or transgenic mice both of which utilize human variable region repertories (Winter G; (1994) Annu Rev Immunol 12:433-455, Green L L, (1999) J Immunol Methods 231:11-23).

Several strains of transgenic mice are now available wherein their mouse immunoglobulin loci has been replaced with human immunoglobulin gene segments (Tomizuka K, (2000) Proc Natl Acad Sci, 97:722-727; Fishwild D M (1996) Nature Biotechnol 14:845-851; Mendez M J, (1997) Nature Genetics 15:146-156). Upon antigen challenge such mice are capable of producing a repertoire of human antibodies from which antibodies of interest can be selected. Of particular note is the Trimera™ system (Eren R et al, (1988) Immunology 93:154-161) where human lymphocytes are transplanted into irradiated mice, the Selected Lymphocyte Isolated antibody System (SLAM, Babcook et al, Proc Natl Acad Sci (1996) 93:7843-7848) where human (or other species) lymphocytes are effectively put through a massive pooled in vitro isolated antibody generation procedure followed by deconvoluted, limiting dilution and selection procedure and the Xenomouse™ (Abgenix Inc). An alternative approach is available from Morphotek Inc using the Morphodoma™ technology.

Phage display technology can be used to produce human antibodies and fragments thereof, (McCafferty; (1990) Nature, 348:552-553 and Griffiths A D et al (1994) EMBO 13:3245-3260). According to this technique, isolated antibody variable domain genes are cloned in frame into either a major or minor coat of protein gene of a filamentous bacteriophage such as M13 or fd and displayed (usually with the aid of a helper phage) as function isolated antibody fragments on the surface of the phage particle. Selections based on the function properties of the isolated antibody result in selection of the gene encoding the isolated antibody exhibiting these properties. The phage display technique can be used to select antigen specific antibodies from libraries made from human B cells taken from individuals afflicted with a disease or disorder or alternatively from unimmunized human donors (Marks; J Mol Bio (1991) 222:581-591). Where an intact human isolated antibody is desired comprising an Fc domain it is necessary reclone the phage displayed derived fragment into a mammalian expression vectors comprising the desired constant regions and establishing stable expressing cell lines.

The technique of affinity maturation (Marks; Biotechnol (1992) 10:779-783) may be used to provide binding affinity wherein the affinity of the primary human isolated antibody is improved by sequentially replacing the H and L chain variable regions with naturally occurring variants and selecting on the basis of improved binding affinities. Variants of this technique such as 'epitope imprinting' are now also available (WO 93/06213; Waterhouse; Nucl Acids Res (1993) 21:2265-2266).

The term "pure" when used in the context of purified bispecific antibody relates to purity and identity of different bispecific antibody combinations and constructs after co-expression in selected cells under conditions wherein the cells express the bispecific antibody and after protein-A purification using an intact UPLC-MS mass screening approach. Pure or purity refers to the relative quantify of the formed hetero- and homodimer bbmAbs. Using the method of the invention correctly formed heterodimeric bbmAb1 and bbmAb2 could be observed with a relative purity of over 85% based on intact mass signal intensity.

2. IL-18 Antibody

Particularly preferred IL-18 antibodies or antigen-binding fragments thereof used in the disclosed methods are human antibodies.

For ease of reference, the amino acid sequences of the hypervariable regions of a specific IL-18 antibody, called mAb1, based on the Kabat definition and the Chothia definition, as well as the $V_L$ and $V_H$ domains and full heavy and light chains are provided in Table 1, below.

TABLE 1

Amino acid sequences of the hypervariable regions (CDRs), variable domains (VH and VL) and full chains of mAb1. The DNA encoding the VL of mAb1 is set forth in SEQ ID NO: 18. The DNA encoding the VH of mAb1 is set forth in SEQ ID NO: 8.

| mAb1 heavy chain | | |
|---|---|---|
| CDR1 | Kabat | SEQ ID NO: 1 |
| | Chothia | SEQ ID NO: 4 |
| CDR2 | Kabat | SEQ ID NO: 2 |
| | Chothia | SEQ ID NO: 5 |
| CDR3 | Kabat | SEQ ID NO: 3 |
| | Chothia | SEQ ID NO: 6 |
| VH | | SEQ ID NO: 7 |
| Heavy Chain | | SEQ ID NO: 9 |
| mAb1 light chain | | |
| CDR1 | Kabat | SEQ ID NO: 11 |
| | Chothia | SEQ ID NO: 14 |
| CDR2 | Kabat | SEQ ID NO: 12 |
| | Chothia | SEQ ID NO: 15 |
| CDR3 | Kabat | SEQ ID NO: 13 |
| | Chothia | SEQ ID NO: 16 |
| VL | | SEQ ID NO: 17 |
| Light Chain | | SEQ ID NO: 19 |

In one embodiment, the IL-18 antibody or antigen-binding fragment thereof comprises at least one immunoglobulin heavy chain variable domain ($V_H$) comprising hypervariable regions CDR1, CDR2 and CDR3, said CDR1 having the amino acid sequence SEQ ID NO:1, said CDR2 having the amino acid sequence SEQ ID NO:2, and said CDR3 having the amino acid sequence SEQ ID NO:3. In one embodiment, the IL-18 antibody or antigen-binding fragment thereof comprises at least one immunoglobulin heavy chain variable domain ($V_H$) comprising hypervariable regions CDR1, CDR2 and CDR3, said CDR1 having the amino acid sequence SEQ ID NO:4, said CDR2 having the amino acid sequence SEQ ID NO:5, and said CDR3 having the amino acid sequence SEQ ID NO:6.

In one embodiment, the IL-18 antibody or antigen-binding fragment thereof comprises at least one immunoglobulin light chain variable domain ($V_L$) comprising hypervariable regions CDR1, CDR2 and CDR3, said CDR1 having the amino acid sequence SEQ ID NO:11, said CDR2 having the amino acid sequence SEQ ID NO:12 and said CDR3 having the amino acid sequence SEQ ID NO:13. In one embodiment, the IL-18 antibody or antigen-binding fragment thereof comprises at least one immunoglobulin light chain variable domain ($V_L$) comprising hypervariable regions CDR1, CDR2 and CDR3, said CDR1 having the amino acid sequence SEQ ID NO:14, said CDR2 having the amino acid sequence SEQ ID NO:15 and said CDR3 having the amino acid sequence SEQ ID NO:16.

In one embodiment, the IL-18 antibody or antigen-binding fragment thereof comprises at least one immunoglobulin $V_H$ domain and at least one immunoglobulin $V_L$ domain, wherein: a) the immunoglobulin $V_H$ domain comprises (e.g. in sequence): i) hypervariable regions CDR1, CDR2 and CDR3, said CDR1 having the amino acid sequence SEQ ID NO:1, said CDR2 having the amino acid sequence SEQ ID NO:2, and said CDR3 having the amino acid sequence SEQ ID NO:3; or ii) hypervariable regions CDR1, CDR2 and CDR3, said CDR1 having the amino acid sequence SEQ ID NO:4, said CDR2 having the amino acid sequence SEQ ID NO:5, and said CDR3 having the amino acid sequence SEQ ID NO:6; and b) the immunoglobulin $V_L$ domain comprises (e.g. in sequence): i) hypervariable regions CDR1, CDR2 and CDR3, said CDR1 having the amino acid sequence SEQ ID NO:11, said CDR2 having the amino acid sequence SEQ ID NO:12, and said CDR3 having the amino acid sequence SEQ ID NO:13 or ii) hypervariable regions CDR1, CDR2 and CDR3, said CDR1 having the amino acid sequence SEQ ID NO:14, said CDR2 having the amino acid sequence SEQ ID NO:15, and said CDR3 having the amino acid sequence SEQ ID NO:16.

In one embodiment, the IL-18 antibody or antigen-binding fragment thereof comprises: a) an immunoglobulin heavy chain variable domain ($V_H$) comprising the amino acid sequence set forth as SEQ ID NO:7; b) an immunoglobulin light chain variable domain ($V_L$) comprising the amino acid sequence set forth as SEQ ID NO:17; c) an immunoglobulin $V_H$ domain comprising the amino acid sequence set forth as SEQ ID NO:7 and an immunoglobulin $V_L$ domain comprising the amino acid sequence set forth as SEQ ID NO:17; d) an immunoglobulin $V_H$ domain comprising the hypervariable regions set forth as SEQ ID NO:1, SEQ ID NO:2, and SEQ ID NO:3; e) an immunoglobulin $V_L$ domain comprising the hypervariable regions set forth as SEQ ID NO:11, SEQ ID NO:12 and SEQ ID NO:13; f) an immunoglobulin $V_H$ domain comprising the hypervariable regions set forth as SEQ ID NO:4, SEQ ID NO:5 and SEQ ID NO:6; g) an immunoglobulin $V_L$ domain comprising the hypervariable regions set forth as SEQ ID NO:14, SEQ ID NO:15 and SEQ ID NO:16; h) an immunoglobulin $V_H$ domain comprising the hypervariable regions set forth as SEQ ID NO:1, SEQ ID NO:2, and SEQ ID NO:3 and an immunoglobulin $V_L$ domain comprising the hypervariable regions set forth as SEQ ID NO:11, SEQ ID NO:12 and SEQ ID NO:13; i) an immunoglobulin $V_H$ domain comprising the hypervariable regions set forth as SEQ ID NO:4, SEQ ID NO:5, and SEQ ID NO:6 and an immunoglobulin $V_L$ domain comprising the hypervariable regions set forth as SEQ ID NO:14, SEQ ID NO:15 and SEQ ID NO:16; j) a light chain comprising SEQ ID NO:19; k) a heavy chain comprising SEQ ID NO:9; or l) a light chain comprising SEQ ID NO:19 and a heavy chain comprising SEQ ID NO:9.

In some embodiments, the IL-18 antibody or antigen-binding fragment thereof (e.g. mAb1) comprises the three CDRs of SEQ ID NO:7. In other embodiments, the IL-18 antibody or antigen-binding fragment thereof comprises the three CDRs of SEQ ID NO:17. In other embodiments, the IL-18 antibody or antigen-binding fragment thereof comprises the three CDRs of SEQ ID NO:7 and the three CDRs of SEQ ID NO:17. In some embodiments, the IL-18 antibody or antigen-binding fragment thereof comprises the three CDRs of SEQ ID NO:9. In other embodiments, IL-18 antibody or antigen-binding fragment thereof comprises the three CDRs of SEQ ID NO:19. In other embodiments, the IL-18 antibody or antigen-binding fragment thereof comprises the three CDRs of SEQ ID NO:9 and the three CDRs of SEQ ID NO:19.

In one embodiment, the IL-18 antibody or antigen-binding fragment thereof (e.g. mAb1) is selected from a human IL-18 antibody that comprises at least: a) an immunoglobulin heavy chain or fragment thereof which comprises a variable domain comprising, in sequence, the hypervariable regions CDR1, CDR2 and CDR3 and the constant part or fragment thereof of a human heavy chain; said CDR1 having the amino acid sequence SEQ ID NO:1, said CDR2 having the amino acid sequence SEQ ID NO:2, and said CDR3 having the amino acid sequence SEQ ID NO:3; and b) an immunoglobulin light chain or fragment thereof which comprises a variable domain comprising, in sequence, the hypervariable regions CDR1, CDR2, and CDR3 and the constant part or fragment thereof of a human light chain, said CDR1 having the amino acid sequence SEQ ID NO:11, said CDR2 having the amino acid sequence SEQ ID NO:12, and said CDR3 having the amino acid sequence SEQ ID NO:13.

In one embodiment, the IL-18 antibody or antigen-binding fragment thereof (e.g. mAb1) is selected from a human IL-18 antibody that comprises at least: a) an immunoglobulin heavy chain or fragment thereof which comprises a variable domain comprising, in sequence, the hypervariable regions CDR1, CDR2 and CDR3 and the constant part or fragment thereof of a human heavy chain; said CDR1 having the amino acid sequence SEQ ID NO:4, said CDR2 having the amino acid sequence SEQ ID NO:5 and said CDR3 having the amino acid sequence SEQ ID NO:6; and b) an immunoglobulin light chain or fragment thereof which comprises a variable domain comprising, in sequence, the hypervariable regions CDR1, CDR2, and CDR3 and the constant part or fragment thereof of a human light chain, said CDR1 having the amino acid sequence SEQ ID NO:14, said CDR2 having the amino acid sequence SEQ ID NO:15, and said CDR3 having the amino acid sequence SEQ ID NO:16.

In one embodiment, the IL-18 antibody or antigen-binding fragment thereof is selected from a single chain antibody or antigen-binding fragment thereof that comprises an antigen-binding site comprising: a) a first domain comprising, in sequence, the hypervariable regions CDR1, CDR2 and CDR3, said CDR1 having the amino acid sequence SEQ ID NO:1, said CDR2 having the amino acid sequence SEQ ID NO:2, and said CDR3 having the amino acid sequence SEQ ID NO:3; and b) a second domain comprising, in sequence, the hypervariable regions CDR1, CDR2 and CDR3, said CDR1 having the amino acid sequence SEQ ID NO:11, said CDR2 having the amino acid sequence SEQ ID NO:12, and said CDR3 having the amino acid sequence SEQ ID NO:13; and c) a peptide linker which is bound either to the N-terminal extremity of the first domain and to the C-terminal extremity of the second domain or to the C-terminal extremity of the first domain and to the N-terminal extremity of the second domain.

In one embodiment, the IL-18 antibody or antigen-binding fragment thereof (e.g. mAb1) is selected from a single chain antibody or antigen-binding fragment thereof that comprises an antigen-binding site comprising: a) a first domain comprising, in sequence, the hypervariable regions CDR1, CDR2 and CDR3, said CDR1 having the amino acid sequence SEQ ID NO:4, said CDR2 having the amino acid sequence SEQ ID NO:5, and said CDR3 having the amino acid sequence SEQ ID NO:6; and b) a second domain comprising, in sequence, the hypervariable regions CDR1, CDR2 and CDR3, said CDR1 having the amino acid sequence SEQ ID NO:14, said CDR2 having the amino acid sequence SEQ ID NO:15, and said CDR3 having the amino acid sequence SEQ ID NO:16; and c) a peptide linker which is bound either to the N-terminal extremity of the first domain and to the C-terminal extremity of the second domain or to the C-terminal extremity of the first domain and to the N-terminal extremity of the second domain.

The $V_H$ or $V_L$ domain of an IL-18 antibody or antigen-binding fragment thereof used in the disclosed methods may have $V_H$ and/or $V_L$ domains that are substantially identical to the $V_H$ or $V_L$ domains set forth in SEQ ID NO:7 and 17. A human IL-18 antibody disclosed herein may comprise a heavy chain that is substantially identical to that set forth as SEQ ID NO:9 and/or a light chain that is substantially identical to that set forth as SEQ ID NO:19. A human IL-18 antibody disclosed herein may comprise a heavy chain that comprises SEQ ID NO:9 and a light chain that comprises SEQ ID NO:19. A human IL-18 antibody disclosed herein may comprise: a) one heavy chain, comprising a variable domain having an amino acid sequence substantially identical to that shown in SEQ ID NO:7 and the constant part of a human heavy chain; and b) one light chain, comprising a variable domain having an amino acid sequence substantially identical to that shown in SEQ ID NO:17 and the constant part of a human light chain.

Other preferred IL-18 antagonists (e.g. antibodies) for use in the disclosed methods, kits and regimens are those set forth in U.S. Pat. No. 9,376,489, which is incorporated by reference herein in its entirety.

3. IL-1β Antibody

Particularly preferred IL-1β antibodies or antigen-binding fragments thereof used in the disclosed methods are human antibodies.

For ease of reference, the amino acid sequences of the hypervariable regions of a specific IL-1β antibody, called mAb2, based on the Kabat definition and the Chothia definition, as well as the $V_L$ and $V_H$ domains and full heavy and light chains are provided in Table 2, below.

TABLE 2

Amino acid sequences of the hypervariable regions (CDRs), variable domains (VH and VL) and full chains of mAb2. The DNA encoding the VL of mAb2 is set forth in SEQ ID NO: 38. The DNA encoding the VH of mAb2 is set forth in SEQ ID NO: 27.

| mAb2 heavy chain | | |
|---|---|---|
| CDR1 | Kabat | SEQ ID NO: 21 |
|  | Chothia | SEQ ID NO: 24 |
| CDR2 | Kabat | SEQ ID NO: 22 |
|  | Chothia | SEQ ID NO: 25 |

TABLE 2-continued

Amino acid sequences of the hypervariable regions (CDRs), variable domains (VH and VL) and full chains of mAb2. The DNA encoding the VL of mAb2 is set forth in SEQ ID NO: 38. The DNA encoding the VH of mAb2 is set forth in SEQ ID NO: 27.

| CDR3 | Kabat | SEQ ID NO: 23 |
|---|---|---|
|  | Chothia | SEQ ID NO: 26 |
| VH |  | SEQ ID NO: 27 |
| Heavy Chain |  | SEQ ID NO: 29 |
| mAb2 light chain | | |
| CDR1 | Kabat | SEQ ID NO: 31 |
|  | Chothia | SEQ ID NO: 34 |
| CDR2 | Kabat | SEQ ID NO: 32 |
|  | Chothia | SEQ ID NO: 35 |
| CDR3 | Kabat | SEQ ID NO: 33 |
|  | Chothia | SEQ ID NO: 36 |
| VL |  | SEQ ID NO: 37 |
| Light Chain |  | SEQ ID NO: 39 |

In one embodiment, the IL-1β antibody or antigen-binding fragment thereof comprises at least one immunoglobulin heavy chain variable domain ($V_H$) comprising hypervariable regions CDR1, CDR2 and CDR3, said CDR1 having the amino acid sequence SEQ ID NO:21, said CDR2 having the amino acid sequence SEQ ID NO:22, and said CDR3 having the amino acid sequence SEQ ID NO:23. In one embodiment, the IL-1β antibody or antigen-binding fragment thereof comprises at least one immunoglobulin heavy chain variable domain ($V_H$) comprising hypervariable regions CDR1, CDR2 and CDR3, said CDR1 having the amino acid sequence SEQ ID NO:24, said CDR2 having the amino acid sequence SEQ ID NO:25, and said CDR3 having the amino acid sequence SEQ ID NO:26.

In one embodiment, the IL-1β antibody or antigen-binding fragment thereof comprises at least one immunoglobulin light chain variable domain ($V_L$) comprising hypervariable regions CDR1, CDR2 and CDR3, said CDR1 having the amino acid sequence SEQ ID NO:31, said CDR2 having the amino acid sequence SEQ ID NO:32 and said CDR3 having the amino acid sequence SEQ ID NO:33. In one embodiment, the IL-1β antibody or antigen-binding fragment thereof comprises at least one immunoglobulin light chain variable domain ($V_L$) comprising hypervariable regions CDR1, CDR2 and CDR3, said CDR1 having the amino acid sequence SEQ ID NO:34, said CDR2 having the amino acid sequence SEQ ID NO:35, and said CDR3 having the amino acid sequence SEQ ID NO:36.

In one embodiment, the IL-1β antibody or antigen-binding fragment thereof comprises at least one immunoglobulin $V_H$ domain and at least one immunoglobulin $V_L$ domain, wherein: a) the immunoglobulin $V_H$ domain comprises (e.g. in sequence): i) hypervariable regions CDR1, CDR2 and CDR3, said CDR1 having the amino acid sequence SEQ ID NO:21, said CDR2 having the amino acid sequence SEQ ID NO:22, and said CDR3 having the amino acid sequence SEQ ID NO:23; or ii) hypervariable regions CDR1, CDR2 and CDR3, said CDR1 having the amino acid sequence SEQ ID NO:24, said CDR2 having the amino acid sequence SEQ ID NO:25, and said CDR3 having the amino acid sequence SEQ ID NO:26; and b) the immunoglobulin $V_L$ domain comprises (e.g. in sequence): i) hypervariable regions CDR1, CDR2 and CDR3, said CDR1 having the amino acid sequence SEQ ID NO:31, said CDR2 having the amino acid sequence SEQ ID NO:32, and said CDR3 having the amino acid sequence SEQ ID NO:33 or ii) hypervariable regions CDR1, CDR2 and CDR3, said CDR1 having the amino acid sequence SEQ ID NO:34, said CDR2 having the amino acid sequence SEQ ID NO:35, and said CDR3 having the amino acid sequence SEQ ID NO:36.

In one embodiment, the IL-1β antibody or antigen-binding fragment thereof comprises: a) an immunoglobulin heavy chain variable domain ($V_H$) comprising the amino acid sequence set forth as SEQ ID NO:27; b) an immunoglobulin light chain variable domain ($V_L$) comprising the amino acid sequence set forth as SEQ ID NO:37; c) an immunoglobulin $V_H$ domain comprising the amino acid sequence set forth as SEQ ID NO:27 and an immunoglobulin $V_L$ domain comprising the amino acid sequence set forth as SEQ ID NO:37; d) an immunoglobulin $V_H$ domain comprising the hypervariable regions set forth as SEQ ID NO:21, SEQ ID NO:22, and SEQ ID NO:23; e) an immunoglobulin $V_L$ domain comprising the hypervariable regions set forth as SEQ ID NO:31, SEQ ID NO:32 and SEQ ID NO:33; f) an immunoglobulin $V_H$ domain comprising the hypervariable regions set forth as SEQ ID NO:24, SEQ ID NO:25 and SEQ ID NO:26; g) an immunoglobulin $V_L$ domain comprising the hypervariable regions set forth as SEQ ID NO:34, SEQ ID NO:35 and SEQ ID NO:36; h) an immunoglobulin $V_H$ domain comprising the hypervariable regions set forth as SEQ ID NO:21, SEQ ID NO:22, and SEQ ID NO:23 and an immunoglobulin $V_L$ domain comprising the hypervariable regions set forth as SEQ ID NO:31, SEQ ID NO:32 and SEQ ID NO:33; i) an immunoglobulin $V_H$ domain comprising the hypervariable regions set forth as SEQ ID NO:24, SEQ ID NO:25, and SEQ ID NO:26 and an immunoglobulin $V_L$ domain comprising the hypervariable regions set forth as SEQ ID NO:34, SEQ ID NO:35, and SEQ ID NO:36; j) a light chain comprising SEQ ID NO:37; k) a heavy chain comprising SEQ ID NO:29; or l) a light chain comprising SEQ ID NO:39 and a heavy chain comprising SEQ ID NO:29.

In some embodiments, the IL-1β antibody or antigen-binding fragment thereof (e.g. mAb2) comprises the three CDRs of SEQ ID NO:37. In other embodiments, the IL-1β antibody or antigen-binding fragment thereof comprises the three CDRs of SEQ ID NO:27. In other embodiments, the IL-1β antibody or antigen-binding fragment thereof comprises the three CDRs of SEQ ID NO:37 and the three CDRs of SEQ ID NO:27. In some embodiments, the IL-1β antibody or antigen-binding fragment thereof comprises the three CDRs of SEQ ID NO:39. In other embodiments, IL-1β antibody or antigen-binding fragment thereof comprises the three CDRs of SEQ ID NO:29. In other embodiments, the IL-1β antibody or antigen-binding fragment thereof comprises the three CDRs of SEQ ID NO:39 and the three CDRs of SEQ ID NO:29.

In one embodiment, the IL-1β antibody or antigen-binding fragment thereof (e.g. mAb2) is selected from a human IL-1β antibody that comprises at least: a) an immunoglobulin heavy chain or fragment thereof which comprises a variable domain comprising, in sequence, the hypervariable regions CDR1, CDR2 and CDR3 and the constant part or fragment thereof of a human heavy chain; said CDR1 having the amino acid sequence SEQ ID NO:21, said CDR2 having the amino acid sequence SEQ ID NO:22, and said CDR3 having the amino acid sequence SEQ ID NO:23; and b) an immunoglobulin light chain or fragment thereof which comprises a variable domain comprising, in sequence, the hypervariable regions CDR1, CDR2, and CDR3 and the constant part or fragment thereof of a human light chain, said CDR1 having the amino acid sequence SEQ ID NO:31, said CDR2 having the amino acid sequence SEQ ID NO:32, and said CDR3 having the amino acid sequence SEQ ID NO:33.

In one embodiment, the IL-1β antibody or antigen-binding fragment thereof (e.g. mAb2) is selected from a human IL-1β antibody that comprises at least: a) an immunoglobulin heavy chain or fragment thereof which comprises a variable domain comprising, in sequence, the hypervariable regions CDR1, CDR2 and CDR3 and the constant part or fragment thereof of a human heavy chain; said CDR1 having the amino acid sequence SEQ ID NO:24, said CDR2 having the amino acid sequence SEQ ID NO:25 and said CDR3 having the amino acid sequence SEQ ID NO:26; and b) an immunoglobulin light chain or fragment thereof which comprises a variable domain comprising, in sequence, the hypervariable regions CDR1, CDR2, and CDR3 and the constant part or fragment thereof of a human light chain, said CDR1 having the amino acid sequence SEQ ID NO:34, said CDR2 having the amino acid sequence SEQ ID NO:35, and said CDR3 having the amino acid sequence SEQ ID NO:36.

In one embodiment, the IL-1β antibody or antigen-binding fragment thereof is selected from a single chain antibody or antigen-binding fragment thereof that comprises an antigen-binding site comprising: a) a first domain comprising, in sequence, the hypervariable regions CDR1, CDR2 and CDR3, said CDR1 having the amino acid sequence SEQ ID NO:21, said CDR2 having the amino acid sequence SEQ ID NO:22, and said CDR3 having the amino acid sequence SEQ ID NO:23; and b) a second domain comprising, in sequence, the hypervariable regions CDR1, CDR2 and CDR3, said CDR1 having the amino acid sequence SEQ ID NO:31, said CDR2 having the amino acid sequence SEQ ID NO:32, and said CDR3 having the amino acid sequence SEQ ID NO:33; and c) a peptide linker which is bound either to the N-terminal extremity of the first domain and to the C-terminal extremity of the second domain or to the C-terminal extremity of the first domain and to the N-terminal extremity of the second domain.

In one embodiment, the IL-1β antibody or antigen-binding fragment thereof (e.g. mAb2) is selected from a single chain antibody or antigen-binding fragment thereof that comprises an antigen-binding site comprising: a) a first domain comprising, in sequence, the hypervariable regions CDR1, CDR2 and CDR3, said CDR1 having the amino acid sequence SEQ ID NO:24, said CDR2 having the amino acid sequence SEQ ID NO:25, and said CDR3 having the amino acid sequence SEQ ID NO:26; and b) a second domain comprising, in sequence, the hypervariable regions CDR1, CDR2 and CDR3, said CDR1 having the amino acid sequence SEQ ID NO:34, said CDR2 having the amino acid sequence SEQ ID NO:35, and said CDR3 having the amino acid sequence SEQ ID NO:36; and c) a peptide linker which is bound either to the N-terminal extremity of the first domain and to the C-terminal extremity of the second domain or to the C-terminal extremity of the first domain and to the N-terminal extremity of the second domain.

The $V_H$ or $V_L$ domain of an IL-1β antibody or antigen-binding fragment thereof used in the disclosed methods may have $V_H$ and/or $V_L$ domains that are substantially identical to the $V_H$ or $V_L$ domains set forth in SEQ ID NO:27 and 37. A human IL-1βantibody disclosed herein may comprise a heavy chain that is substantially identical to that set forth as SEQ ID NO:29 and/or a light chain that is substantially identical to that set forth as SEQ ID NO:39. A human IL-1β antibody disclosed herein may comprise a heavy chain that comprises SEQ ID NO:29 and a light chain that comprises SEQ ID NO:39. A human IL-1β antibody disclosed herein may comprise: a) one heavy chain, comprising a variable domain having an amino acid sequence substantially identical to that shown in SEQ ID NO:27 and the constant part of a human heavy chain; and b) one light chain, comprising a variable domain having an amino acid sequence substantially identical to that shown in SEQ ID NO:37 and the constant part of a human light chain.

Other preferred IL-1β antagonists (e.g. antibodies) for use in the disclosed methods, kits and regimens are those set forth in U.S. Pat. No. 7,446,175 or 7,993,878 or 8,273,350, which are incorporated by reference herein in their entirety.

4. Fc Modifications

In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g. one or more chemical moieties can be attached to the antibody) or be modified to alter its glycosylation, again to alter one or more functional properties of the antibody. Each of these embodiments is described in further detail below. The numbering of residues in the Fc region is that of the EU numbering scheme of Edelman et al., PNAS, 1969 May, 63(1):78-85.

In one embodiment, the hinge region of CH1 is modified such that the number of cysteine residues in the hinge region is altered, e.g. increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcal protein A (SpA) binding relative to native Fc-hinge domain SpA binding. This approach is described in further detail in U.S. Pat. No. 6,165,745 by Ward et al.

In another embodiment, the antibody is modified to increase its biological half-life. Various approaches are possible. For example, one or more of the following mutations can be introduced: T252L, T254S, T256F, as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another embodiment, one or more amino acids selected from amino acid residues can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another embodiment, one or more amino acid residues are altered to thereby alter the ability of the antibody to fix complement. This approach is described further in PCT Publication WO 94/29351 by Bodmer et al.

In yet another embodiment, the Fc region is modified to increase the ability of the antibody to mediate antibody dependent cellular cytotoxicity (ADCC) and/or to increase the affinity of the antibody for an Fcγ receptor by modifying one or more amino acids. This approach is described further in PCT Publication WO 00/42072 by Presta. Moreover, the binding sites on human IgG1 for FcγRI, FcγRII, FcγRIII and FcRn have been mapped and variants with improved binding have been described (see Shields, R. L. et al, (2001) J Biol Chem 276:6591-6604).

In certain embodiments, the Fc domain of IgG1 isotype is used. In some specific embodiments, a mutant variant of IgG1 Fc fragment is used, e.g. a silent IgG1 Fc which reduces or eliminates the ability of the fusion polypeptide to mediate antibody dependent cellular cytotoxicity (ADCC) and/or to bind to an Fcγ receptor. An example of an IgG1 isotype silent mutant wherein Leucine residue is replaced by Alanine residue at amino acid positions 234 and 235 as described by Hezareh et al, J. Virol (2001); 75(24):12161-8.

In certain embodiments, the Fc domain is a mutant preventing glycosylation at position 297 of Fc domain. For example, the Fc domain contains an amino acid substitution of asparagine residue at position 297. Example of such amino acid substitution is the replacement of N297 by a glycine or an alanine.

Silenced effector functions can be obtained by mutation in the Fc region of the antibodies and have been described in the art: LALA and N297A (Strohl, W., 2009, Curr. Opin. Biotechnol. vol. 20(6):685-691); and D265A (Baudino et al., 2008, J. Immunol. 181:6664-69; Strohl, W., supra); and DAPA (D265A and P329A) (Shields R L., J Biol Chem. 2001; 276(9):6591-604; U.S. Patent Publication US2015/0320880). Examples of silent Fc IgG1 antibodies comprise the so-called LALA mutant comprising L234A and L235A mutation in the IgG1 Fc amino acid sequence. Another example of a silent IgG1 antibody comprises the D265A mutation. Another example of a silent IgG1 antibody is the so-called DAPA mutant, comprising D265A and P329A mutations to the IgG1 Fc amino acid sequence. Another silent IgG1 antibody comprises the N297A mutation, which results in aglycosylated/non-glycosylated antibodies. Additional Fc mutations for providing silenced effector function are described in PCT publication no. WO2014/145806 (e.g., in FIG. 7 of WO2014/145806), herein incorporated by reference in its entirety. One example from WO2014/145806 of a silent IgG1 antibody comprises a E233P, L234V, L235A, and S267K mutation, and a deletion of G236 (G236del). Another example from WO2014/145806 of a silent IgG1 antibody comprises a E233P, L234V, and L235A mutation, and a deletion of G236 (G236del). Another example from WO2014/145806 of a silent IgG1 antibody comprises a S267K mutation.

In still another embodiment, the glycosylation of an antibody is modified. For example, an aglycosylated antibody can be made (i.e., the antibody lacks glycosylation). Glycosylation can be altered to, for example, increase the affinity of the antibody for the antigen. Such carbohydrate modifications can be accomplished by; for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation. Therefore, in one embodiment, the antibodies of the invention are produced by recombinant expression in a cell line which exhibit hypofucosylation pattern, for example, a mammalian cell line with deficient expression of the FUT8 gene encoding fucosyltransferase. PCT Publication WO 03/035835 by Presta describes a variant CHO cell line, Lec13 cells, with reduced ability to attach fucose to Asn (297)-linked carbohydrates, also resulting in hypofucosylation of antibodies expressed in that host cell (see also Shields, R. L. et al., 2002 J. Biol. Chem. 277:26733-26740). PCT Publication WO 99/54342 by Umana et al. describes cell lines engineered to express glycoprotein-modifying glycosyl transferases (e.g. beta(1,4)-N acetylglucosaminyl-transferase Ill (GnTIII)) such that antibodies expressed in the engineered cell lines exhibit increased bisecting GlcNac structures which results in increased ADCC activity of the antibodies (see also Umana et al., 1999 Nat. Biotech. 17:176-180). Alternatively, the antibodies of the invention can be produced in a yeast or a filamentous fungi engineered for mammalian-like glycosylation pattern, and capable of producing antibodies lacking fucose as glycosylation pattern (see for example EP1297172B1).

Another modification of the antibodies herein that is contemplated by the invention is pegylation. An antibody can be pegylated to, for example, increase the biological (e.g. serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. The pegylation can be carried out by an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the invention. See for example, EP 0 154 316 by Nishimura et al. and EP 0 401 384 by Ishikawa et al.

Another modification of the antibodies that is contemplated by the invention is a conjugate or a protein fusion of at least the antigen-binding region of the antibody of the invention to serum protein, such as human serum albumin or a fragment thereof to increase half-life of the resulting molecule. Such approach is for example described in Ballance et al. EP0322094.

Another modification of the antibodies that is contemplated by the invention is one or more modifications to increase formation of a heterodimeric bispecific antibody. A variety of approaches available in the art can be used in for enhancing dimerization of the two heavy chain domains of bispecific antibodies, e.g., bbmAbs, as disclosed in, for example, EP 1870459A1; U.S. Pat. Nos. 5,582,996; 5,731, 168; 5,910,573; 5,932,448; 6,833,441; 7,183,076; U.S. Patent Application Publication No. 2006204493A1; and PCT Publication No. WO2009/089004A1, the contents of which are incorporated herein in their entireties.

Generation of bispecific antibodies using knobs-into-holes is disclosed e.g. in PCT Publication No. WO1996/027011, Ridgway et al., (1996), and Merchant et al. (1998).

(1) Knob-in-Hole (KIH)

Multispecific molecules, e.g., multispecific antibody or antibody-like molecules, of the present invention may comprise one or more, e.g., a plurality, of mutations to one or more of the constant domains, e.g., to the CH3 domains. In one example, the multispecific molecule of the present invention comprises two polypeptides that each comprise a heavy chain constant domain of an antibody, e.g., a CH2 or CH3 domain. In an example, the two heavy chain constant domains, e.g., the CH2 or CH3 domains of the multispecific molecule comprise one or more mutations that allow for a heterodimeric association between the two chains. In one aspect, the one or more mutations are disposed on the CH2 domain of the two heavy chains of the multispecific, e.g., bispecific, antibody or antibody-like molecule. In one aspect, the one or more mutations are disposed on the CH3 domains of at least two polypeptides of the multispecific molecule. In one aspect, the one or more mutations to a first polypeptide of the multispecific molecule comprising a heavy chain constant domain creates a "knob" and the one or more mutations to a second polypeptide of the multispecific molecule comprising a heavy chain constant domain creates a "hole," such that heterodimerization of the polypeptide of the multispecific molecule comprising a heavy chain constant domain causes the "knob" to interface (e.g., interact, e.g., a CH2 domain of a first polypeptide interacting with a CH2 domain of a second polypeptide, or a CH3 domain of a first polypeptide interacting with a CH3 domain of a second polypeptide) with the "hole." As the term is used herein, a "knob" refers to at least one amino acid side chain which projects from the interface of a first polypeptide of the multispecific molecule comprising a heavy chain constant domain and is therefore positionable in a compensatory "hole" in the interface with a second polypeptide of the multispecific molecule comprising a heavy chain constant domain so as to stabilize the heteromultimer, and thereby favor heteromultimer formation over homomultimer formation, for example. The knob may exist in the original interface or may be introduced synthetically (e.g. by altering nucleic acid encoding the interface). The preferred import residues for the formation of a knob are generally naturally occurring amino acid residues and are preferably selected from arginine (R), phenylalanine (F), tyrosine (Y) and tryptophan (W). Most preferred are tryptophan and tyrosine. In the preferred embodiment, the original residue for the formation of the protuberance has a small side chain volume, such as alanine, asparagine, aspartic acid, glycine, serine, threonine or valine.

A "hole" refers to at least one amino acid side chain which is recessed from the interface of a second polypeptide of the multispecific molecule comprising a heavy chain constant domain and therefore accommodates a corresponding knob on the adjacent interfacing surface of a first polypeptide of the multispecific molecule comprising a heavy chain constant domain. The hole may exist in the original interface or may be introduced synthetically (e.g. by altering nucleic acid encoding the interface). The preferred import residues for the formation of a hole are usually naturally occurring amino acid residues and are preferably selected from alanine (A), serine (S), threonine (T) and valine (V). Most preferred are serine, alanine or threonine. In the preferred embodiment, the original residue for the formation of the hole has a large side chain volume, such as tyrosine, arginine, phenylalanine or tryptophan.

In a preferred embodiment, a first CH3 domain is mutated at residue 366, 405 or 407 according to the EU numbering scheme of Edelman et al., PNAS, 1969 May, 63(1):78-85 to create either a "knob" or a hole" (as described above), and the second CH3 domain that heterodimerizes with the first CH3 domain is mutated at: residue 407 if residue 366 is mutated in the first CH3 domain, residue 349 if residue 405 is mutated in the first CH3 domain, or residue 366 if residue 407 is mutated in the first CH3 domain, according to the EU numbering scheme of Edelman et al., PNAS, 1969 May, 63(1):78-85, to create a "hole" or "knob" complementary to the "knob" or "hole" of the first CH3 domain.

In another preferred embodiment, a first CH3 domain is mutated at residue 366 according to the EU numbering scheme of Edelman et al., PNAS, 1969 May, 63(1):78-85 to create either a "knob" or a hole" (as described above), and the second CH3 domain that heterodimerizes with the first CH3 domain is mutated at residues 366, 368 and/or 407, according to the EU numbering scheme of Edelman et al., PNAS, 1969 May, 63(1):78-85, to create a "hole" or "knob" complementary to the "knob" or "hole" of the first CH3 domain. In one embodiment, the mutation to the first CH3 domain introduces a tyrosine (Y) residue at position 366. In an embodiment, the mutation to the first CH3 is T366Y. In one embodiment, the mutation to the first CH3 domain introduces a tryptophan (W) residue at position 366. In an embodiment, the mutation to the first CH3 is T366W. In embodiments, the mutation to the second CH3 domain that heterodimerizes with the first CH3 domain mutated at position 366 (e.g., has a tyrosine (Y) or tryptophan (W) introduced at position 366, e.g., comprises the mutation T366Y or T366W), comprises a mutation at position 366, a mutation at position 368 and a mutation at position 407, according to the EU numbering scheme of Edelman et al., PNAS, 1969 May, 63(1):78-85 In embodiments, the mutation at position 366 introduces a serine (S) residue, the mutation at position 368 introduces an alanine (A), and the mutation at position 407 introduces a valine (V). In embodiments, the mutations comprise T366S, L368A and Y407V. In one embodiment the first CH3 domain of the multispecific molecule comprises the mutation T366Y, and the second CH3 domain that heterodimerizes with the first CH3 domain comprises the mutations T366S, L368A and Y407V, or vice versa. In one embodiment the first CH3 domain of the multispecific molecule comprises the mutation T366W, and the second CH3 domain that heterodimerizes with the first CH3 domain comprises the mutations T366S, L368A and Y407V, or vice versa.

Additional steric or "skew" (e.g., knob in hole) mutations are described in PCT publication no. WO2014/145806 (for example, FIG. 3, FIG. 4 and FIG. 12 of WO2014/145806), PCT publication no. WO2014/110601, and PCT publication no. WO 2016/086186, WO 2016/086189, WO 2016/086196 and WO 2016/182751 the contents of which are incorporated herein in their entireties. An example of a KIH variant comprises a first constant chain comprising a L368D and a K370S mutation, paired with a second constant chain comprising a S364K and E357Q mutation.

Additional knob in hole mutation pairs suitable for use in any of the multispecific molecules of the present invention are further described in, for example, WO1996/027011, and Merchant et al., Nat. Biotechnol., 16:677-681 (1998), the contents of which are hereby incorporated by reference in their entirety.

In any of the embodiments described herein, the CH3 domains may be additionally mutated to introduce a pair of cysteine residues. Without being bound by theory, it is believed that the introduction of a pair of cysteine residues capable of forming a disulfide bond provide stability to the heterodimerized multispecific molecule. In embodiments, the first CH3 domain comprises a cysteine at position 354, according to the EU numbering scheme of Edelman et al., PNAS, 1969 May, 63(1):78-85, and the second CH3 domain that heterodimerizes with the first CH3 domain comprises a cysteine at position 349, according to the EU numbering scheme of Edelman et al., PNAS, 1969 May, 63(1):78-85. In embodiments, the first CH3 domain of the multispecific molecule comprises a cysteine at position 354 (e.g., comprises the mutation S354C) and a tyrosine (Y) at position 366 (e.g., comprises the mutation T366Y), and the second CH3 domain that heterodimerizes with the first CH3 domain comprises a cysteine at position 349 (e.g., comprises the mutation Y349C), a serine at position 366 (e.g., comprises the mutation T366S), an alanine at position 368 (e.g., comprises the mutation L368A), and a valine at position 407 (e.g., comprises the mutation Y407V). In embodiments, the first CH3 domain of the multispecific molecule comprises a cysteine at position 354 (e.g., comprises the mutation S354C) and a tryptophan (W) at position 366 (e.g., comprises the mutation T366W), and the second CH3 domain that heterodimerizes with the first CH3 domain comprises a cysteine at position 349 (e.g., comprises the mutation Y349C), a serine at position 366 (e.g., comprises the mutation T366S), an alanine at position 368 (e.g., comprises the mutation L368A), and a valine at position 407 (e.g., comprises the mutation Y407V).

(2) Alternative Knob and Hole: IgG Heterodimerization

In one aspect, heterodimerization of the polypeptide chains (e.g., of the half antibodies) of the multispecific molecule is increased by introducing one or more mutations in a CH3 domain which is derived from the IgG1 antibody class. In an embodiment, the mutations comprise a K409R mutation to one CH3 domain paired with F405L mutation in the second CH3 domain, according to the EU numbering scheme of Edelman et al., PNAS, 1969 May, 63(1):78-85. Additional mutations may also, or alternatively, be at positions 366, 368, 370, 399, 405, 407, and 409 according to the EU numbering scheme of Edelman et al., PNAS, 1969 May, 63(1):78-85. Preferably, heterodimerization of polypeptides comprising such mutations is achieved under reducing conditions, e.g., 10-100 mM 2-MEA (e.g., 25, 50, or 100 mM 2-MEA) for 1-10, e.g., 1.5-5, e.g., 5, hours at 25-37 C, e.g., 25 C or 37 C.

The amino acid replacements described herein are introduced into the CH3 domains using techniques which are well known in the art. Normally the DNA encoding the heavy chain(s) is genetically engineered using the techniques described in Mutagenesis: a Practical Approach. Oligonucleotide-mediated mutagenesis is a preferred method for preparing substitution variants of the DNA encoding the two hybrid heavy chains. This technique is well known in the art as described by Adelman et al., (1983) DNA, 2:183.

The IgG heterodimerization strategy is described in, for example, WO2008/119353, WO2011/131746, and WO2013/060867, the contents of which are hereby incorporated by reference in their entirety.

In any of the embodiments described herein, the CH3 domains may be additionally mutated to introduce a pair of cysteine residues. Without being bound by theory, it is believed that the introduction of a pair of cysteine residues capable of forming a disulfide bond provide stability to the heterodimerized multispecific molecule. In embodiments, the first CH3 domain comprises a cysteine at position 354, according to the EU numbering scheme of Edelman et al., PNAS, 1969 May, 63(1):78-85, and the second CH3 domain that heterodimerizes with the first CH3 domain comprises a cysteine at position 349, according to the EU numbering scheme of Edelman et al., PNAS, 1969 May, 63(1):78-85.

(3) Polar Bridge

In one aspect, heterodimerization of the polypeptide chains (e.g., of the half antibodies) of the multispecific molecule is increased by introducing mutations based on the "polar-bridging" rational, which is to make residues at the binding interface of the two polypeptide chains to interact with residues of similar (or complimentary) physical property in the heterodimer configuration, while with residues of different physical property in the homodimer configuration. In particular, these mutations are designed so that, in the heterodimer formation, polar residues interact with polar residues, while hydrophobic residues interact with hydrophobic residues. In contrast, in the homodimer formation, residues are mutated so that polar residues interact with hydrophobic residues. The favorable interactions in the heterodimer configuration and the unfavorable interactions in the homodimer configuration work together to make it more likely for CH3 domains to form heterodimers than to form homodimers.

In an exemplary embodiment, the above mutations are generated at one or more positions of residues 364, 368, 399, 405, 409, and 411 of CH3 domain, amino acid numbering according to the EU numbering scheme of Edelman et al., PNAS, 1969 May, 63(1):78-85.

In one aspect, one or more mutations selected from a group consisting of: Ser364Leu, Thr366Val, Leu368Gln, Asp399Lys, Phe405Ser, Lys409Phe and Thr411Lys are introduced into one of the two CH3 domains. (Ser364Leu: original residue of serine at position 364 is replaced by leucine; Thr366Val: original residue of threonine at position 366 is replaced by valine; Leu368Gln: original residue of leucine at position 368 is replaced by glutamine; Asp399Lys: original residue aspartic acid at position 399 is replaced by lysine; Phe405Ser: original residue phenylalanine at position 405 is replaced by serine; Lys409Phe: original residue lysine at position 409 is replaced by phenylalanine; Thr411Lys: original residue of threonine at position 411 is replaced by lysine.).

In another aspect, the other CH3 can be introduced with one or more mutations selected from a group consisting of: Tyr407Phe, Lys409Gln and Thr411Asp (Tyr407Phe: original residue tyrosine at position 407 is replaced by phenylalanine; Lys409Glu: original residue lysine at position 409 is replaced by glutamic acid; Thr411Asp: original residue of threonine at position 411 is replaced by aspartic acid).

In a further aspect, one CH3 domain has one or more mutations selected from a group consisting of: Ser364Leu, Thr366Val, Leu368Gln, Asp399Lys, Phe405Ser, Lys409Phe and Thr411Lys, while the other CH3 domain has one or more mutations selected from a group consisting of: Tyr407Phe, Lys409Gln and Thr411Asp.

In one exemplary embodiment, the original residue of threonine at position 366 of one CH3 domain is replaced by valine, while the original residue of tyrosine at position 407 of the other CH3 domain is replaced by phenylalanine.

In another exemplary embodiment, the original residue of serine at position 364 of one CH3 domain is replaced by leucine, while the original residue of leucine at position 368 of the same CH3 domain is replaced by glutamine.

In yet another exemplary embodiment, the original residue of phenylalanine at position 405 of one CH3 domain is replaced by serine and the original residue of lysine at position 409 of this CH3 domain is replaced by phenylalanine, while the original residue of lysine at position 409 of the other CH3 domain is replaced by glutamine.

In yet another exemplary embodiment, the original residue of aspartic acid at position 399 of one CH3 domain is replaced by lysine, and the original residue of threonine at position 411 of the same CH3 domain is replaced by lysine, while the original residue of threonine at position 411 of the other CH3 domain is replaced by aspartic acid.

The amino acid replacements described herein are introduced into the CH3 domains using techniques which are well known in the art. Normally the DNA encoding the heavy chain(s) is genetically engineered using the techniques described in Mutagenesis: a Practical Approach. Oligonucleotide-mediated mutagenesis is a preferred method for preparing substitution variants of the DNA encoding the two hybrid heavy chains. This technique is well known in the art as described by Adelman et al., (1983) DNA, 2:183.

The polar bridge strategy is described in, for example, WO2006/106905, WO2009/089004 and K. Gunasekaran, et al. (2010) The Journal of Biological Chemistry, 285:19637-19646, the contents of which are hereby incorporated by reference in their entirety.

Additional polar bridge mutations are described in, for example, PCT publication no. WO2014/145806 (for example, FIG. 6 of WO2014/145806), PCT publication no. WO2014/110601, and PCT publication no. WO 2016/086186, WO 2016/086189, WO 2016/086196 and WO 2016/182751 the contents of which are incorporated herein in their entireties. An example of a polar bridge variant comprises a constant chain comprising a N208D, Q295E, N384D, Q418E and N421D mutation.

In any of the embodiments described herein, the CH3 domains may be additionally mutated to introduce a pair of cysteine residues. Without being bound by theory, it is believed that the introduction of a pair of cysteine residues capable of forming a disulfide bond provide stability to the heterodimerized multispecific molecule. In embodiments, the first CH3 domain comprises a cysteine at position 354, according to the EU numbering scheme of Edelman et al., PNAS, 1969 May, 63(1):78-85, and the second CH3 domain that heterodimerizes with the first CH3 domain comprises a cysteine at position 349, according to the EU numbering scheme of Edelman et al., PNAS, 1969 May, 63(1):78-85.

Additional strategies for enhancing heterodimerization are described in, for example, WO2016/105450, WO2016/086186, WO2016/086189, WO2016/086196, WO2016/141378, and WO2014/145806, and WO2014/110601, the entire contents of each of which is hereby incorporated by reference in its entirety. Any of said strategies may be employed in a multispecific molecule described herein.

In embodiments, two or more of the modifications discussed herein are combined in a single bispecific antibody, e.g., bbmAb.

5. Example 1: Generation of the bbmAb bbmAb1

By way of example, generation of a specific bbmAb is described below, to enable a person skilled in the art to practice the invention.

The resulting bbmAb, bbmAb1, is a bispecific IgG1, with LALA silencing mutations, simultaneously binding to two distinct targets, IL-1β and IL-18. The antibody combines two distinct antigen binding arms (Fab fragments), whereas the Fab directed against IL-1β is based on mAb2 and contains a kappa light chain (Vk6). The Fab directed against IL-18 is based on mAb1 and is composed of a lambda light chain (Vλ1). In order to drive hetero-dimerization of the Fc domain during expression a "knob" with a bulky amino acid (aa) side chain (S354C and T366W) in the mAb1 heavy chain and a "hole" with small aa side chains (Y349C, T366S, L368A, Y407V) were introduced in the mAb2 heavy chain.

For ease of reference, the amino acid sequences of the hypervariable regions of bbmAb1, based on the Kabat definition and the Chothia definition, as well as the $V_L$ and $V_H$ domains and full heavy and light chains are provided in Table 3, below.

TABLE 3

Amino acid sequences of the hypervariable regions (CDRs), variable domains (VH and VL) and full chains of bbmAb1. The DNA encoding the first VL of is set forth in SEQ ID NO: 102 and the DNA encoding the second VL is set forth in SEQ ID NO: 70. The DNA encoding the first VH is set forth in SEQ ID NO: 86 and the DNA encoding the second VH is set forth in SEQ ID NO: 54.

| bbmAb1 heavy chain 1 (from mAb1) | | |
|---|---|---|
| CDR1-1 | Kabat | SEQ ID NO: 76 |
| | Chothia | SEQ ID NO: 79 |
| | IMGT | SEQ ID NO: 82 |
| CDR2-1 | Kabat | SEQ ID NO: 77 |
| | Chothia | SEQ ID NO: 80 |
| | IMGT | SEQ ID NO: 83 |
| CDR3-1 | Kabat | SEQ ID NO: 78 |
| | Chothia | SEQ ID NO: 81 |
| | IMGT | SEQ ID NO: 84 |
| VH-1 | | SEQ ID NO: 85 |
| Heavy Chain-1 | | SEQ ID NO: 87 |
| bbmAb1 light chain 1 (from mAb1) | | |
| CDR1-1 | Kabat | SEQ ID NO: 92 |
| | Chothia | SEQ ID NO: 95 |
| | IMGT | SEQ ID NO: 98 |
| CDR2-1 | Kabat | SEQ ID NO: 93 |
| | Chothia | SEQ ID NO: 96 |
| | IMGT | SEQ ID NO: 99 |
| CDR3-1 | Kabat | SEQ ID NO: 94 |
| | Chothia | SEQ ID NO: 97 |
| | IMGT | SEQ ID NO: 100 |
| VL-1 | | SEQ ID NO: 101 |
| Light Chain-1 | | SEQ ID NO: 103 |
| bbmAb1 heavy chain 2 (from mAb2) | | |
| CDR1-2 | Kabat | SEQ ID NO: 44 |
| | Chothia | SEQ ID NO: 47 |
| | IMGT | SEQ ID NO: 50 |
| CDR2-2 | Kabat | SEQ ID NO: 45 |
| | Chothia | SEQ ID NO: 48 |
| | IMGT | SEQ ID NO: 51 |

TABLE 3-continued

Amino acid sequences of the hypervariable regions (CDRs), variable domains (VH and VL) and full chains of bbmAb1. The DNA encoding the first VL of is set forth in SEQ ID NO: 102 and the DNA encoding the second VL is set forth in SEQ ID NO: 70. The DNA encoding the first VH is set forth in SEQ ID NO: 86 and the DNA encoding the second VH is set forth in SEQ ID NO: 54.

| | | |
|---|---|---|
| CDR3-2 | Kabat | SEQ ID NO: 46 |
| | Chothia | SEQ ID NO: 49 |
| | IMGT | SEQ ID NO: 52 |
| VH-2 | | SEQ ID NO: 53 |
| Heavy Chain-2 | | SEQ ID NO: 55 |
| bbmAb1 light chain 2 (from mAb2) | | |
| CDR1-2 | Kabat | SEQ ID NO: 60 |
| | Chothia | SEQ ID NO: 63 |
| | IMGT | SEQ ID NO: 66 |
| CDR2-2 | Kabat | SEQ ID NO: 61 |
| | Chothia | SEQ ID NO: 64 |
| | IMGT | SEQ ID NO: 67 |
| CDR3-2 | Kabat | SEQ ID NO: 62 |
| | Chothia | SEQ ID NO: 65 |
| | IMGT | SEQ ID NO: 68 |
| VL-2 | | SEQ ID NO: 69 |
| Light Chain-2 | | SEQ ID NO: 71 |

In one embodiment, the IL-18/IL-1β bispecific antibody comprises a first immunoglobulin heavy chain variable domain ($V_{H1}$) comprising hypervariable regions CDR1, CDR2 and CDR3, said CDR1 having the amino acid sequence SEQ ID NO:76, said CDR2 having the amino acid sequence SEQ ID NO:77, and said CDR3 having the amino acid sequence SEQ ID NO:78. In one embodiment, IL-18/IL-1β bispecific antibody comprises a first immunoglobulin heavy chain variable domain ($V_{H1}$) comprising hypervariable regions CDR1, CDR2 and CDR3, said CDR1 having the amino acid sequence SEQ ID NO:79, said CDR2 having the amino acid sequence SEQ ID NO:80, and said CDR3 having the amino acid sequence SEQ ID NO:81. In one embodiment, IL-18/IL-1β bispecific antibody comprises a first immunoglobulin heavy chain variable domain ($V_{H1}$) comprising hypervariable regions CDR1, CDR2 and CDR3, said CDR1 having the amino acid sequence SEQ ID NO:82, said CDR2 having the amino acid sequence SEQ ID NO:83, and said CDR3 having the amino acid sequence SEQ ID NO:84.

In one embodiment, the IL-18/IL-1β bispecific antibody comprises a second immunoglobulin heavy chain variable domain ($V_{H2}$) comprising hypervariable regions CDR1, CDR2 and CDR3, said CDR1 having the amino acid sequence SEQ ID NO:44, said CDR2 having the amino acid sequence SEQ ID NO:45, and said CDR3 having the amino acid sequence SEQ ID NO:46. In one embodiment, the IL-18/IL-1β bispecific antibody comprises a second immunoglobulin heavy chain variable domain (VH2) comprising hypervariable regions CDR1, CDR2 and CDR3, said CDR1 having the amino acid sequence SEQ ID NO:47, said CDR2 having the amino acid sequence SEQ ID NO:48, and said CDR3 having the amino acid sequence SEQ ID NO:49. In one embodiment, the IL-18/IL-1β bispecific antibody comprises a second immunoglobulin heavy chain variable domain ($V_{H2}$) comprising hypervariable regions CDR1, CDR2 and CDR3, said CDR1 having the amino acid sequence SEQ ID NO:50, said CDR2 having the amino acid sequence SEQ ID NO:51, and said CDR3 having the amino acid sequence SEQ ID NO:52.

In one embodiment, the IL-18/IL-1β bispecific antibody comprises a first immunoglobulin light chain variable domain (Vu) comprising hypervariable regions CDR1, CDR2 and CDR3, said CDR1 having the amino acid sequence SEQ ID NO:92, said CDR2 having the amino acid sequence SEQ ID NO:93 and said CDR3 having the amino acid sequence SEQ ID NO:94. In one embodiment, the IL-18/IL-1β bispecific antibody comprises a first immunoglobulin light chain variable domain (Vu) comprising hypervariable regions CDR1, CDR2 and CDR3, said CDR1 having the amino acid sequence SEQ ID NO:95, said CDR2 having the amino acid sequence SEQ ID NO:96 and said CDR3 having the amino acid sequence SEQ ID NO:97. In one embodiment, the IL-18/IL-18 bispecific antibody comprises a first immunoglobulin light chain variable domain (Vu) comprising hypervariable regions CDR1, CDR2 and CDR3, said CDR1 having the amino acid sequence SEQ ID NO:98, said CDR2 having the amino acid sequence SEQ ID NO:99 and said CDR3 having the amino acid sequence SEQ ID NO:100.

In one embodiment, the IL-18/IL-1β bispecific antibody comprises a second immunoglobulin light chain variable domain ($V_{L2}$) comprising hypervariable regions CDR1, CDR2 and CDR3, said CDR1 having the amino acid sequence SEQ ID NO:60, said CDR2 having the amino acid sequence SEQ ID NO:61 and said CDR3 having the amino acid sequence SEQ ID NO:62. In one embodiment, the IL-18/IL-1β bispecific antibody comprises a second immunoglobulin light chain variable domain ($V_{L2}$) comprising hypervariable regions CDR1, CDR2 and CDR3, said CDR1 having the amino acid sequence SEQ ID NO:63, said CDR2 having the amino acid sequence SEQ ID NO:64 and said CDR3 having the amino acid sequence SEQ ID NO:65. In one embodiment, the IL-18/IL-1β bispecific antibody comprises a second immunoglobulin light chain variable domain ($V_{L2}$) comprising hypervariable regions CDR1, CDR2 and CDR3, said CDR1 having the amino acid sequence SEQ ID NO:66, said CDR2 having the amino acid sequence SEQ ID NO:67 and said CDR3 having the amino acid sequence SEQ ID NO:68.

In one embodiment, the IL-18/IL-1β bispecific antibody comprises a first immunoglobulin $V_{H1}$ domain and a first immunoglobulin $V_{L1}$ domain, wherein: a) the first immunoglobulin $V_{H1}$ domain comprises (e.g. in sequence): i) hypervariable regions CDR1, CDR2 and CDR3, said CDR1 having the amino acid sequence SEQ ID NO:76, said CDR2 having the amino acid sequence SEQ ID NO:77, and said CDR3 having the amino acid sequence SEQ ID NO:78; or ii) hypervariable regions CDR1, CDR2 and CDR3, said CDR1 having the amino acid sequence SEQ ID NO:79, said CDR2 having the amino acid sequence SEQ ID NO:80, and said CDR3 having the amino acid sequence SEQ ID NO:81; or iii) hypervariable regions CDR1, CDR2 and CDR3, said CDR1 having the amino acid sequence SEQ ID NO:82, said CDR2 having the amino acid sequence SEQ ID NO:83, and said CDR3 having the amino acid sequence SEQ ID NO:84 and b) the first immunoglobulin $V_{L1}$ domain comprises (e.g. in sequence): i) hypervariable regions CDR1, CDR2 and CDR3, said CDR1 having the amino acid sequence SEQ ID NO:92, said CDR2 having the amino acid sequence SEQ ID NO:93, and said CDR3 having the amino acid sequence SEQ ID NO:94 or ii) hypervariable regions CDR1, CDR2 and CDR3, said CDR1 having the amino acid sequence SEQ ID NO:95, said CDR2 having the amino acid sequence SEQ ID NO:96, and said CDR3 having the amino acid sequence SEQ ID NO:97 or iii) hypervariable regions CDR1, CDR2 and CDR3, said CDR1 having the amino acid sequence SEQ ID NO:98, said CDR2 having the amino acid sequence SEQ ID NO:99, and said CDR3 having the amino acid sequence SEQ ID NO:100.

In one embodiment, the IL-18/IL-1β bispecific antibody comprises a second immunoglobulin $V_{H2}$ domain and a second immunoglobulin $V_{L2}$ domain, wherein: a) the second immunoglobulin $V_{H2}$ domain comprises (e.g. in sequence): i) hypervariable regions CDR1, CDR2 and CDR3, said CDR1 having the amino acid sequence SEQ ID NO:44, said CDR2 having the amino acid sequence SEQ ID NO:45, and said CDR3 having the amino acid sequence SEQ ID NO:46; or ii) hypervariable regions CDR1, CDR2 and CDR3, said CDR1 having the amino acid sequence SEQ ID NO:47, said CDR2 having the amino acid sequence SEQ ID NO:48, and said CDR3 having the amino acid sequence SEQ ID NO:49; or iii) hypervariable regions CDR1, CDR2 and CDR3, said CDR1 having the amino acid sequence SEQ ID NO:50, said CDR2 having the amino acid sequence SEQ ID NO:51, and said CDR3 having the amino acid sequence SEQ ID NO:52 and b) the second immunoglobulin $V_{L2}$ domain comprises (e.g. in sequence): i) hypervariable regions CDR1, CDR2 and CDR3, said CDR1 having the amino acid sequence SEQ ID NO:60, said CDR2 having the amino acid sequence SEQ ID NO:61, and said CDR3 having the amino acid sequence SEQ ID NO:62 or ii) hypervariable regions CDR1, CDR2 and CDR3, said CDR1 having the amino acid sequence SEQ ID NO:63, said CDR2 having the amino acid sequence SEQ ID NO:64, and said CDR3 having the amino acid sequence SEQ ID NO:65 or iii) hypervariable regions CDR1, CDR2 and CDR3, said CDR1 having the amino acid sequence SEQ ID NO:66, said CDR2 having the amino acid sequence SEQ ID NO:67, and said CDR3 having the amino acid sequence SEQ ID NO:68.

In one embodiment, the IL-18/IL-1β bispecific antibody comprises: a) a first immunoglobulin heavy chain variable domain ($V_{H1}$) comprising the amino acid sequence set forth as SEQ ID NO:85; b) a first immunoglobulin light chain variable domain (Vu) comprising the amino acid sequence set forth as SEQ ID NO:101; c) a first immunoglobulin $V_{H1}$ domain comprising the amino acid sequence set forth as SEQ ID NO:85 and a first immunoglobulin $V_{L1}$ domain comprising the amino acid sequence set forth as SEQ ID NO:101; d) a first immunoglobulin $V_{H1}$ domain comprising the hypervariable regions set forth as SEQ ID NO:76, SEQ ID NO:77, and SEQ ID NO:78; e) a first immunoglobulin $V_{L1}$ domain comprising the hypervariable regions set forth as SEQ ID NO:92, SEQ ID NO:93 and SEQ ID NO:94; f) a first immunoglobulin $V_{H1}$ domain comprising the hypervariable regions set forth as SEQ ID NO:79, SEQ ID NO:80 and SEQ ID NO:81; g) a first immunoglobulin $V_{L1}$ domain comprising the hypervariable regions set forth as SEQ ID NO:95, SEQ ID NO:96 and SEQ ID NO:97; h) a first immunoglobulin $V_{H1}$ domain comprising the hypervariable regions set forth as SEQ ID NO:76, SEQ ID NO:77, and SEQ ID NO:78 and a first immunoglobulin $V_{L1}$ domain comprising the hypervariable regions set forth as SEQ ID NO:92, SEQ ID NO:93 and SEQ ID NO:94; i) a first immunoglobulin $V_{H1}$ domain comprising the hypervariable regions set forth as SEQ ID NO:79, SEQ ID NO:80, and SEQ ID NO:81 and a first immunoglobulin $V_{L1}$ domain comprising the hypervariable regions set forth as SEQ ID NO:95, SEQ ID NO:96 and SEQ ID NO:97; j) a first light chain comprising SEQ ID NO:103; k) a first heavy chain comprising SEQ ID NO:87; or l) a first light chain comprising SEQ ID NO:103 and a first heavy chain comprising SEQ ID NO:87.

In one embodiment, the IL-18/IL-1β bispecific antibody comprises: a) a second immunoglobulin heavy chain variable domain ($V_{H2}$) comprising the amino acid sequence set forth as SEQ ID NO:53; b) a second immunoglobulin light chain variable domain ($V_{L2}$) comprising the amino acid sequence set forth as SEQ ID NO:69; c) a second immunoglobulin $V_{H2}$ domain comprising the amino acid sequence set forth as SEQ ID NO:53 and a second immunoglobulin $V_{L2}$ domain comprising the amino acid sequence set forth as SEQ ID NO:69; d) a second immunoglobulin $V_{H2}$ domain comprising the hypervariable regions set forth as SEQ ID NO:44, SEQ ID NO:45, and SEQ ID NO:46; e) a second immunoglobulin $V_{L2}$ domain comprising the hypervariable regions set forth as SEQ ID NO:60, SEQ ID NO:61 and SEQ ID NO:62; f) a second immunoglobulin $V_{H2}$ domain comprising the hypervariable regions set forth as SEQ ID NO:47, SEQ ID NO:48 and SEQ ID NO:49; g) a second immunoglobulin $V_{L2}$ domain comprising the hypervariable regions set forth as SEQ ID NO:63, SEQ ID NO:64 and SEQ ID NO:65; h) a second immunoglobulin $V_{H2}$ domain comprising the hypervariable regions set forth as SEQ ID NO:44, SEQ ID NO:45, and SEQ ID NO:46 and a second immunoglobulin $V_{L2}$ domain comprising the hypervariable regions set forth as SEQ ID NO:60, SEQ ID NO:61 and SEQ ID NO:62; i) a second immunoglobulin $V_{H2}$ domain comprising the hypervariable regions set forth as SEQ ID NO:47, SEQ ID NO:48, and SEQ ID NO:49 and a second immunoglobulin $V_{L2}$ domain comprising the hypervariable regions set forth as SEQ ID NO:63, SEQ ID NO:64 and SEQ ID NO:65; j) a second light chain comprising SEQ ID NO:81; k) a second heavy chain comprising SEQ ID NO:55; or l) a second light chain comprising SEQ ID NO:81 and a second heavy chain comprising SEQ ID NO:55.

In some embodiments, the IL-18/IL-1β bispecific antibody comprises a the three CDRs of SEQ ID NO:53. In other embodiments, the IL-18/IL-1β bispecific antibody comprises the three CDRs of SEQ ID NO:69. In other embodiments, the IL-18/IL-1β bispecific antibody comprises the three CDRs of SEQ ID NO:53 and the three CDRs of SEQ ID NO:69. In some embodiments, the IL-18/IL-1β bispecific antibody comprises the three CDRs of SEQ ID NO:85. In other embodiments, the IL-18/IL-1β bispecific antibody comprises the three CDRs of SEQ ID NO:101. In other embodiments, the IL-18/IL-1β bispecific antibody comprises the three CDRs of SEQ ID NO:85 and the three CDRs of SEQ ID NO:101.

In some embodiments, the IL-18/IL-1β bispecific antibody comprises a the three CDRs of SEQ ID NO:85. In other embodiments, the IL-18/IL-1β bispecific antibody comprises the three CDRs of SEQ ID NO:101. In other embodiments, the IL-18/IL-1β bispecific antibody comprises the three CDRs of SEQ ID NO:85 and the three CDRs of SEQ ID NO:101. In some embodiments, the IL-18/IL-1β bispecific antibody comprises the three CDRs of SEQ ID NO:53. In other embodiments, the IL-18/IL-1β bispecific antibody comprises the three CDRs of SEQ ID NO:69. In other embodiments, the IL-18/IL-1β bispecific antibody comprises the three CDRs of SEQ ID NO:53 and the three CDRs of SEQ ID NO:69. In an embodiment, the L-18/IL-1βbispecific antibody comprises the three CDRs of SEQ ID NO:85, the three CDRs of SEQ ID NO:101, the three CDRs of SEQ ID NO:53 and the three CDRs of SEQ ID NO:69.

In one embodiment, the first part of the IL-18/IL-1β bispecific antibody is selected from a human IL-18 antibody that comprises at least: a) an immunoglobulin heavy chain or fragment thereof which comprises a variable domain comprising, in sequence, the hypervariable regions CDR1, CDR2 and CDR3 and the constant part or fragment thereof of a human heavy chain; said CDR1 having the amino acid sequence SEQ ID NO:76, said CDR2 having the amino acid sequence SEQ ID NO:77, and said CDR3 having the amino acid sequence SEQ ID NO:78; and b) an immunoglobulin light chain or fragment thereof which comprises a variable domain comprising, in sequence, the hypervariable regions CDR1, CDR2, and CDR3 and the constant part or fragment thereof of a human light chain, said CDR1 having the amino acid sequence SEQ ID NO:92, said CDR2 having the amino acid sequence SEQ ID NO:93, and said CDR3 having the amino acid sequence SEQ ID NO:94. Furthermore the second part of the IL-18/IL-1β bispecific antibody is selected from a human IL-1βantibody that comprises at least: a) an immunoglobulin heavy chain or fragment thereof which comprises a variable domain comprising, in sequence, the hypervariable regions CDR1, CDR2 and CDR3 and the constant part or fragment thereof of a human heavy chain; said CDR1 having the amino acid sequence SEQ ID NO:44, said CDR2 having the amino acid sequence SEQ ID NO:45, and said CDR3 having the amino acid sequence SEQ ID NO:46; and b) an immunoglobulin light chain or fragment thereof which comprises a variable domain comprising, in sequence, the hypervariable regions CDR1, CDR2, and CDR3 and the constant part or fragment thereof of a human light chain, said CDR1 having the amino acid sequence SEQ ID NO:60, said CDR2 having the amino acid sequence SEQ ID NO:61, and said CDR3 having the amino acid sequence SEQ ID NO:62.

In one embodiment, the first part of the IL-18/IL-1β bispecific antibody is selected from a human IL-18 antibody that comprises at least: a) an immunoglobulin heavy chain or fragment thereof which comprises a variable domain comprising, in sequence, the hypervariable regions CDR1, CDR2 and CDR3 and the constant part or fragment thereof of a human heavy chain; said CDR1 having the amino acid sequence SEQ ID NO:76, said CDR2 having the amino acid sequence SEQ ID NO:77 and said CDR3 having the amino acid sequence SEQ ID NO:78; and b) an immunoglobulin light chain or fragment thereof which comprises a variable domain comprising, in sequence, the hypervariable regions CDR1, CDR2, and CDR3 and the constant part or fragment thereof of a human light chain, said CDR1 having the amino acid sequence SEQ ID NO:92, said CDR2 having the amino acid sequence SEQ ID NO:93, and said CDR3 having the amino acid sequence SEQ ID NO:94. Furthermore, the second part of the IL-18/IL-1β bispecific antibody is selected from a human IL-1βantibody that comprises at least: a) an immunoglobulin heavy chain or fragment thereof which comprises a variable domain comprising, in sequence, the hypervariable regions CDR1, CDR2 and CDR3 and the constant part or fragment thereof of a human heavy chain; said CDR1 having the amino acid sequence SEQ ID NO:44, said CDR2 having the amino acid sequence SEQ ID NO:45 and said CDR3 having the amino acid sequence SEQ ID NO:46; and b) an immunoglobulin light chain or fragment thereof which comprises a variable domain comprising, in sequence, the hypervariable regions CDR1, CDR2, and CDR3 and the constant part or fragment thereof of a human light chain, said CDR1 having the amino acid sequence SEQ ID NO:60, said CDR2 having the amino acid sequence SEQ ID NO:61, and said CDR3 having the amino acid sequence SEQ ID NO:62.

The first $V_{H1}$ or $V_u$ domain of an IL-18/IL-1β bispecific antibody used in the disclosed methods may have a first $V_{H1}$ and/or first $V_{L1}$ domains that are substantially identical to the $V_H$ or $V_L$ domains set forth in SEQ ID NO:85 and 101. An IL-18/IL-1β bispecific antibody disclosed herein may comprise a first heavy chain that is substantially identical to that set forth as SEQ ID NO:87 and/or a first light chain that is substantially identical to that set forth as SEQ ID NO:103. An IL-18/IL-1β bispecific antibody disclosed herein may comprise a first heavy chain that comprises SEQ ID NO:87 and a first light chain that comprises SEQ ID NO:103. An IL-18/IL-1β bispecific antibody disclosed herein may comprise: a) a first heavy chain, comprising a variable domain having an amino acid sequence substantially identical to that shown in SEQ ID NO:85 and the constant part of a human heavy chain having a hetero-dimerization modification; and b) a first light chain, comprising a variable domain having an amino acid sequence substantially identical to that shown in SEQ ID NO:101 and the constant part of a human light chain. The constant part of the human heavy chain may be IgG1. In one embodiment, the IgG1 is a human IgG1 without effector mutations. In one embodiment, the human heavy chain IgG1 comprising a silencing mutation N297A, D265A or a combination of L234A and L235A. In one specific embodiment, the human heavy chain IgG1 comprises the silencing mutation which is a combination of L234A and L235A, according to SEQ ID NO:87.

The second $V_{H2}$ or $V_{L2}$ domain of an IL-18/IL-1β bispecific antibody used in the disclosed methods may have a second $V_{H2}$ and/or first $V_{L2}$ domains that are substantially identical to the $V_H$ or $V_L$ domains set forth in SEQ ID NO:53 and 69. An IL-18/IL-1β bispecific antibody disclosed herein may comprise a second heavy chain that is substantially identical to that set forth as SEQ ID NO:55 and/or a second light chain that is substantially identical to that set forth as SEQ ID NO:71. An IL-18/IL-1β bispecific antibody disclosed herein may comprise a second heavy chain that comprises SEQ ID NO:53 and a second light chain that comprises SEQ ID NO:69. An IL-18/IL-1β bispecific antibody disclosed herein may comprise: a) a second heavy chain, comprising a variable domain having an amino acid sequence substantially identical to that shown in SEQ ID NO:53 and the constant part of a human heavy chain having a hetero-dimerization modification, which is complementary to the hetero-dimerization of the first heavy chain; and b) a second light chain, comprising a variable domain having an amino acid sequence substantially identical to that shown in SEQ ID NO:69 and the constant part of a human light chain. The constant part of the human heavy chain may be IgG1. In one embodiment, the IgG1 is a human IgG1 without effector mutations. In one embodiment, the human heavy chain IgG1 comprising a silencing mutation N297A, D265A or a combination of L234A and L235A. In one specific embodiment, the human heavy chain IgG1 comprises the silencing mutation which is a combination of L234A and L235A, according to SEQ ID NO:55.

Other preferred IL-18 antagonists (e.g. antibodies) for use as the first part of a bispecific antibody in the disclosed methods, kits and regimens are those set forth in U.S. Pat. No. 9,376,489, which is incorporated by reference herein in its entirety.

Other preferred IL-1βantagonists (e.g. antibodies) for use as the second part of a bispecific in the disclosed methods, kits and regimens are those set forth in U.S. Pat. No. 7,446,175 or 7,993,878 or 8,273,350, which are incorporated by reference herein in their entirety.

(1) Vector Design

Two vectors, vector A and vector B, were generated according to the following setup. Vector A was designed for the antibody portion mAb1 (anti-IL18 IgG1). The constant region of the heavy chain 1 was modified by two point mutations, T to W as seen in position 366 of SEQ ID NO: 87, and S to C as seen in position 354 of SEQ ID NO: 87, for generating a knob structure and enabling Cys-bridging. Furthermore, the constant region of the heavy chain 1 was modified by with point mutations, L to A, as seen in position 234 of SEQ ID NO: 87 and L to A as seen in position 235 of SEQ ID NO: 87 (so called LALA), for partial silencing of FC effector functions. The antibody has a variable light region, which is of the lambda 1 type, Vλ1.

Vector B was designed for the antibody portion mAb2 (anti IL-1βIgG1). The constant region of heavy chain 2 was modified by four point mutations T to S as seen in position 366 of SEQ ID NO: 55, L to A as seen in position 368 of SEQ ID NO: 55, Y to V as seen in position 407 of SEQ ID NO: 55, and Y to C as seen in position 349 of SEQ ID NO: 55, for generating a hole structure and enabling an additional Cys-bridging. The hole structure interacts with the knob structure, to facilitate generation of a bispecific antibody. Furthermore, the constant region of heavy chain 2 was modified with the two LALA mutations, L to A as seen in position 234 of SEQ ID NO: 55, L to A as seen in position 235 of SEQ ID NO: 55, for silencing of FC effector functions. The antibody has a variable light region, which is of the kappa 6 type, Vκ6.

Vector A and B carry a combination of DHFR and neomycin selection markers as well as FOLR and hygromycin selection markers, respectively. Folic acid is a vitamin essential for purine and methionine synthesis and needs to be taken up by mammalian cells from the culture medium. The "folic acid receptor" (FoIR) present on the expression plasmid A is a mutant FoIR with altered affinity for folates, facilitating the transport of folic acid from the medium into mammalian cells. Given that high affinity folic acid receptors are only weakly expressed in cultured CHO cells, cells expressing recombinant FoIR have a clear growth advantage under low folate conditions (50 nM). The FoIR selection marker was encoded at vector B In addition to FoIR, "dihydrofolate reductase" (DHFR) is present on vector A as selection marker. DHFR converts folic acid into vital precursors for purine and methionine synthesis. MTX is a chemical analogue of folic acid. It is competing for free binding sites on DHFR and thereby blocking the enzyme. Cells overexpressing exogenous DHFR can deal with elevated MTX concentrations, giving the cells a clear selective advantage growing in medium supplemented with MTX. Combined FoIR and DHFR selection is well known to a person skilled in the art, and disclosed e.g. in the patent document WO2010/097240A1, incorporated here by reference in its entirety. MTX is well known to a person skilled in the art and disclosed e.g. in the patent document WO2010/097239A1, incorporated here by reference in its entirety. Expression vectors are well known to a person skilled in the art, and disclosed e.g. in the patent document WO2009/080720A1, incorporated here by reference in its entirety.

A schematic overview of the two vectors is seen in FIG. 1.

(2) Host Cell Line and Transfection

A parental CHO cell line was used as host cell line for the production of the bbmAb1 expressing cell line. The host cell line was derived from the CHO-K1 cell line, well known to a person skilled in the art, in a way described e.g. in the patent applications WO2015092737 and WO2015092735, both incorporated by reference in their entirety.

A single vial from the CHO line was used to prepare the bbmAb1 recombinant cell line. The CHO line was prepared in chemically defined medium.

The cells were grown in chemically defined cultivation medium.

One μg of SwaI linearized plasmid DNA, expression vector A & B encoding for the bbmAb, was added per transfection. The transfection reaction was performed in chemically defined cultivation medium.

Transfections were performed by electroporation using an AMAXA Gene Pulser, according to the manufactures instructions. The parental CHO cells used for transfection were in exponential growth phase with cell viabilities higher than 95%. In total, three transfections were performed with $5 \times 10^6$ cells per transfection. Immediately after transfection, cells were transferred into Shake Flasks, containing medium chemically defined cultivation medium.

Cell pools were incubated for 48 hours at 36.5° C. and 10% $CO_2$ before starting the selection process.

(3) Cell Selection and Sorting

A selection procedure was carried out using the selection marker encoded by the individual expression vector A and B, as described above. Both proteins (FoIR and DHFR) are participating in the same molecular pathway; the FoIR is transporting folic acid as well as the folate analogue MTX into the cell, the DHFR is converting it into vital precursors for purine and methionine synthesis. Combining them as selective principle, a particular strong selective regime can be taken to enrich for recombinant cells expressing both recombinant protein.

48 h after transfection and growth under low folate conditions, additional selective pressure was applied by adding 10 nM MTX to the chemically defined cultivation medium. 22 days after the start of MTX selection, pool populations consisting predominantly of MTX resistant cells have emerged. After pool recovery cells were frozen and cell pellets prepared. Standard batches in chemically defined cultivation medium were set up for determination of concentration of the bbmAb.

Protein A HPLC methodology was used to determine complete all kind of product and related impurities carrying a Fc part, whereas a reversed phase chromatography (RPC) was use to obtain a fingerprint with respect to the distribution of the individual fractions—individual peaks have been assigned by MS methodology.

CHO cell pools producing bbmAb1 have been used for a FACS cloning procedure to obtain individualized clonal cell lines as starting material for all further evaluations. Cell selection using FACS analysis is described e.g. in the patent application US20110281751, incorporated here by reference in its entirety.

Individual clonal CHO cell lines expressing bbmAb1 were generated by Fluorescent-activated cell sorting (FACS). To enable the FACS sorting the cells were incubated with a FITC-labeled anti IgG1 Fab for 30 min and washed twice in PBS before being used in FACS assisted single cell sorting, a process well known to a person skilled in the art.

FACS cell sorting was performed with a FACS Aria (Becton Dickinson), equipped with an Automatic Cell Deposition Unit (ACDU) using the FACS Diva software.

In order to assure that only single cells were sorted by the FACS instrument, settings were adjusted to single cell precision mode using a nozzle of 130 μm as well as an appropriate flow rate insuring good sorting quality.

In Single Cell mode, the Purity Mask was set to the maximum, so only drops free of particles or further cells were sorted.

The Phase Mask was set to half the maximum, so only particles centered within the sorted drop were deflected.

Drop trajectory and count accuracy were optimized at the expense of yield to increase the probability that each droplet contained not more than 1 single cell.

In order to verify and document monoclonal origin, and to confirm the single cell status at day 0 after FACS cloning images of all wells of the 96 well plates were taken using an imaging system.

The image of day 0 referring to bbmAb1 production clone was visually inspected in duplicate, confirming that only one single cell could be identified in the image of the respective well taken by the imaging system.

This underlined the single cell origin of bbmAb1 production clone.

(4) Cell Expansion

After FACS cloning, the clones were handled by a robotic system for the first weeks and handled manually later on, step wise expanded from 96-well, 24-well towards shaker, and finally bioreactor cultivations, well known to a person skilled in the art, to assess performance (productivity and quality of bbmAb expression).

During the expansion/cultivation recombinant CHO cells were cultivated in chemically defined cultivation medium supplemented with Methotrexate (MTX) at a final concentration of 10 nM.

Cells have been passaged 2-3 times per week into fresh medium and were maintained in logarithmic growth phase throughout the study Productivity was assessed by Protein A HPLC, an initial product quality profile was determined by reversed phase chromatography (RPC).

All frozen stocks were generated in culture medium, supplemented with 7.5% DMSO.

(5) Clone Stability

Isolated bbmAb from pools and clones were carefully evaluated by different analytical methodologies to judge product characteristics and quality parameters to ensure the selection of the best suited production clone.

In addition an excessive analysis of the production stability was performed for the production clones to ensure the selection of the most suitable production clones.

Different state of the art analytical methodologies were used to assess clone stability: affinity liquid chromatography, reverse phase chromatography, FACS and MS.

(6) Manufacturing (a) Upstream Processing bbmAb material was produced either in shake flasks or wave fed batch cultures. Frozen stock of pools or clones such as PSLs were thawed and expanded over the required period of time in chemically defined medium to obtain the required number of cells to seed the production culture, typical with a seed cell density of $4.0 \times 10^5$ cells/ml. The individual culture was cultivated over a period of 13-14 day. During the cultivation in-process controls were performed to monitor the concentration of the bbmAb and the quality profile in the supernatant. At the end of the cultivation process cells were separated from the culture supernatant either by centrifugation (e.g. shaker) or deep filtration followed by sterile filtration before further DSP processing.

(b) Downstream Processing

Based on the format design and the co-expression approach not only the intact product bbmAb1 and common impurities such as aggregates, DNA and host cell proteins, but also mAb1 and mAb2 derived monomers, homodimers and miss-paired light/heavy chain bbmAb1 variants, as shown in FIG. 4, were expected in the supernatant after cell cultivation and cell debris removal. Miss-paired light/heavy chain bbmAb1 variants (FIG. 4E to 4M) are suspected to have the same biophysical properties as the intact bbmAb1 which cannot easily be removed at preparative scale.

Approach I: Purification by Capturing on MabSelect™ SuRe™, Polish on LambdaFabSelect™ and KappaSelect™ bbmAb1 and bbmAb1 variants carrying Fc-part were captured from cell free supernatant by a first affinity liquid chromatography (ALC) step on MabSelect™ SuRe™. bbmAb1 variants containing kappa light chains only (mAb2 hole, FIGS. 4C and 4D) and HCP were removed by a first polish on LambdaFabSelect™ and bbmAb1 variants containing lambda light chains only (mAb1 knob, FIGS. 4A and 4B) and HCP were removed by a second polish step on KappaSelect™.

Chromatography was performed at room temperature using 4 minutes residence time (RT) throughout the method. All columns were equilibrated with 4 column volumes (CV) 20 mM $Na_2HPO_4/NaH_2PO4$, pH 7.0 before loading. To deplete unspecific bound impurities from product, such as host cell proteins (HCP), media components and DNA the chromatography column was washed with 4 CV 250 mM Arginine-HCl, 1 M NaCl, 88 mM NaOH, pH 9.0 and 3 CV equilibration buffer after loading cell-free bbmAb1 supernatant from shakeflask onto the ALC column. bbmAb1 and potential bbmAb1 variants were eluted from the chromatographic column by using 50 mM acetic acid, pH 3.0 respectively 50 mM acetic acid/HCl, pH 2.0 for elution from KappaSelect™ and LambdaFabSelect™. Product peak collection started and ended at 0.5 AU/cm or 0.25 AU/cm (280 nm). The pH of the bbmAb1 eluates were adjusted to ~pH 5.0 with 0.1 or 1 M Tris prior to storage at 2-8° C. respectively for analytical assessment.

Approach II: Purification by Capturing on LambdaFabSelect™, Polish on Capto™ Adhere and Fractogel™ EMD $SO_3$ In a second approach intact bbmAb1 and bbmAb1 variants containing lambda light chains only (mAb1 knob monomer and homodimer, FIGS. 4A and 4B) were captured from cell-free supernatant by affinity liquid chromatography on LambdaFabSelect™. In order to inactivate potentially present enveloped viruses a low pH treatment of the ALC eluate was performed followed by two chromatographic polish steps on Capto adhere and Fractogel™ EMD $SO_3$ to remove product related impurities, DNA and HCP. Potentially present viruses were subsequently removed by nanofiltration prior to a final concentration and buffer exchange step using tangential-flow filtration.

a) Affinity Liquid Chromatography (ALC) on LambdaFabSelect™

ALC was performed at 18-28° C. using 3.6-4.4 minutes residence time (RT) throughout the method. First, the ALC column was equilibrated with 4-6 CV 20 mM $Na_2HPO_4/NaH_2PO4$, pH 7.0. Then clarified cell-free bbmAb1 supernatant from waves or bioreactors was loaded onto the LambdaFabSelect™ column with a loading density of 7-23 g/L. A column wash with 4-6 CV 250 mM Arginine-HCl, 1 M NaCl, 88 mM NaOH, pH 9.0 and a second wash with 3-5 CV equilibration buffer was performed prior to product elution with 4-6 CV 50 mM acetic acid. The product peak was collected from 0.5-2.0 AU/cm (280 nm) ascending and 0.5-2.0 AU/cm (280 nm) descending. The LambdaFabSelect™ column was cleaned using 3-5 CV 120 mM phosphoric acid, 167 mM acetic acid, pH 1.5 prior to re-equilibration with 3-5 CV 20 mM $Na_2HPO_4/NaH_2PO4$, pH 7.0 and storage in 4-6 CV 20% ethanol.

b) Virus Inactivation

The pH of the ALC eluate was adjusted to pH 3.4-3.6 using 0.3 M phosphoric acid. Then the protein solution was subsequently incubated for 60-90 min at this low pH before pH adjustment to 7.3-7.7 with 1M Tris. A depth filtration step using Millipore B1HC Pod filters was used applying a flow rate of 100-300LMH before sterile filtration with 0.45/0.2 µm Sartopore™ sterile filter.

c) Multimodal Anion Exchange Chromatography (MAC) on Capto™ Adhere

MAC was performed in flow-through mode at 18-28° C. using 4-6 minutes residence time throughout the method. First, the MAC column was equilibrated with 7-9 CV 20 mM Tris/Tris-HCl, pH 7.5. Then the low pH treated ALC eluate was loaded onto the Capto™ adhere column using a loading density of 175-350 g/L. Product peak collection started thereby at 0.5-2.0 AU/cm (280 nm) ascending. Then the MAC column was washed with 5-7 CV equilibration buffer and product peak collection ended at 0.5-2.0 AU/cm (280 nm) descending. The Capto™ adhere column was subsequently stripped with 6-8 CV 100 mM acetic acid, followed by a cleaning-in place step with 3-5 CV 0.5 M NaOH and storage in 3-5 CV 0.1 M NaOH.

d) Cation Exchange Chromatography on Fractogel™ EMD $SO_3$.

CEC on Fractogel™ EMD $SO_3$ was performed in bind-elute mode at 18-28° C. A residence time of 6-8 minutes was used during equilibration, strip, CIP and storage and 8-10 min residence time during load, wash and elution. The CEC column was equilibrated with 6-8 CV 20 mM succinic acid, 35.1 mM NaOH, pH 6.0. Then the MAC percolate was loaded onto the column with a loading density of 35-70 g/L. Subsequently, the CEC column was washed with 5-7 CV equilibration buffer. Elution was performed using a linear salt gradient from 10 to 90% 20 mM succinic acid, 500 mM NaCl, 37.4 mM NaOH, pH 6.0 over 15 CV. The bbmAb1 product peak was collected starting at 0.1-0.4 AU/cm ascending to 20%-40% maximum peak height at 300 nm. The Fractogel™ EMD $SO_3$ column was stripped with 3-5 CV 1 M NaCl, followed by a cleaning-in place step with 3-5 CV 0.5 M NaOH and storage in 3-5 CV 0.1 M NaOH.

e) Nanofiltration

Potentially present viruses were removed by nanofiltration using Planova™ 20N nanofilter and a 0.5/0.1 µm Millipore SHR-P pre-filter. Pre- and nanofiltration was performed by applying a differential pressure of 0.7-0.9 bar.

f) Tangential-Flow Filtration and Formulation

In order to concentrate and diafiltrate bbmAb1 a tangential-flow filtration step on Millipore™ Pellicon™ 3 RC 30 kDa membranes was performed at 18-28° C. First, the nanofiltered bbmAb1 protein solution was concentrated with a maximum loading density of 1000 g/m² to 60-80 g/L using a feed flow pressure of 0.5 to 1.2 bar and a transmembrane pressure (TMP) of 0.3-0.6 bar. Then, bbmAb1 was diafiltered against 7-9 diafiltration volumes 20 mM histidine/histidine-HCl, pH 6.0 at a feed flow pressure of 0.8 to 1.8 bar and a TMP of 0.4-0.9 bar. A second concentration step to 134±10 g/L at a feed flow pressure of 1.4-3.0 bar and a TMP of 0.7 to 1.5 bar was performed The ultrafiltered bbmAb1 protein solution was finally formulated to a concentration of 100±10 g/L and 0.04% (w/v) Polysorbat 20. The final drug substance (DS) is filtered through a 0.2 µm filter is stored frozen at ≤−60° C.

(7) Analytical Characterization and Purity Assessment (a) LC-MS Screening of Intact bbmAbs and Variants 100 pg of protein-A purified bbmAb samples were lyophilized in a 96-well plate and de-glycosylated by PNGaseF (New England Biolabs) for 18 hours at 37° C. in 100 µl of 50 mM Tris-HCl pH 7.5) buffer. Samples were measured by LC-ESI-MS on an H-Class UPLC (Waters) connected to a Synapt G2 Q-TOF mass spectrometer (Waters). MassPREP Micro Desalting column 2.1×5 mm (Waters) was used at 80° C. column temperature. A linear gradient was applied at 0.3 ml/min with mobile phase A: 0.1 formic acid in water, mobile phase B: 0.1% FA in acetonitrile: 0-2 min 5% B, 2-12 min 5-90% B, followed by several wash steps at 0.5 ml/min. MS parameters: ESI+Resolution mode, Capillary voltage 3 kV, sampling cone 40 V, source temperature 150° C., desolvation temperature 400° C. System was calibrated with NaCl calibration solution, lock mass was Leucin Enkephalin. Data was processed by automatic MaxEnt1 deconvolution (mass range 60-150 kDa, harmonic suppression) with UNIFI 1.6 software (Waters). Identification and relative quantification of bbmAb species and miss paired variants is based on the match to the theoretically expected mass and the relative mass signal intensity of the de-convoluted mass spectrum.

(b) LC-MS Characterization of bbmAb1

Intact De-Glycosylated bbmAb:

Purified bbmAb1 antibody was diluted in 20 mM Tris-HCl pH 7.5 to 1 mg/ml and was de-glycosylated for 4 h at 37° C. using 2 µl PNGaseF enzyme (New England Biolabs). The digestion was stopped by adding trifluoroacetic acid (TFA) to 2%.

Reduced De-Glycosylated bbmAb:

bbmAb1 was diluted to 5 mg/ml in 20 µl 0.1 M Tris-HCl pH 7.5. 2 µl of PNGase F was added and incubated for 4 h at 37° C., then 80 µl of denaturation buffer (50 mM Tris-HCl pH 8.0, 6 M guanidine hydrochloride) and 1 µl of 1 M DTT was added to the mixture. After incubation for 1 hour at 37° C., the sample was acidified with 1 µl TFA.

Papain Digestion of bbmAb into Fab and Fc.

bbmAb1 was mixed with digestion buffer (20 mM succinic acid, 35.1 mM NaOH, pH 6.0, 1 mM Cys-HCl, 1 mM EDTA) to 5 mg/ml, then papain protease (Roche, Germany) was added to final concentration of 5 pg/ml (protease/protein ratio 1:1000) and incubated for 2 hours at 37° C. under shaking. After incubation, the solution was stopped by adding iodoacetamide solution to 1.2 mM final concentration.

IdeS digestion of bbmAb to F(ab')$_2$ and Fc.

100 pg bbmAb1 were mixed with cleavage buffer (50 mM sodium phosphate, 150 mM NaCl, pH 6.6) and digested with 100 U IdeS protease (Fabricator, Genovis) overnight at 37° C. After incubation, the solution was stopped by adding TFA to 2% final concentration.

Reduced LysC Digestion—Peptide Mapping.

(According to Rombach-Riegraf et al, PlosOne 2014) 200 pg protein were denatured using 150 µl of denaturing solution (6 M guanidine hydrochloride, 50 mM Tris-HCl, 5 mM Na$_2$EDTA, pH 8.0) and reduced by adding 1.5 µl of 1 M DTT and incubation at 37° C. for one hour. The alkylation was performed by adding 3 µl of 1 M iodoacetamide followed by incubation at 37° C. in the dark. The reaction was quenched with 1 µl of 1 M DTT. Following reduction/alkylation, 750 µl digestion buffer (50 mM Tris-HCl, pH 8) were added to the sample. The sample was then digested by two additions of 4 µl of a 1 µg/µl endoproteinase LysC solution (Wako (Osaka, Japan)) and incubation at 37° C. for 1 hour and 3 hours respectively. 5 µl TFA was added to quench the digestion.

LC-Ms Measurements.

Protein samples were subjected to LC-MS system using Waters UPLC H-Class equipped with a BEH C4 RP column (1.7 µm, 2.1×100 mm, 300 Å, Waters) and a Xevo G2 TOF mass spectrometer (Waters, Milford). Eluents were A: 0.1% TFA in water and B: 0.09% TFA in acetonitrile. The column was set to 80° C. Flowrate was 0.2 ml/min. Proteins were eluted with a 40 min gradient as follows: 0-5 min 10% B, 5-10 min 10-30% B, 10-25 min 30-40% B, 25-26 min 40-95% B, 26-28 min 95%, 28-40 min 10% B.

MS settings: ESI (+) TOF mode, Resolution mode, Mass Range 400-4000 Da, Scan Time 1s, capillary voltage 3 kV, sampling cone 25 V-40 V. System was calibrated using NaCsI solution.

Peptide digests were analyzed by RP-LC-MS on H-Class UPLC (Waters) coupled to a Synapt G2 Q-TOF mass spectrometer (Waters) using an CSH130 C18 2.1 mm×150, 1.7 μm (Waters, Milford). Mobile phase A: 0.1% TFA in water and mobile phase B: 0.09% TFA in acetonitrile. Peptides were eluted from the column with a following gradient: 0-5 min 0% B, 5-10 min 0-2% B, 10-40 min 2-20% B, 40-120 min 20-40% B, 120-135 min 40-70% at 40° C. column temperature. UV chromatograms were recorded at 214 nm and MS data acquisition was performed in positive ES(+) resolution mode as an MSE experiment using low energy (4 eV) and high energy fragmentation (30-55 V). Lock mass was Leucin Enkephalin (Waters).

Data processing and evaluation was performed by Mass-Lynx 4.2 or UNIFI 1.6 software (Waters). MaxEnt1 algorithm was used for deconvolution of protein mass spectra. Theoretical mass calculations were performed with GPMAW 9.2 software (Lighthouse data).

(c) Reversed Phase Chromatography bbmAb samples were analyzed on Agilent 1260 HPLC using Poroshell 300 SB-C8 RP column, 2.1 mm×75 mm, 5 μm (Agilent). Column temperature was set to 80° C., flow rate was 2 ml/min, mobile phase A: 90% water, 10% acetonitrile, 0.1% TFA, 0.3 PEG-300, mobile phase B: 10% water, 90% acetonitrile, 0.1% TFA, 0.3% PEG-300. Gradient used was: 0-5 min 22-37% B, 5.0-5.1 min 100% B, 5.1-6 min 100% B, 6.1.-8.5 min 22% B. UV signal was recorded at 210 nm. Data acquisition and evaluation was controlled and performed using Chromeleon™ 6.8 software (Thermo Scientific).

(d) Size Exclusion Chromatography bbmAb1 sample were subjected to TSK gel G3000SWXL (Tosoh #808541, 5 μm, 7.8 mm×300 mm) SEC column, pore size 250 A using an Agilent 1260 system. Mobile phase was 150 mM potassium phosphate solution, pH 6.5, Flow rate was 0.4 ml/min, column temperature was 30° C. UV was recorded at 210 nm. Data acquisition and peak integration was performed using Chromeleon™ 6.8 (Thermo Scientific).

(e) Capillary Electrophoresis CE-SDS

For non-reducing CE-SDS, bbmAb sample was mixed with sample buffer (0.1 sodium phosphate/1.0% SDS, pH 6.6) and then mixed with iodoacetamide solution. For reducing CE-SDS, the protein was mixed with 0.1 M Tris/1% SDS sample buffer, pH 8.0 and reduced with 5% (v/v) mercaptoethanol. Both samples underwent a heat denaturation step at 70° C. for 10 minutes.

Samples were analyzed on a Beckman PA 800 system equipped with a bare fused silica capillary (50 μm, 375 OD, 67 cm, Beckman) with of 30 cm total capillary length and filled with Beckman SDS MW sieving gel buffer. Separation was done from negative to positive polarity at 15 kV and 25° C. capillary temperature, detection by UV at 214 nm. Electropherograms were processed and integrated using Chromeleon™ 6.8 software.

(f) Capillary Zone Electrophoresis CZE

Separations were performed on a Beckman Coulter PA 800 Pharmaceutical Analysis System equipped with 214 nm UV detector. Protein was separated on fused silica capillary (50 μm ID) of a total length of 40 cm with a capillary voltage of 20 kV at 25° C. and positive polarity. Running buffer: 400 mM 6-aminocaproic acid/acetic acid pH 5.7 with 2 mM TETA and 0.03% Tween 20. Peak integration was performed with Chromeleon™ 6.8 software.

(8) Analytical Results

The purity and identity of different bispecific antibody combinations and constructs after co-expression was analyzed after protein-A purification using an intact UPLC-MS mass screening approach. This approach was used to confirm and relatively quantify the formed hetero- and homodimers from cell supernatant. Correctly formed heterodimeric bbmAb1 and bbmAb2 could be observed with a relative purity of over 85% based on intact mass signal intensity. Main impurities observed in the screen were the miss paired antibody with two kappa light chains, two lambda light chains and HC hole-dimer molecules.

TABLE 4

Summary of analytical results obtained for bbmAb1-bbmAb11.

| Candidate | Knob/Hole | L1/L2 | Bispecific Ab variants identity by MS | | Ranking |
|---|---|---|---|---|---|
| | | | ID | Rel. Quantification | |
| bbmAb1 | mAb1/ mAb2 | mAb1 (l)/ mAb2 (k) | bsAb KH:L2L2 KH:L1L1 | 85% 5% 10% | 1 |
| bbmAb2 | mAb2/ mAb1 | mAb1 (l)/ mAb2 (k) | bsAb KH:L1L1 KH:L2L2 | 84% 6% 10% | 1 |
| bbmAb3 | mAb3/ mAb4 | mAb3 (k)/ mAb4 (k) | bsAb KH:L1L1 HH:L1L1 (H dimer) | 54% 35% 11% | 2 |
| bbmAb4 | mAb5/ mAb2 | mAb2 (k)/ mAb5 (l) | bsAb KH:L2L2 HH:L1L1 (H dimer) KH:L2L2 | 63% 9% 11% 17% | 2 |
| bbmAb5 | mAb1/ mAb6 | mAb6 (k)/ mAb1 | bsAb HH:L2L2 (H dimer) | 53% 47% | 2 |
| bbmAb6 | mAb7/ mAb1 | mAb1 (l)/ mAb7 (k) | bsAb KH:L2L2 KH:L1L1 HH:L1L1 (H dimer) | 51% 21% 20% 9% | 3 |
| bbmAb7 | mAb8/ mAb1 | mAb8 (l)/ mAb1 (l) | bsAb HH:L2L2 (H dimer) Partial Ab: H:L2, H:L2 + Cys | 80% 20% | 2 |
| bbmAb8 | mAb9/ mAb1 | mAb9 (k)/ mAb1 (l) | bsAb KH:L2L2 KH:L1L1 HH:L2L2 (H dimer) | 35% 34% 17% 14% | 3 |
| bbmAb9 | mAb10/ mAb1 | mAb10 (k) /mAb1 (l) | bsAb KH:L1L1 HH:L1L1 (H dimer) KH:L2L2 | 58% 23% 12% 7% | 3 |
| bbmAb10 | mAb11/ mAb1 | mAb11 (k)/ mAb1 (l) | bsAb KH:L1L1 HH:L1L1 (H dimer) bsAb HC clip Partial Ab: H:L1, H:L1 + Cys | 45% 22% 23% 10% | 2 |

TABLE 4-continued

Summary of analytical results obtained for bbmAb1-bbmAb11.

| Candidate | Knob/Hole | L1/L2 | Bispecific Ab variants identity by MS | | |
|---|---|---|---|---|---|
| | | | ID | Rel. Quantification | Ranking |
| bbmAb11 | mAb12/mAb1 | mAb12 (k)/mAb1 (l) | bsAb | 49% | 2 |
| | | | HH:L1L1 (H dimer) | 41% | |
| | | | KH:L1L1 | 10% | |
| | | | Partial Ab: H:L1, H:L1 + Cys | | |

Designation I is lambda chain, k is kappa chain.
mAb3 is an antibody of type VH3, Vk1.
mAb4 is an antibody of type VH3, Vk1.
mAb5 is a graft version of mAb1 (VH1, Vl1).
mAb6 is a graft version of mAb2 (VH1_46, Vk3).
mAb7 is an antibody of type VH3, Vk1.
mAb8 is an antibody of type VH1_2, Vk2.
mAb9 is an antibody of type VH5, Vk6.
mAb10 is an antibody of type VH1_46, Vk6.
mAb11 is an antibody of type VH3, Vk3.
mAb12 is an antibody of type VH3, Vk2.

bbmAb1 was characterized in more detail to evaluate the all formed product variants and impurities after the different purification steps by LC-MS using several sample preparation methods, and with other separation techniques. The mass of the intact 2-step (lambda/CEC) purified product was determined after de-glycosylation with PNGaseF enzyme and subsequent injection into the RP-LC-MS setup. The de-convoluted mass spectrum of intact bbmAb1 confirmed the correct formation of the knob-in-hole heterodimer after co-expression and lambda-select purification. No major impurities like homodimers or partial antibodies could be detected after lambda-select purification. Identity of the four different antibody chains could be confirmed after reduction and de-glycosylation of the sample.

To check for chain mispairing and other low level impurities, the purified sample was digested by papain protease to analyze the individual Fab and Fc fragments. The measured masses of the fragments confirmed again the correct formation of the different Fab arms (Knob-lambda, Hole-kappa), as well as the correct formation of the knob-in-hole Fc fragment. A mispaired Fab fragment (Fab4, Knob-kappa) could be observed in levels <1%. An alternative approach the generate Fab fragments with a limited LysC digestion was tested which allows faster sample prep during pool and clone selection.

Another digestion strategy using IdeS (Fabricator) enzyme was tested to generate Fc and F(ab')2 fragments. In this experiment, the mass of the Fc heterodimer was observed and the correctly formed heterodimeric F(ab')2. The presence of a Fc heterodimer is also proof of the correct formation of the additional di-sulfide bridge in Fc part of bbmAb1, as otherwise only a Fc/2 fragment of smaller mass would be generated.

LysC peptide mapping with LC-MS could confirm identity of the molecule with an overall sequence coverage of the peptides of 99%.

Specific results of the purified samples are shown in FIG. 2. Particularly, RP-UV chromatogram of de-glycosylated intact bispecific mAb is shown in FIG. 2A. Papain digested bbmAb1 fragments are shown in FIG. 2C. IdeS digested bbmAb1 fragments are shown in FIG. 2D. De-glycosylated and DTT reduced bbmAb1 fragments are shown in FIG. 2E. De-convoluted mass spectrum of the intact deglycosylated bispecific mAb bbmAb1 is shown in FIG. 2B.

Results are shown in Table 5.

TABLE 5

Assignment of measured bbmAb1 masses by RP-LC-MS

| bbmAb1 | Identity | Observed mass (Da) | Theoretical mass (Da) | Mass deviation (Δ Da) |
|---|---|---|---|---|
| Intact deglycosylated bsAB | L1H1:L2H2 mAb | 144104 | 144101 | +4 |
| Papain digest | Fc (H1-H2)+ bG0/bG0/0K | 52570 | 52570 | 0 |
| | Fab1 (L1H1 lambda/knob) | 46952 | 46952 | 0 |
| | Fab2 (L2H2 kappa/hole) | 47503 | 47504 | −1 |
| | Fab4 | 47329 | 47330 | +1 |
| IdeS digest | F(ab')2 | 96644 | 96643 | +1 |
| | Fc (H1-H2) dimer + bG0/bG0/0K | 50383 | 50383 | 0 |
| Reduced deglycosylated bsAb | L1 (λ-LC) | 22980 | 22980 | 0 |
| | L2 (κ-LC) pyro-E | 23358 | 23358 | 0 |
| | H1 (knob-CH) 0K | 48953 | 48952 | 1 |
| | H2 (hole-CH) pE, 0K | 50290 | 50289 | 1 |

Figure 3C:
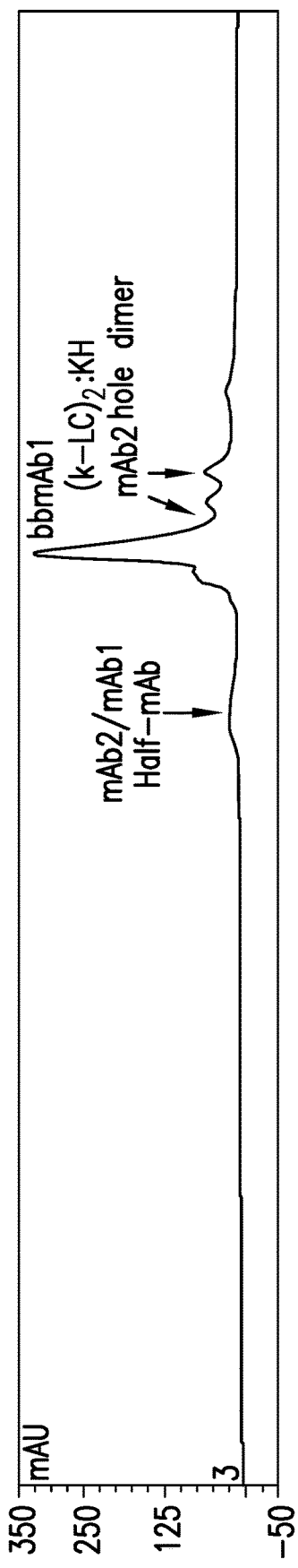
Figure 3D:
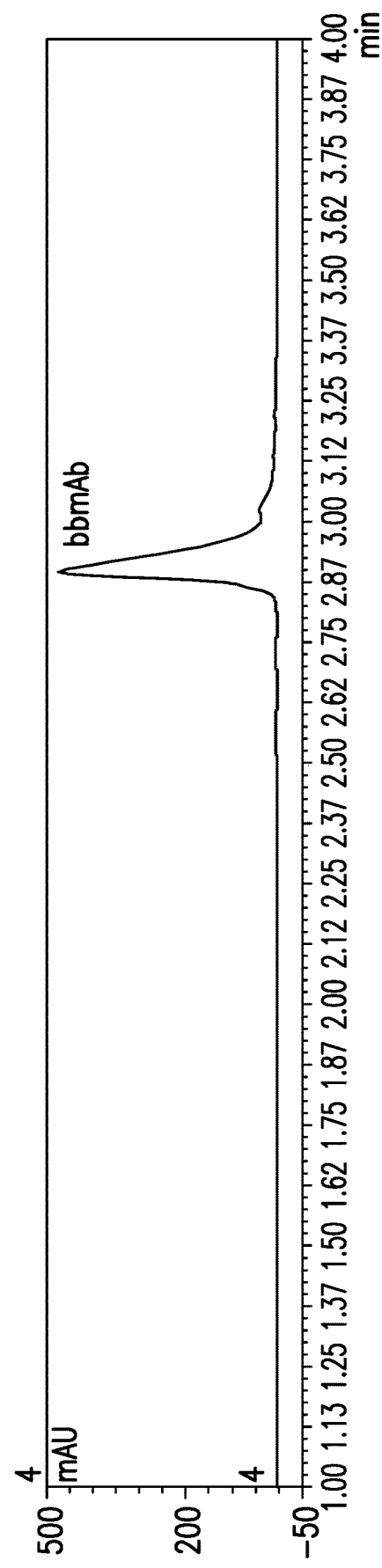
Figure 4A:
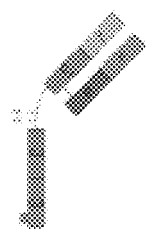
FIG. 4A-4M is a schematic overview of different options for bispecific mismatching.
Figure 4B:
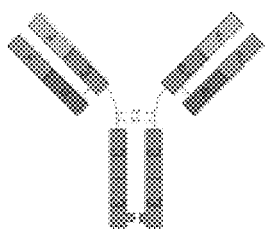
Figure 4C:
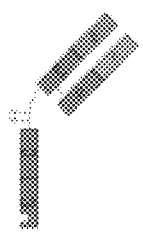
Figure 4D:
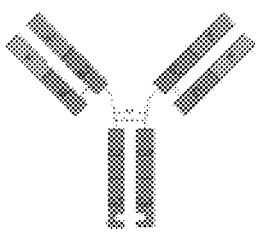
Figure 4E:
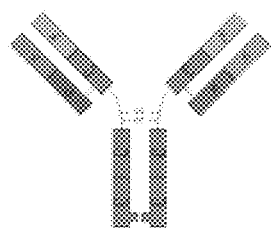
Figure 4F:
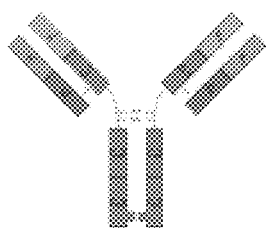
Figure 4G:
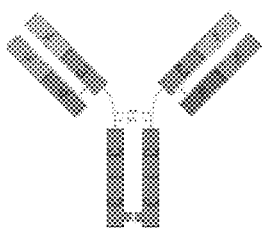
Figure 4H:
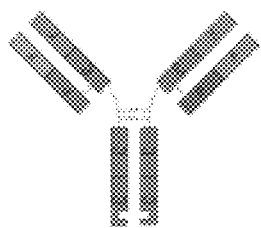
Figure 4I:
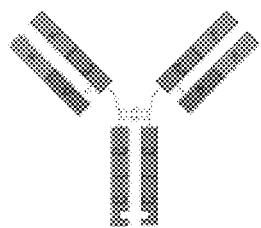
Figure 4J:
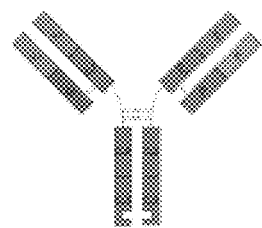
Figure 4K:
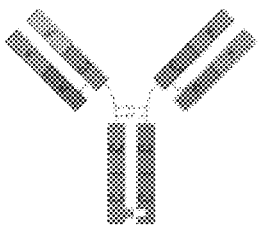
Figure 4L:
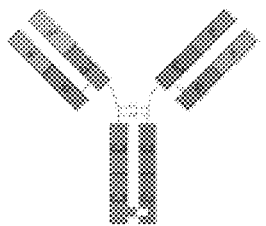
Figure 4M:
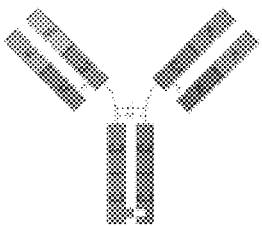

The increased purity obtained after applying different steps described above is seen in FIG. 3. FIG. 3A is a chromatogram showing the expression profile after cultivation, FIG. 3B is a chromatogram after capturing by Lambda-FabSelect™, FIG. 3C is a chromatogram after capturing with MabSelect™ SuRe™, and FIG. 3D is a chromatogram after capturing with LambdaFabSelect™, polish by Fractogel™ EMD SO3 and ultrafiltration.

The final 2-step purified (lambda/CEC) bispecific bbmAb1 was further analyzed by methods listed in Table 6. Overall the material shows high purity with low level of aggregates or degradation products as detected by several separation methods such as size exclusion chromatography (SEC), CE-SDS and capillary zone electrophoresis (CZE).

TABLE 6

Purity analytics of purified bbmAb1

| Method | Parameter | Value |
|---|---|---|
| Purity by SEC | Aggregation Products | 1.3% |
| | Degradation Products | 1.2% |
| CZE | Acidic Species | 24.7% |
| | Basic Species | 16.6% |
| Purity by CE-SDS | Reducing | 98.2% |
| | Non-reducing | 94.6% |

Additional combinations of other antibodies have been tested as well. Table 4 shows a summary of analytical results obtained.

6. Example 2: In Vitro Activity of bbmAb1

Binding activity of bbmAb1 was tested in a variety of different cell assays.
(1) Materials and Methods
(a) For Solution Equilibrium Titration (SET) Assays
The following material was used:
Recombinant human IL-18, biotinylated (BTP25828)
Recombinant Cynomolgus monkey IL-1β(Novartis)
Anti-human IgG antibody, SULFO-TAG labeled (Meso Scale discovery (MSD) #R32AJ-5)
Goat anti-human Fab specific, conjugated with MSD SULFO-TAG NHS Ester (Jackson
Immuno Research #109-005-097, MSD #R91AN-1) BSA (Sigma #A-9647)
MSD read buffer T with surfactant (MSD #R92TC-1)
Phosphate-buffered saline (PBS) 10×(Teknova #P0195)
Tris-buffered saline, pH 7.5
(TBS) 10×(Teknova #T1680) Tween-20 (Fluke #93773)
Polypropylene microtiter plate (MTP) (Greiner #781280)
384-well plates, standard (MSD #L21XA)
(b) For Cellular Assays and SET Assays
mAb2 as described in section IL-1βantibody.
mAb1 as described in section IL-18 antibody.
bbmAb1 as described in Example 1.
Recombinant human IL-18 (BTP 25829) purchased from MBL Int. Corp. (#6001-5)
Recombinant marmoset IL-1β(Novartis)
Recombinant marmoset IL-18 (Novartis)
Recombinant human IL-12 (#573008) was purchased from Biolegend KG-1 cell line (ATCC #CCL-246)
Normal human dermal fibrobasts (#CC-2509) were purchased from Lonza
Marmoset skin fibroblasts (#42637F (510))
HEK-Blue™ IL-18/IL-1β cells (#hkb-i118) were purchased from InvivoGen
PBMC were isolated from buffy coats were obtained from the Blutspendezentrum Bern Marmoset blood was obtained from SILABE, Niederhausbergen IL-6 ELISA: Human (BioLegend, #430503); Marmoset (U-CyTech biosciences, CT974-5)
IFNγ ELISA: Human (BD555142) and marmoset (U-CyTech biosciences #CT340A)
QUANTI-Blue™ assays (#rep-qb1) for the detection of SEAP was purchased from InvivoGen
Cell medium: RPMI 1640 (Invitrogen #31870) supplemented with 10% Foetal Bovine Serum (Invitrogen #10108-157), 1% L-Glutamine (Invitrogen #25030-03), 1% penicillin/streptomycin (Invitrogen #15140-148), 10 pM 2-Mercaptoethanol (Gibco #31350-010), 5 mM Hepes (Gibco #15630-080)
Round-bottomed, tissue-culture treated 96-well plates (Costar #3799)
Flat-bottomed, tissue-culture treated 96-well plates (Costar #3596)
Ficoll-Pacque™ Plus (GE Healthcare Life Sciences #17-1440-02) PBS 1X, without Calcium & Magnesium (Gibco #14190094)
Leucosep tubes with porous barrier, 50 ml, polypropylene (Greiner bio-one #227290)
Falcon 15 ml polypropylene conical tubes (BD #352096)
Falcon 50 ml polypropylene conical tubes (BD #352070)
(c) Affinity Measurements by SET
SET Individual Target Binding Assay
22 serial 1.6n dilutions of the antigens (highest conc.: huIL-18, 5 nM; marIL-18, 10 nM; huIL-1β, 0.5 nM; marIL-1β, 0.5 nM) were prepared in sample buffer (PBS containing 0.5% Bovine serum albumin (BSA) and 0.02% Tween-20) and a constant concentration of antibody was added (for IL-18 readout 10 pM, for IL-1βreadout 1 pM). A volume of 60 µl/well of each antigen-antibody mix was distributed in duplicates to a 384-well polypropylene microtiter plate (MTP). Sample buffer served as negative control and a sample containing only antibody as positive control (Maximal electrochemiluminescence signal without antigen, $B_{max}$). The plate was sealed and incubated overnight (o/n, at least 16 h) at room temperature (RT) on a shaker.

IL-18 readout: A streptavidin coated 384-well MSD array MTP was coated with 30 µl/well biotinylated huIL-18 (0.1 pg/ml, PBS) and incubated for 1 h at RT on a shaker.
IL-1βreadout: A standard 384-well MSD array MTP was coated with 30 µl/well of huIL-1 (3 pg/ml, PBS) diluted in PBS as capture agent and incubated overnight at 4° C.

The plate was blocked with 50 µl/well blocking buffer (PBS containing 5% BSA) for 1 hour (h), at room temperature (RT). After washing (TBST, TBS containing 0.05% Tween 20), a volume of 30 µl/well of the equilibrated antigen-antibody mix was transferred from the polypropylene MTP to the coated MSD plate and incubated for 20 min at RT. After an additional wash step, 30 µl sulfo tag-labeled anti-IgG detection antibody (0.5 µg/ml) diluted in sample buffer were added to each well and incubated for 30 min at RT on a shaker. The MSD plate was washed and 35 µl/well MSD read buffer were added and incubated for 5 min at RT. Electrochemiluminescence (ECL) signals were generated and measured by the MSD Sector Imager 6000.

SET Simultaneous Target Binding Assays

The SET assay was performed a described above, except for Assay A: The equilibration process (antibody/antigen mix) was performed in presence of an excess of one target (500 pM of either IL18 or IL-1β) while assessing the $K_D$ of the other target. Assay B: The equilibration process (antibody/antigen mix) was performed with both targets in serial dilutions in one mix simultaneously (constant concentration of antibody 10 pM, highest antigen conc. see above). The same mix was then analyzed for its free antibody concentration on IL18 and IL-1β coated plates as described above.

The SET Data were exported to Xlfit, an MS Excel add-in software. Average ECL-signals were calculated from duplicate measurements within each assay. Data were baseline adjusted by subtracting the lowest value from all data points and plotted against the corresponding antigen concentration to generate titration curves. $K_D$ values were determined by fitting the plot with the following:

1:2 Binding Model for the Monospecific Ab $$y = \frac{2B_{max}}{[IgG]}\left(\frac{[IgG]}{2} - \frac{\left(\frac{y+[IgG]+K_D}{2} - \sqrt{\frac{(x+[IgG]+K_D)^2}{4} - x[IgG]}\right)^2}{2[IgG]}\right)$$

1:1 Binding Model for the Knob in Hole Bispecific Ab $$y = B_{max} - \left(\frac{B_{max}}{2[Fab]}\left([Fab] + x + K_D - \sqrt{([Fab]+x+K_D)^2 - 4x[Fab]}\right)\right)$$

wherein
y: blank subtracted ECL signal
$B_{max}$: maximal ECL signal at zero antigen concentration
[IgG]: applied antibody concentration
[Fab]: applied total Fab concentration
$K_D$: Dissociation equilibrium constant
x: applied antigen concentration (d) Cell Culture KG-1 cells were grown in RPMI 1640 supplemented with 10% fetal bovine serum, 1% L-Glutamine and 1% penicillin/streptomycin at a density of $2 \times 10^5$ to $1 \times 10^6$ viable cells/mL. Normal human fibroblasts and marmoset fibroblasts were grown in FBM (Clonetics, CC-3131) including bFGF (1 ng/ml, CC-4065), insulin (5 µg/ml, CC-4021), and 2% FCS (CC-4101). As starving medium, Fibroblast Basal Medium (LONZA #CC-3131) was used.

HEK-Blue™ IL-18/IL-1β cells were grown in Growth Medium (DMEM, 4.5 g/l glucose, 10% (v/v) fetal bovine serum, 50 U/ml penicillin, 50 mg/ml streptomycin, 100 mg/ml Normocin™, 2 mM L-glutamine supplemented with 30 µg/ml of Blasticidin, 200 µg/ml of HygroGold™ and 100 µg/ml of Zeocin™

Human peripheral blood mononuclear cells (PBMC) were freshly isolated from buffy coats using LeucoSep tubes according to the instructions of the manufacturer. In brief, 13 ml of Ficoll-Paque was preloaded in a 14 ml LeucoSep tube by centrifugation for 30 s at 1,000×g. The heparinized whole-blood samples were diluted with equal volumes of PBS, and 25 ml of the diluted blood was added to a LeucoSep tube. The cell separation tubes were centrifuged for 15 min at 800×g without break at room temperature. The cell suspension layer was collected, and the cells were washed twice in PBS (for 10 min at 640 and 470×g, respectively, for the two successive washes) and re-suspended in culture medium before counting.

Marmoset blood was collected in heparinized tubes and filtered using a 70 µm cell strainer (BD Biosciences #352350)

(e) IL-1β Neutralization Assays

The IL-1β induced IL-6 production assay in fibroblasts was conducted essentially as described (Gram 2000) with only minor modifications. Briefly, fibroblasts were seeded at a density of 5×103 cells per well (in 100 µl) in a 96 well flat bottom tissue culture plate. The following day, cells were starved for 5 h in starving medium before addition of the recombinant IL-1β/compound solution mix (IL-1β concentration indicated in the table). The IL-1β/compound solution mix was prepared beforehand by incubating recombinant IL-1β with a concentration range of compound for 30 min at 37° C. The cell supernatants were collected after o/n incubation at 37° C. and the amount of released IL-6 determined by ELISA. The IL-1βinduced IL-6 production assay in PBMC was performed according to the following. PBMC were seeded at $3 \times 10^5$ cells per well (in 100 µl) in a 96 well tissue culture plate and incubated with a recombinant IL-1β/compound solution mix for 24 h at 37° C. (IL-1β concentration indicated in the table). The IL-1β/compound solution mix was prepared beforehand by incubating recombinant IL-1β with a concentration range of compound for 30 min at 37° C. The cell supernatants were collected after 24 h of stimulation and the amount of released IL-6 determined by ELISA.

(f) IL-18 Neutralization Assays

The assay was conducted essentially according to the following. KG-1 cells (starved for 1 h in PBS+1% FCS beforehand) or PBMC at a density of $3 \times 10^5$ per well were seeded into round bottom 96-well cell culture plates and incubated with a solution mix of recombinant IL-18/IL-12 together with a concentration range of compounds (IL-18/IL-12 concentrations indicated in the table). After an incubation of 24 h at 37° C., supernatants were collected and the amount of released IFNγ determined by ELISA. For the assays with marmoset blood 85 µl of blood per well were used.

(g) Dual IL1β/IL-18 Neutralization in HEK-Blue™ Cells

The assay was conducted essentially as described in the manufacturer's handling procedures. Briefly, the HEK-Blue™ cells were seeded at a density of $4 \times 10^4$ per well into 96-well cell culture plates and incubated with a solution mix of recombinant IL-1β and IL-18 (to produce a 1:1 SEAP signal) together with a concentration range of compounds. After an incubation of 24 h at 37° C., supernatants were collected and the amount of released SEAP determined by using the QUANTI-Blue™ method according to the manufacturer's instructions.

All Data were exported to EXCEL software and IC50 values calculated by plotting dose-response curves for the logistic curve fitting functions using either EXCELJXLfit4 or GraphPad Prism software.

(2) Results (a) Affinities to Recombinant Human and Marmoset IL1β and IL-18

Figure 5A:
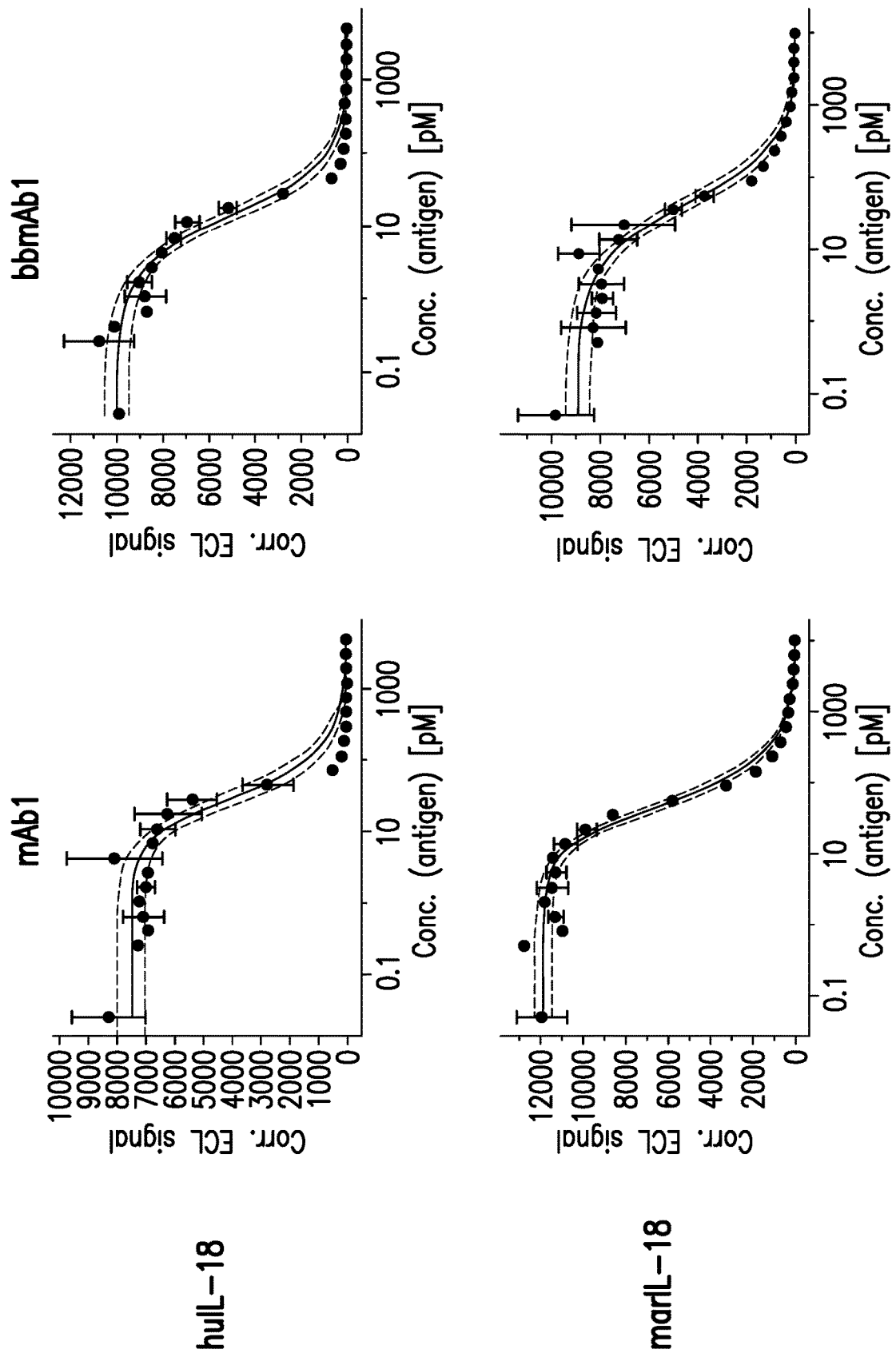
FIG. 5 shows titration curves of ECL-based affinity determination according to an Example.
Figure 5B:
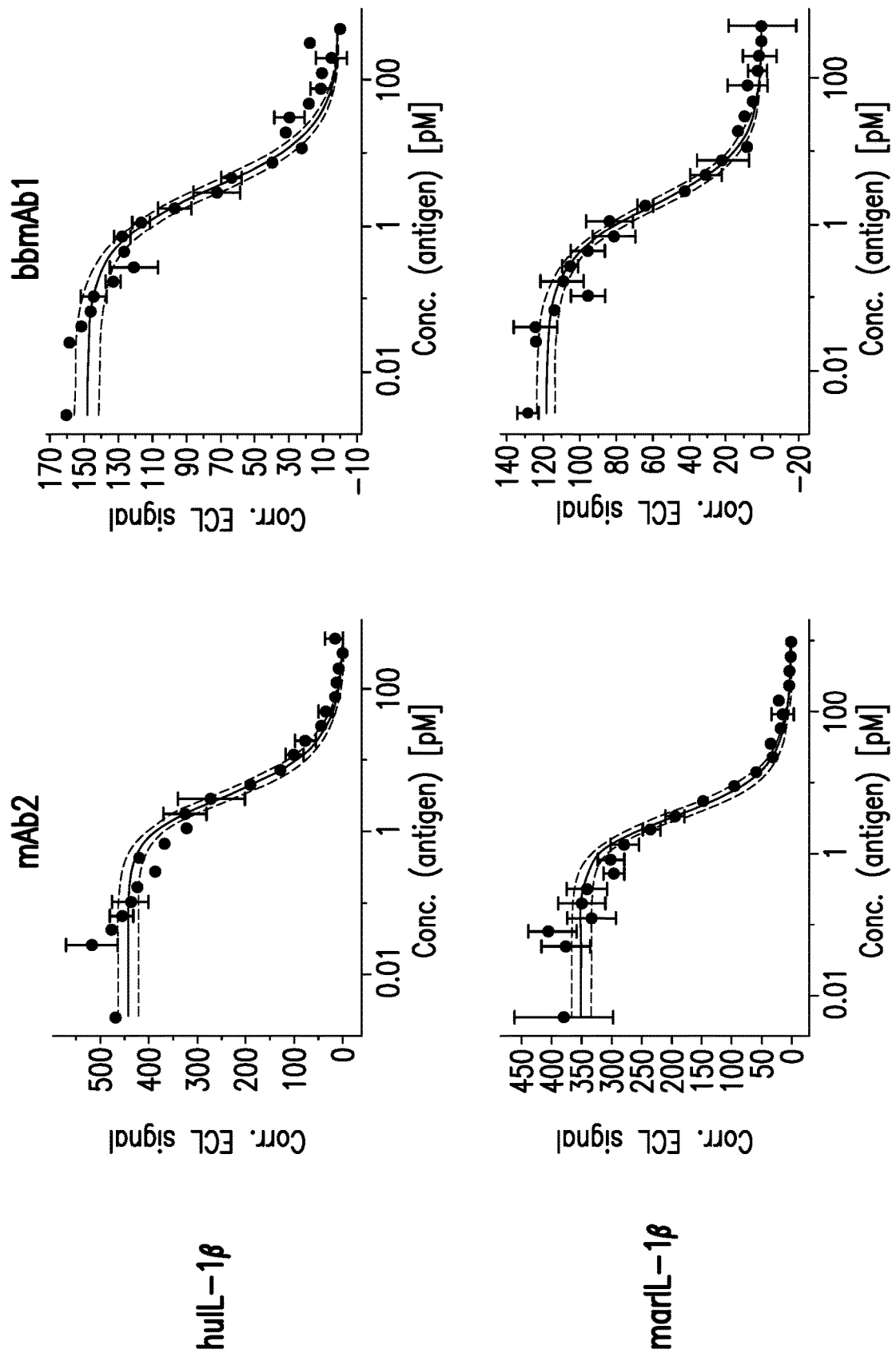

Binding affinities of bbmAb1 to human and marmoset recombinant IL-1β and IL-18 proteins were measured by solution equilibrium titration (SET) titration (FIG. 5) and the $K_D$ values generated were compared to those of mAb2 for IL-1β and mAb1 for IL-18 binding. FIG. 5 shows titration curves of ECL-based affinity determination in solution, constant concentration of antibody: for IL-18 readout 10 pM, for IL-1βreadout 1 pM; antigen dilutions: highest conc.: huIL-18, 5 nM; marIL-18, 10 nM; huIL-1β, 0.5 nM; marIL-1β, 0.5 nM. Solid lines represent a fit of the data using the model described above. Dotted lines indicate the 95% confidence interval, n=3.

Comparing binding affinities in the individual target binding assay, bbmAb1 showed a similar mean KD compared to mAb1 for human and marmoset IL-18 (Table 7). For human IL-1βbinding the mean KD value was slightly higher for bbmAb1 (2.6 pM) compared to mAb2 (0.6 pM) but still in the same low pM range. Subsequent measurements in the simultaneous dual target binding assay (Table 8) confirmed that bbmAb1 binding KD values for IL-1β were similar to values of mAb2 with the pre-clinical as well as with the clinical grade material. Thus, bbmAb1 possesses binding affinities for both targets in humans and marmosets that are in similar to mAb2 and mAb1, respectively.

TABLE 7

Affinities to recombinant human (hu) and marmoset (mar) IL-1β and IL-18 measured by SET (individual target binding determination)

| | Independent IL-18/IL-1β affinity determination | | | |
|---|---|---|---|---|
| Samples | huIL-18 $K_D$ [pM] | marIL-18 $K_D$ [pM] | huIL-1β $K_D$ [pM] | marIL-1β $K_D$ [pM] |
| mAb1 | 9 ± 2 | 21 ± 3 | n/a | n/a |
| mAb2 | n/a | n/a | 0.6 ± 0.1 | 1.0 ± 0.7 |
| bbmAb1 | 12 ± 4 | 33 ± 7 | 2.6 ± 0.1 | 3.0 ± 2.4 |

In addition to the individual target binding results, simultaneous dual target binding affinities of bbmAb1 were investigated (Table 8) by applying either excess of one target during the assessment of the binding the $K_D$ values of the other target (Assay A) or by applying a mixture of both targets in serial dilutions (Assay B). Simultaneous IL-1β/IL-18 affinity determination showed no significant difference between Assay A (excess of one antigen) and Assay B (mixture of both antigens in serial dilutions) which proved that both targets are bound simultaneously without affecting the binding of the other target. Furthermore, the $K_D$ values obtained with the simultaneous dual binding assays were similar to the $K_D$ values obtained with the standard assay (Table 7; in the absence of the second antigen) which proved that bbmAb1 can bind both antigens independently. Thus, bbmAb1 binds simultaneously and independently both human IL-1β and IL-18 and fully cross-reacts with the corresponding marmoset proteins.

respectively (Table 9 and Table 10). The monovalent format of bbmAb1 as compared to the bivalent format of mAb2/mAb1 but also potentially the KiH mutations may be reasons for this slight difference in potency of bbmAb1.

TABLE 9

Mean IC50 values for IL-1β neutralization by bbmAb1 in comparison to mAb2 in human dermal fibroblasts and human PBMC.

| IL-β inhibition | IL-6 prod.* derm. fibrobl. $IC_{50}$ [nM] | IL-6 prod.* PBMC $IC_{50}$ [nM] |
|---|---|---|
| mAb2 | 0.031 ± 0.006 | 0.29 ± 0.67 |
| bbmAb1 | 0.136 ± 0.045 | 1.35 ± 0.59 |

*Inhibition of IL-6 production in human dermal fibroblasts or PBMC stimulated with recombinant human IL-1β (6 pM for dermal fibroblasts and 60 pM for PBMC).
Shown are mean values ± SEM (n = 3 PBMC and n = 6 human dermal fibroblasts)

TABLE 8

Affinities to recombinant human (hu) and marmoset (mar) IL-1β and IL-18 measured by SET (simultaneous target binding determination

| | Simultaneous IL-18/IL-1β affinity determination | | | | | | | |
|---|---|---|---|---|---|---|---|---|
| | huIL-18 $K_D$ [pM] | | marIL-18 $K_D$ [pM] | | huIL-1β $K_D$ [pM] | | marIL-1β $K_D$ [PM] | |
| Samples | Assay A | Assay B | Assay A | Assay B | Assay A | Assay B | Assay A | Assay B |
| mAb1 | 13.5 | 11.4 | 27.1 | 26.3 | n/a | No binding | n/a | No binding |
| mAb2 | n/a | No binding | n/a | No binding | 1.1 | 3.2 | 0.8 | 4.8 |
| bbmAb1 | 14.8 | 19.5 | 47.9 | 44.2 | 3 | 0.5 | 2 | 0.6 |

(b) Neutralizing Activity of bbmAb1 in Human and Marmoset Cell Assays

The neutralizing activity of bbmAb1 for both cytokines (IL1β and IL-18) was assessed mAb2mAb1). In addition, the potency of bbmAb1 for the neutralization of marmoset IL-1β and IL-18 using marmoset cell assay systems was assessed (see section d).

(c) Individual and Simultaneous IL-1/3 and IL-18 Neutralization in Human Cells

The neutralizing activity of bbmAb1 on IL-1β was assessed by the inhibition of recombinant IL-1β-induced IL-6 production in human dermal fibroblasts (IL-1βused at 6 pM) and in human PBMC (IL-1β used at 60 pM). The neutralizing activity of bbmAb1 on IL-18 was measured by the inhibition of recombinant IL-18-induced IFN-γ production in KG-1 cells and human PBMC (both cells activated with 3 nM recombinant human IL-18 together with 1 ng/ml of recombinant human IL-12). The inhibitory potency of bbmAb1 on IL-1β and IL-18 was always compared to that of either mAb2 or mAb1, respectively. Depending on the assays, the mean IC50 values of bbmAb1 were in sub-nM or single digit nM ranges and up to 2- to 4-fold higher in direct comparison mAb2 (for IL-1β) and mAb1 (for IL-18),

TABLE 10

Mean IC50 values for IL-18 neutralization by bbmAb1 in comparison to mAb1 in KG-1 cells and human PBMC.

| IL-18 inhibition | IFNγ prod.** KG-1 cells $IC_{50}$ [nM] | IFNγ prod.** PBMC $IC_{50}$ [nM] |
|---|---|---|
| mAb1 | 0.035 ± 0.011 | 0.78 ± 0.49 |
| bbmAb1 | 0.071 ± 0.046 | 0.87 ± 0.51 |

**Inhibition of IFNγ production in KG-1 cells or PBMC stimulated with recombinant human IL-18 (3 nM) and human IL-12 (1 ng/ml).
Shown are mean values ± SEM (n = 3 KG-1 and n = 4 PBMC)

bbmAb1 was able to neutralize simultaneously the bioactivity of both IL-1β and IL-18 as demonstrated with the HEK Blue™ reporter cells producing SEAP in response to a 1+1 stimulation with recombinant IL-1β and IL-18 (Table 11). A similar inhibition of SEAP in this assay system was only achievable by the combination of mAb2 and mAb1 but not by the use of the individual antibodies.

TABLE 11

Mean IC50 values for simultaneous neutralization of IL-1β and
IL-18 on SEAP reporter activity in HEK Blue ™ cells.

| Inhibition of SEAP in HEK reporter cells stimulated simultaneously with IL-1β and IL-18 | $IC_{50}$ [nM] |
|---|---|
| mAb2 or mAb1 alone | >30 |
| mAb2 and mAb1 combined | 0.24 ± 0.09 |
| bbmAb1 | 0.71 ± 0.28 |

Shown are means ± SEM of n = 5 experiments.

(d) Neutralizing Activity of bbmAb1 on Marmoset IL-1β and Marmoset IL-18 in Marmoset Cell Assays In order to demonstrate the inhibitory activity of bbmAb1 in marmoset, similar in vitro assays were performed with marmoset cells as with human cells however using recombinant marmoset IL-1β and IL-18 for stimulation. When assessing the inhibition of recombinant marmoset IL-1β-induced IL-6 production in marmoset dermal fibroblasts, bbmAb1 displayed sub-nM potency with 2- to 3-fold higher IC50 values compared to mAb2 (Table 12). Testing bbmAb1 with human dermal fibroblasts stimulated with marmoset IL-1β generated a similar inhibition profile as with human IL-6.

TABLE 12

Inhibition of recombinant marmoset IL-1β induced IL-6 production
in marmoset and human fibroblasts by bbmAb1.

| Marmoset IL-1β | IL-6 prod.* marmoset dermal fibroblasts $IC_{50}$ [nM] | | IL-6 prod.* human derm. fibroblasts $IC_{50}$ [nM] |
|---|---|---|---|
|  | Exp. A | Exp. B | Exp. C |
| bbmAb1 | 0.174 | 0.364 | 0.220 |
| mAb2 | 0.095 | 0.138 | 0.114 |

*Inhibition of IL-6 production in marmoset or human dermal fibroblasts stimulated with recombinant marmoset IL-1β (18 pM).
Results of 3 individual experiments (A, B and C) are shown.

Single to double digit nM IC50 values of bbmAb1 confirmed the neutralizing activity of bbmAb1 for marmoset IL-18 tested in the IFNγ production assay with marmoset blood cells (Table 3-7). Testing bbmAb1 with human PBMC stimulated with marmoset IL-18 generated a similar inhibition profile when measuring the production of human IFNγ.

Thus, bbmAb1 was shown to be fully cross-reactive to marmoset IL-1β and marmoset IL-18 in functional assays using marmoset responder cells.

TABLE 13

Mean IC50 values for inhibition of recombinant marmoset IL-18
induced IFNγ production in marmoset whole blood or human PBMC.

| Marmoset IL-18 | IFNγ prod.** Marmoset blood $IC_{50}$ [nM] | IFNγ prod.** Human PBMC $IC_{50}$ [nM] | Marmoset IL-18 conc. used |
|---|---|---|---|
| bbmAb1 | 10.0 ± 4.1 |  | 1 nM |
| mAb1 | 4.7 ± 2.6 |  | 0.3 nM |
| mAb1 | 181 ± 108 |  | 3 nM |
| mAb1 |  | 6.6 ± 5.0 | 1 nM |

**Inhibition of IFNγ production in marmoset whole blood (n = 3 each compound/condition) or human PBMC (n = 6) stimulated with recombinant marmoset IL-18 (concentration indicated) & human IL-12 (10 ng/ml).
Shown are mean values ± SEM It was demonstrated that bbmAb1, a KiH format IL-1β/IL-18 bi-specific mAb retains the high affinity binding as well as the cytokine neutralizing potency to the two individual targets IL-1β and IL-18 when compared to the original mAbs, mAb2 and mAb1, in a variety of different cell assays. The dual IL-1β and IL-18 neutralizing properties of bbmAb1 were not only demonstrated for the human cytokines/cells but also for the corresponding marmoset cytokines/cells, facilitating appropriate toxicology studies. The up to 2- to 4-fold higher IC50 values that were generated in some of the cellular assays for IL-1β and IL-18 neutralization may be the consequence of the monovalent binding of bbmAb1 as opposed to bi-valent binding of mAb2 and mAb1, respectively. Nevertheless, the dual cytokine neutralization by bbmAb1 may result in additive or synergistic inhibitory activities in vivo that may not be adequately represented in our in vitro cellular systems.

7. Example 3: Effects of Combined IL-1β and IL-18 Stimulation and Blockade in PBMC Inflammasome activation-dependent cleavage of the effector cytokines IL-1β and IL-18 leads to the induction of secondary pro-inflammatory mediators and promotes immune cell recruitment/activation not only systemically but also at the site of inflammation. In two different mouse models for lethal systemic inflammation (a) LPS injection model and (b) FCAS mice (activating missense mutations in NLRP3), the simultaneous absence/inhibition of both IL-1β and IL-18 was more protective from lethality compared to the single IL-1β or single IL-18 absence/inhibition, demonstrating additive or synergistic mechanisms for immune activation (Brydges 2013, van den Berghe 2014). bbmAb1 is a human/marmoset IL-1β/IL-18 reactive bi-specific mAb with no rodent cross-reactivity and thus cannot be tested in mouse models. Therefore, we used LPS/IL-12 to mimic inflammasome-dependent pathway activation in vitro for the stimulation of human PBMC to reveal additive or synergistic inhibitory effects of combined IL-1β/IL-18 neutralization by bbmAb1 and performed a non-biased gene expression analysis using microarrays. As a complementary activity we also compared the gene expression profiles of PBMCs from different donors stimulated with either the combination of recombinant IL-1β and recombinant IL-18 or the single cytokines alone.

(1) Materials and Methods
(a) Cell Culture and ELISA
RPMI 1640 (Invitrogen #31870 or Gibco #61870-010) supplemented with 10% Foetal Bovine Serum (Invitrogen #10108-157), 1% L-Glutamine (Invitrogen #25030-03), 1% penicillin/streptomycin (Invitrogen #15140-148), 10 pM 2-Mercaptoethanol (Gibco #31350-010), 5 mM Hepes (Gibco #15630-080)
Recombinant Human IL-1β was purchased from Sino Biological Inc. (#10139-HNAE-5)
Recombinant human IL-18 was purchased from MBL (#B001-5)
Recombinant human IL-12 was purchased from Biolegend (#573008)
IFNγ ELISA: MAX Standard Set, BioLegend, #430103 or BD OptElA human IFNγ ELISA Set, BD #555142
IL-6 ELISA: MAX Standard Set, BioLegend, #430503
IL-26 ELISA: Cloud Clone Corp #SEB695Hu
mAb2 as described in section IL-1β antibody.
mAb1 as described in section IL-18 antibody.
bbmAb1 as described in Example 1.
LPS from Salmonella enterica serotype enteritidis, Sigma #L7770

PBMC were isolated from buffy coats that were obtained from the Blutspendezentrum Bern Round-bottomed, tissue-culture treated 96-well plates (Costar #3799) Flat-bottomed, tissue-culture treated 96-well plates (Costar #3596) Ficoll-Pacque TMPlus (GE Healthcare Life Sciences #17-1440-02) PBS 1X, without Calcium & Magnesium (Gibco #14190094) Falcon 15 ml polypropylene conical tubes (BD #352096) Falcon 50 ml polypropylene conical tubes (BD #352070)

Leucosep™ tubes with porous barrier, 50 ml, Greiner bio-one #227290

Cell strainer 70 pM, BD Biosciences #352350

Trypanblue, Sigma #T8154

RNA isolation, quantity and quality measurements and qPCR:

Nuclease-free water, Ambion #AM9938
Rnase Zap, Ambion #AM9780
1.5 ml Eppendorf tubes, sterile, Rnase & Dnase free
RLT buffer, Qiagen #1015762
Rneasy Mini Kit, Qiagen #74104
RNase-Free DNase Set, Qiagen #79254
Agilent RNA 6000 Nano Kit, Agilent #5067-1511
Chip priming station, Agilent #5065-4401
IKA vortex mixer
RNaseZAP®, Ambion #9780
Agilent 2100 Bioanalyzer
High Capacity cDNA reverse transcription kit, Applied Biosystems, #PN4374966
Nase-free, Thin-Walled, forsted Lid 0.2 ml PCR tubes, Ambion #AM12225
MicroAmp Optical 384 well reaction plate, Applied Biosystems #4309849
TaqMan GenEx Master Mix, Applied Biosystems #4369514
PCR primer (Applied Biosystems)

| Target | Assay ID Taqman | color/quencher |
|---|---|---|
| IFNγ | Hs00989291_m1 | FAM-MGB |
| IL-26 | Hs00218189_m1 | FAM-MGB |
| RPL27 | Hs03044961_g1 | FAM-MGB |
| HPRT1 | Hs02800695_m1 | FAM-MGB |

Pbmc Preparation:

PBMCs were isolated from buffy coat by means of Ficoll-Paque gradient centrifugations in Leucosep tubes according to the manufacturer's instructions. Briefly, 15 mL of Histopaque was put in 50 mL Leucosep™ tubes and centrifuged for 30 sec at 1300 rpm at RT. With a pipette, 30 mL of a diluted suspension of the buffy coat was added on the top of the Histopaque solution and centrifuged during 15 min at RT at 1000 g without break. Plasma was discarded (approx. 20 ml) and the interface ring collected (=human PBMC) and transferred in a 50 ml falcon tube. The tube was filled with 50 mL of sterile PBS and centrifuged once at 1200 rpm during 5 min at RT. This centrifugation was repeated 2 times. The supernatant was gently discarded and cells re-suspended in 50 mL of PBS with 2% FCS and 2 mM EDTA. The cell suspension was filtered using a 70 μm cell strainer and cells counted using trypan blue staining (500 μL of trypan blue+200 μL of cells +300 μL of PBS).

LPS/IL-12 stimulation of PBMC: Cytokine production in supernatants was prepared according to the following. 250'000 cells/well in 100 ul final volume were distributed in 96-well round bottom plates. LPS was used at concentrations between 0.3 ug/ml and 3000 ug/ml together with recombinant IL-12 at 10 ng/ml. Supernatants were harvested after 24 h at 37° C. and 10% $CO_2$.

RNA extraction from cell pellets was performed according to the following. $3 \times 10^6$ cells/well in 1000 ul final volume were distributed in flat bottom 24-well plates. LPS was used at 3 ug/ml together with recombinant IL-12 at 10 ng/ml. Cells were harvested after 24 h at 37° C. and 10% $CO_2$.

Stimulation of PBMC with recombinant cytokines: $7 \times 10^6$ PBMC per well of a 12-well plate were used in 1.5 ml final of complete RPMI medium. Recombinant cytokines were added at the following final concentrations: 10 ng/ml of recombinant IL-1β, 3 nM of recombinant IL-18, 1 ng/ml of recombinant IL-12. Both, supernatants as well as cells were collected after 4 h and 24 h at 37° C. and 10% $CO_2$.

RNA isolation, quantity and quality assessments: Cells were pelleted and the pellet lysed in 350 μl of Qiagen RTL buffer with 2% β-mercaptoethanol and frozen at −20° C. or −80° C. until all samples of the study have been collected. The RNA isolation was performed using the Qiagen standard protocol. Briefly, 350 μl of 70% Ethanol was added in all samples prior to the transfer to the RNeasy spin column and centrifuged for 15 s at 8000 g. After discarding the flow-through, 350 μl of buffer RW1 was added and the column centrifuged for 15 s at 8000 g to wash the spin column membrane. DNase 1 incubation mix solution was prepared according to the manufacturer's instructions and added to the RNeasy spin column and incubated for 15 min at RT. After washes with 350 μl and 500 μl of buffer RW1, the RNeasy spin column was placed in new 2 ml collection tube and centrifuged at full speed for 1 min. RNA was finally collected by adding 35 μl RNase-free water directly to the spin column membrane and a centrifugation for 1 min at 8000 g to elute the RNA. The amount of RNA was measured using Nanodrop ND-1000 and the RNA was stored at −20° C. RIN measurements were performed for the RNA quality assessment according to manufacturer's instructions. Briefly 1 μl of RNA or ladder were pipetted into an Agilent RNA 6000 Nano chip and measured by using the Agilent 2100 Bioanalyser.

Cytokine Gene Expression Analysis by qPCR:

The method was performed corresponding to the manufacturer's instructions. Briefly, 400 ng of RNA was reverse transcribed according to the instructions using the High-Capacity cDNA Reverse Transcription Kit. The cDNA solutions were diluted 1/10 in RNA/DNA free water and 1 μl cDNA was transferred into a 384-well reaction plate and then mixed with 1 μl of 20×TaqMan® Gene Expression Assay target FAM gene and 10 μl of 2×TaqMan® Gene Expression Master Mix and 10 μl RNA/DNA free water. The plate was loaded onto the Applied Biosystems ViiA™ 7 Real-Time PCR System and the following instrument settings were used:

| Plate document/ experiment parameters | Thermal cycling conditions | | |
|---|---|---|---|
| | Stage | Temp (° C.) | Time (mm:ss) |
| Rxn. Volume: 20 μL | Hold | 50 | 2:00 |
| Ramp rate: Fast | Hold | 95 | 0:20 |
| | Cycle | 95 | 0:01 |
| | (40 cycles) | 60 | 0:20 |

The house keeping genes used for this study were HPRT1 and RLP27. The following formula was used to calculate the relative expression levels of target genes:
1) Ct [Ref]=(Ct [HPRT1]+Ct [RLP27])/2
2) dCt [Ref]=40−Ct [Ref]
3) dCt [Target]=Ct [Target]−Ct [Ref]
4) ddCt=dCt [Ref]−dCt [Target]
5) Relative target gene expression=2^ddCt Microarrays was performed according to the following. Samples were processed by CiToxLAB France on Affymetrix HG_U133_Plus2 microarrays. They were RMA normalized and analyzed in GeneSpring 11.5.1 (Agilent Technologies, Santa Clara, CA). Pathway analysis was done using Ingenuity Pathway Analysis (IPA) and Nextbio (Illumine). The two datasets were treated independently.

Initially, the data were subject to standard quality control (QC) by CiToxLAB, in-house QC by using an R script (MA_AffyQC.R) in Rstudio suite and in GeneSpring (PCA, hybridization controls). Subsequently, it was filtered to eliminate unreliable expression levels: Entities (probesets) were kept where at least 100 percent of samples in any 1 of the experimental conditions have values above the 20th percentile.

Differentially expressed genes (DEG) were identified using the "filter on volcano plot" feature in GeneSpring. Using the filtered genes (expression between 20.0-100.0th percentiles) with an unpaired T-test, probesets with a corrected p-value below 0.05 and a fold change above 2.0 were considered differentially expressed. Where possible, i.e. in the study with LPS (NUID-0000-0202-4150) a Benjamini-Hochberg Multiple Testing Correction was used.

For cytokine stimulation experiments, synergism was calculated using the following formula: Signal A+B/(Signal A+Signal B−Control)≥1.5

The respective signatures (or DEG lists) were used to calculate p-values with a Fisher's exact test which represent the statistical significance of observing an overlap between the signature and the 'disease gene list' (lesional vs non-lesional) of public datasets. To do so, the lists were uploaded into Illumine Base Space Correlation Engine (former Nextbio) and compared using the Meta-Analysis feature and keyword search for diseases.

All Data were exported to EXCEL software and $IC_{50}$ values calculated by plotting dose-response curves for the logistic curve fitting functions using either EXCEL/XLfit4 or GraphPad Prism software. Differences between treatment groups were analyzed by one-way ANOVA followed by Dunnett's multiple comparison using GraphPad Prism software and results were considered statistically significant at p<0.05.

(2) Results
(a) bbmAb1 is Highly Efficacious in Inhibiting LPS/IL-12 Induced IFNγ Production in Whole Blood Exposure of human whole blood to LP S supplemented with 10 ng/ml IL-12 results in an IFNγ response that is largely but not exclusively dependent on the "native" IL-18 produced by the blood cells. The addition of IL-12 enhances the LPS induced IFNγ responses, likely by up-regulating IL-18 receptors on responder cells.

Figure 6A:
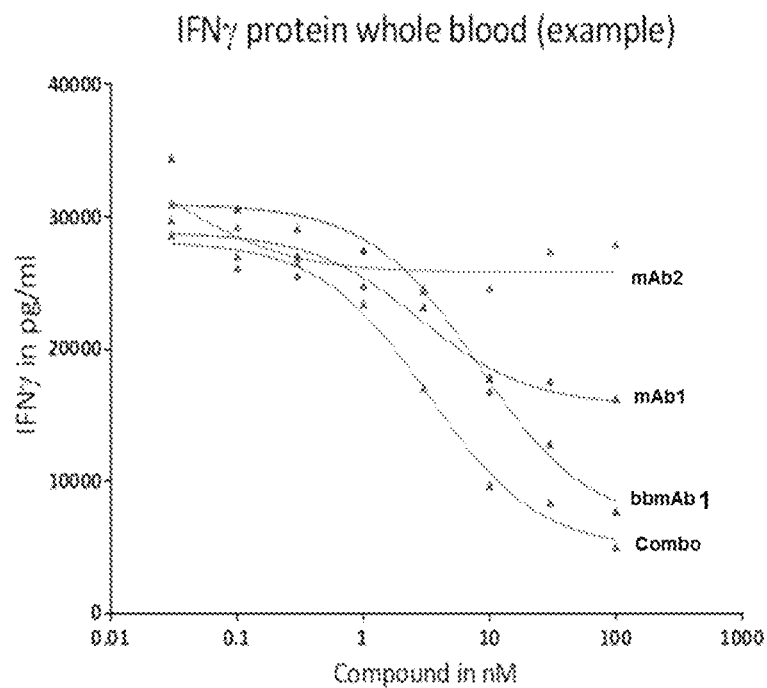
FIG. 6A-6B shows two graphs according to an Example.
Figure 6B:
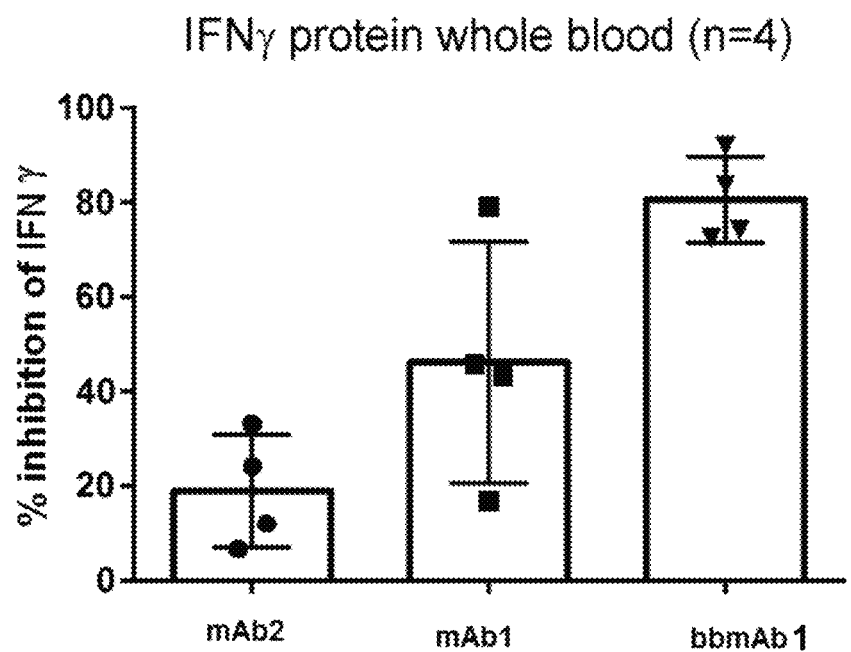

In the experimental conditions used, IL-18 neutralization with mAb1 lead only to an incomplete inhibition of IFNγ production whereas IL-1β blockade (using mAb2) had only small effects on the IFNγ response. Interestingly, the combined inhibition of IL-1β and IL-18 either by bbmAb1 or the combination of mAb2 and mAb1 was more profoundly and completely inhibiting IFNγ production compared to the single cytokine neutralization (FIG. 6). FIG. 6 shows inhibition of LPS (0.3 µg/ml)/IL-12 induced IFNγ in whole blood by bbmAb1, mAb2, mAb1 or combined mAb2 & mAb1 (Combo) (typical inhibition curve shown in FIG. 6A). Percent IFNγ inhibition of n=4 individual donors in whole blood by bbmAb1, mAb1 or mAb2 used at 100 nM (mean and SEM shown in FIG. 6B).

Apart from IFNγ, none of the other cytokines tested (IL-2, -4, -6, -8, -10, -13 and TNFα) were additively inhibited by the combined neutralization of IL-1β and IL-18 in our cell assay (data not shown). The potency of bbmAb1 was in the same range as the combination (combo) of mAb2 and mAb1, considering the monovalent format of the bispecific molecule.

Figure 7A:
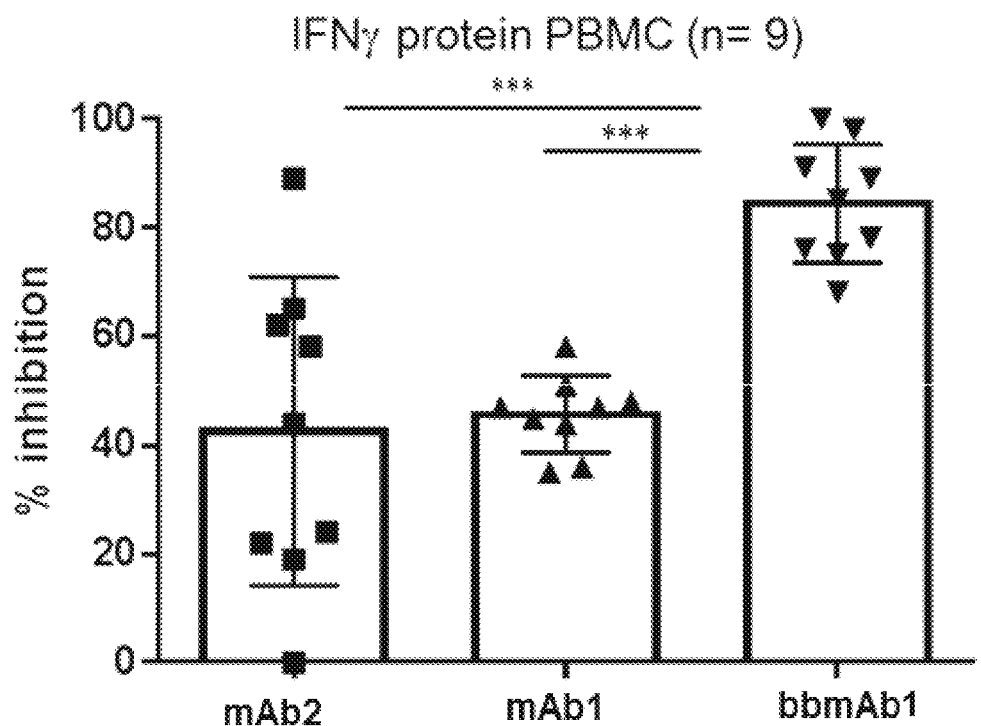
FIG. 7A-7B shows two graphs according to an Example.
Figure 7B:
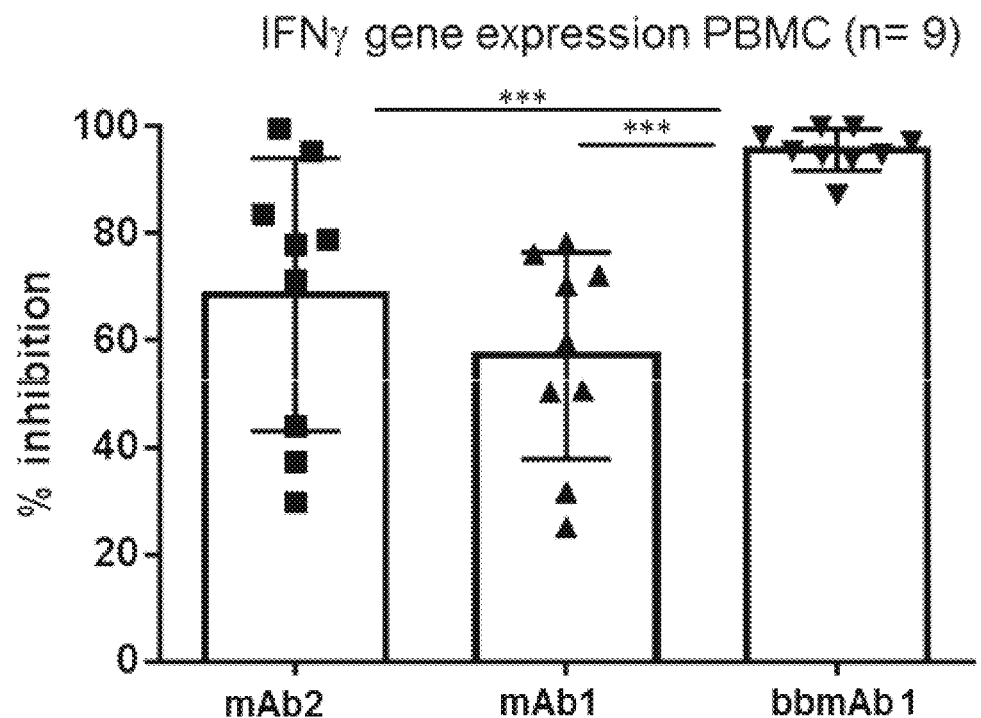

(b) IFNγ is Additively Inhibited by bbmAb1 (i.e. Combined IL-1β/IL-18 Inhibition) Compared to Single IL-1β or IL-18 Inhibition in LPS/IL-12 Activated Human PBMC An unbiased transcriptomics evaluation was required in order to reveal further additive effects (apart of IFNγ) by combined IL-1β/IL-18 inhibition using bbmAb1. Since whole blood is not optimal for transcriptomics analysis we adapted the LPS/IL-12 stimulation assay conditions, described in the materials and method section above, to human PBMC samples. By using PBMCs from a total of 9 donors, we could confirm that bbmAb1 additively inhibited IFNγ protein secretion into the supernatants of the PBMCs (FIG. 7). Compared to whole blood experiments, IFNγ production was inhibited at approximatively 10-fold lower concentrations of the respective mAbs used. Importantly, a similar inhibition pattern was demonstrated at the mRNA level for IFNγ (FIG. 7) which confirmed the suitability of the samples for a non-biased microarray based gene expression analysis. FIG. 7 shows the inhibition of LPS (0.3 µg/ml)/IL-12 induced IFNγ protein production (FIG. 7A) and IFNγ gene expression (FIG. 7B) by bbmAb1, mAb2 and mAb1 (at 10 nM conc. each) in human PBMC. Shown is the percent inhibition in n=9 donors±SEM. ***p<0.05 (one way ANOVA)

Figure 8A:
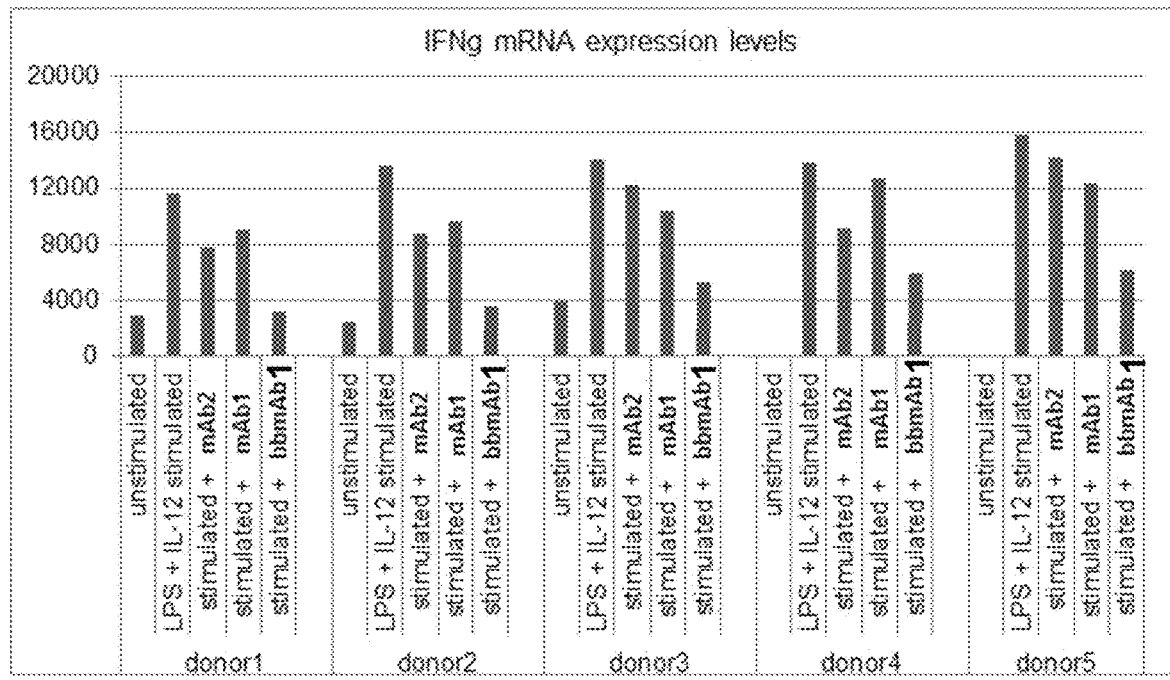
FIG. 8A-8B shows mRNA expression levels according to an Example.
Figure 8B:
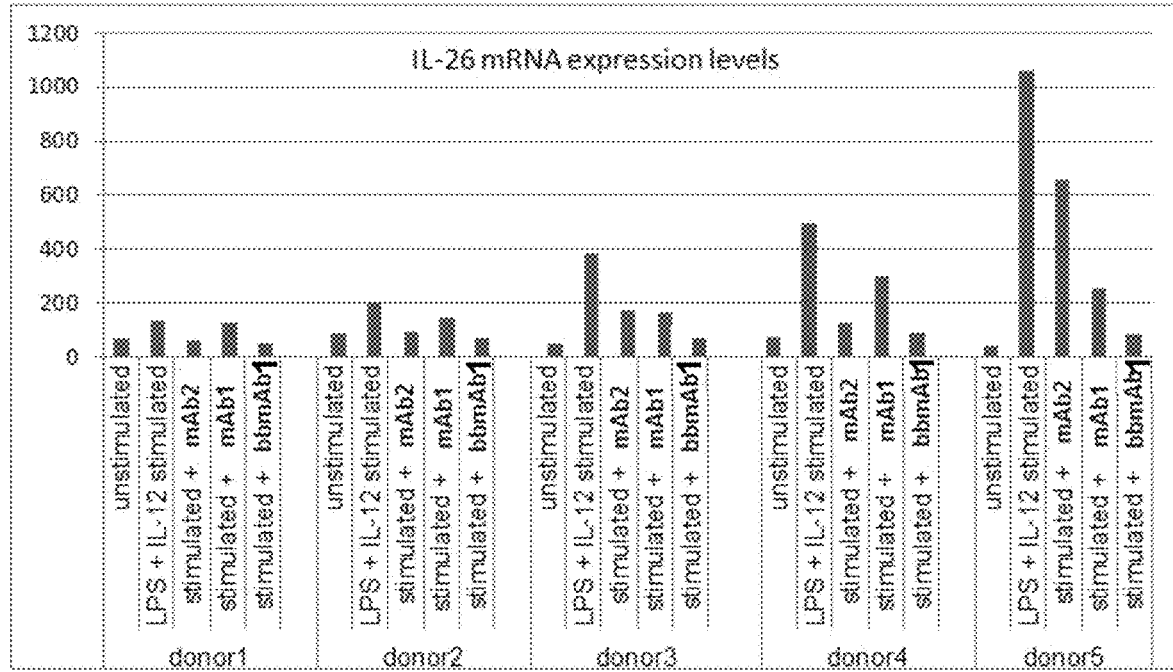
Figure 9A:
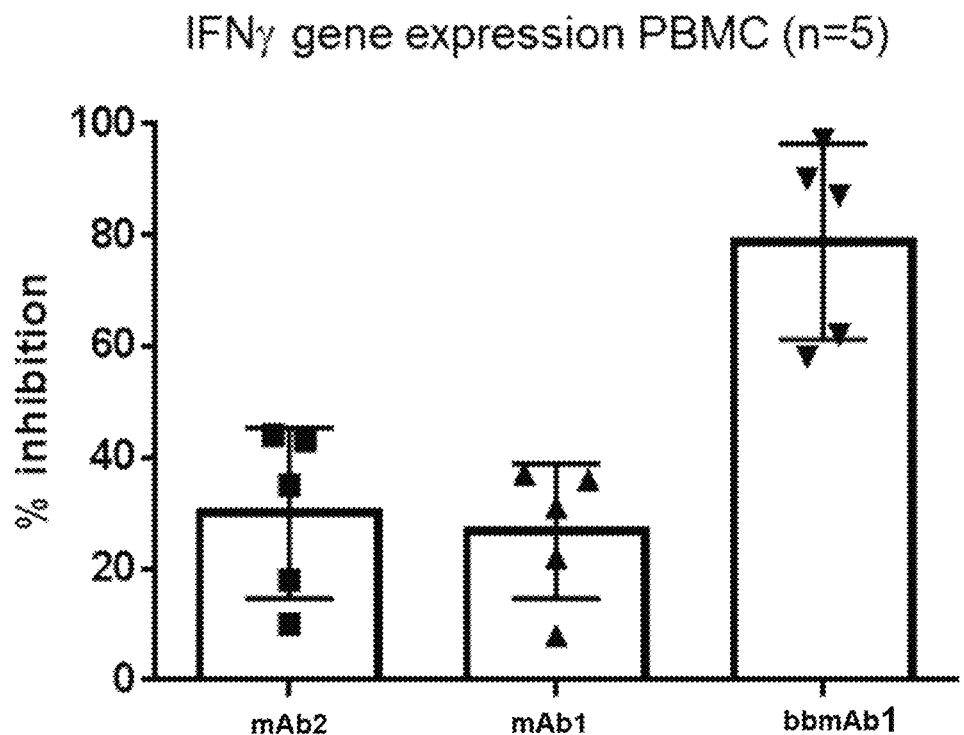
FIG. 9A-9B shows mRNA expression levels according to an Example.
Figure 9B:
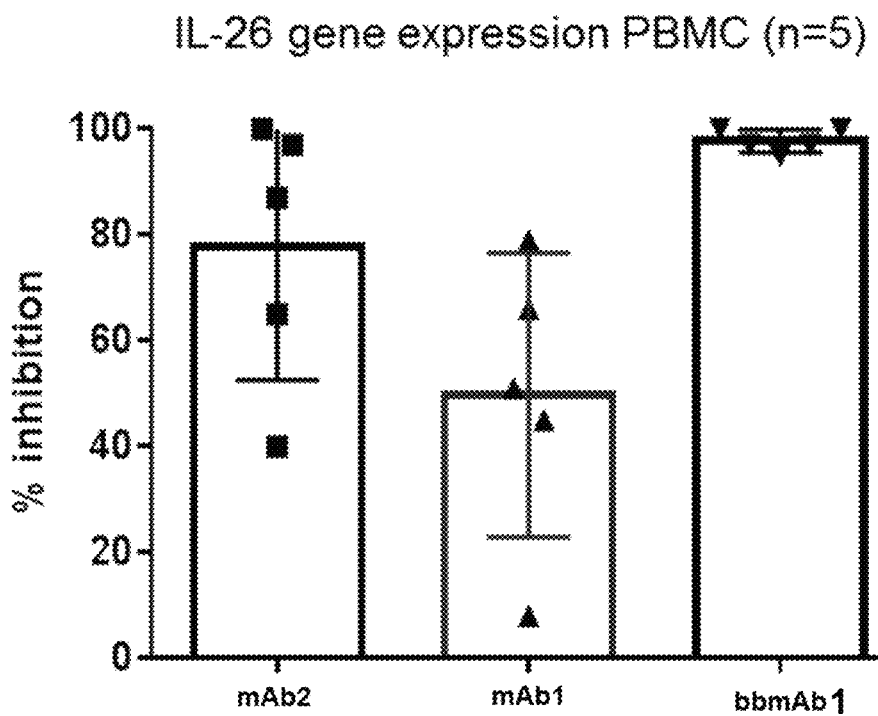

The Affymetrix microarray was conducted with n=5 individual donors from PBMCs that were sampled from the LPS/IL-12 stimulation experiments described in the materials and method section above. Unfortunately, the overall assessment of the gene expression profiles evidenced a strong LPS/IL-12 stimulation effect and the PCA showed clustering per donor rather than compound within the stimulated or unstimulated groups. Nevertheless, comparing the LPS/IL-12 stimulated samples with the stimulated plus bbmAb1 for differentially expressed genes revealed a shortlist of genes that are downregulated by the combined IL-1β/IL-18 blockade with bbmAb1 (Table 14). Apart from the strong downregulation of the IFNγ gene that re-validated our microarray data, also the IL-26 gene was a further cytokine gene additively inhibited by bbmAb1 compared to the single IL-1βinhibition (by mAb2) or IL-18 inhibition (by mAb1) (see FIG. 8). FIG. 8 and FIG. 9 show microarray data derived gene expression levels for IFNγ and IL-26 and the inhibition by bbmAb1, mAb2 and mAb1 (10 nM each) in LPS (0.3 ug/ml)/IL-12 stimulated PBMC at 24 h. Values of individual donors are shown in FIG. 8A (IFNγ) and FIG. 8B (IL-26) and percent inhibition (mean±SEM) from the n=5 donors are shown in FIG. 9A (IFNγ) and FIG. 9B (IL-26).

TABLE 14

Differentially expressed genes (downregulated genes only between the bbmAb1 and control group in LPS/IL-12 stimulated samples).

| Probe Set ID | Gene Symbol | Entrez Gene | p-value | FC |
|---|---|---|---|---|
| 222974_at | IL22 | 50616 | 0.03188 | 6.6 |
| 221111_at | IL26 | 55801 | 0.00224 | 5.2 |
| 223939_at | SUCNR1 | 56670 | 0.00234 | 4.0 |
| 1560791_at | OTTHUMG0000010886 | | 0.03660 | 3.7 |
| 211122_s_at | CXCL11 | 6373 | 0.02954 | 3.5 |
| 203915_at | CXCL9 | 4283 | 0.02211 | 3.4 |
| 235229_at | | | 0.02400 | 3.3 |
| 210163_at | CXCL11 | 6373 | 0.02707 | 3.2 |
| 210354_at | IFNG | 3458 | 0.00007 | 2.9 |
| 243541_at | IL31RA | 133396 | 0.01200 | 2.5 |
| 236003_x_at | OR2I1P | | 0.04942 | 2.4 |
| 203131_at | PDGFRA | 5156 | 0.00161 | 2.4 |
| 219991_at | SLC2A9 | 56606 | 0.00191 | 2.4 |
| 201860_s_at | PLAT | 5327 | 0.00139 | 2.3 |
| 205692_s_at | CD38 | 952 | 0.04855 | 2.3 |
| 1555600_s_at | APOL4 | 80832 | 0.02610 | 2.3 |
| 215305_at | PDGFRA | 5156 | 0.01180 | 2.2 |
| 236191_at | | | 0.04037 | 2.1 |
| 204533_at | CXCL10 | 3627 | 0.04847 | 2.1 |
| 229915_at | FAM26F | 441168 | 0.02912 | 2.0 |
| 210072_at | CCL19 | 6363 | 0.02827 | 2.0 |
| 236101_at | | | 0.03246 | 2.0 |

FC = fold change.

Figure 10A:
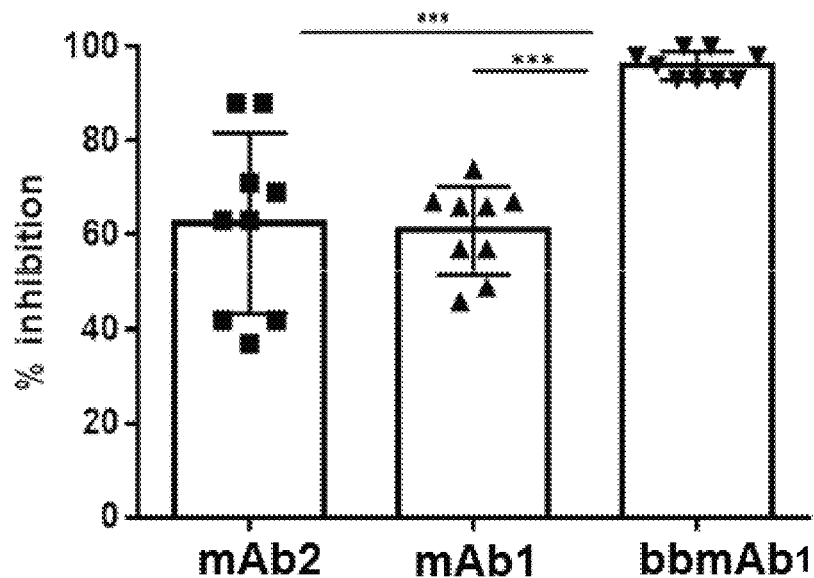
FIG. 10A-10B shows two graphs according to an Example.
Figure 10B:
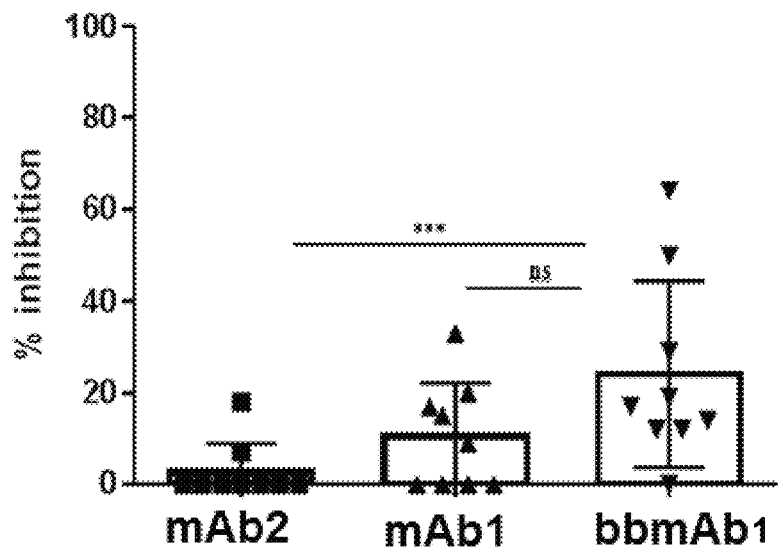

(c) IL-26 is Another Pro-Inflammatory Cytokine Additively Inhibited by by bbmAb1 in LPS/IL-12 Stimulated PBMC To further confirm that LPS/IL-12 driven IL-26 gene expression and protein production is most efficiently inhibited by combined IL-1β/IL-18 blockade using bbmAb1, the study was extended to a total of n=9 PBMC donors and investigated IL-26 gene expression by qPCR and IL-26 protein production by ELISA. As shown in FIG. 10, it largely confirmed the inhibition of IL-26 gene expression obtained with the microarray approach (FIG. 10A). Interestingly, IL-26 protein levels in supernatants were only partly reduced at 24 h by the addition of the mAbs (FIG. 10B). The reasons for this differences are unknown, could however be related to kinetic differences between IL-26 gene expression and protein production as well as differences in the consumption of IL-26 compared to IFNγ. Nevertheless, bbmAb1 was superior in reducing IL-26 protein levels in the PBMC supernatants compared to mAb2 and mAb1. FIG. 10 shows the inhibition of LPS (0.3 ug/ml)/IL-12 induced IL-26 gene expression (by qPCR) (FIG. 10A) and IL-26 protein levels (FIG. 10B) by bbmAb1, mAb2 and mAb1 (10 nM each) in human PBMC. Percent inhibition of n=9 individual PBMC donors (mean and SEM). ***p<0.05 (one way ANOVA).

(d) IL1β/IL18 Signaling Signatures Correlate with Disease

Figure 11:
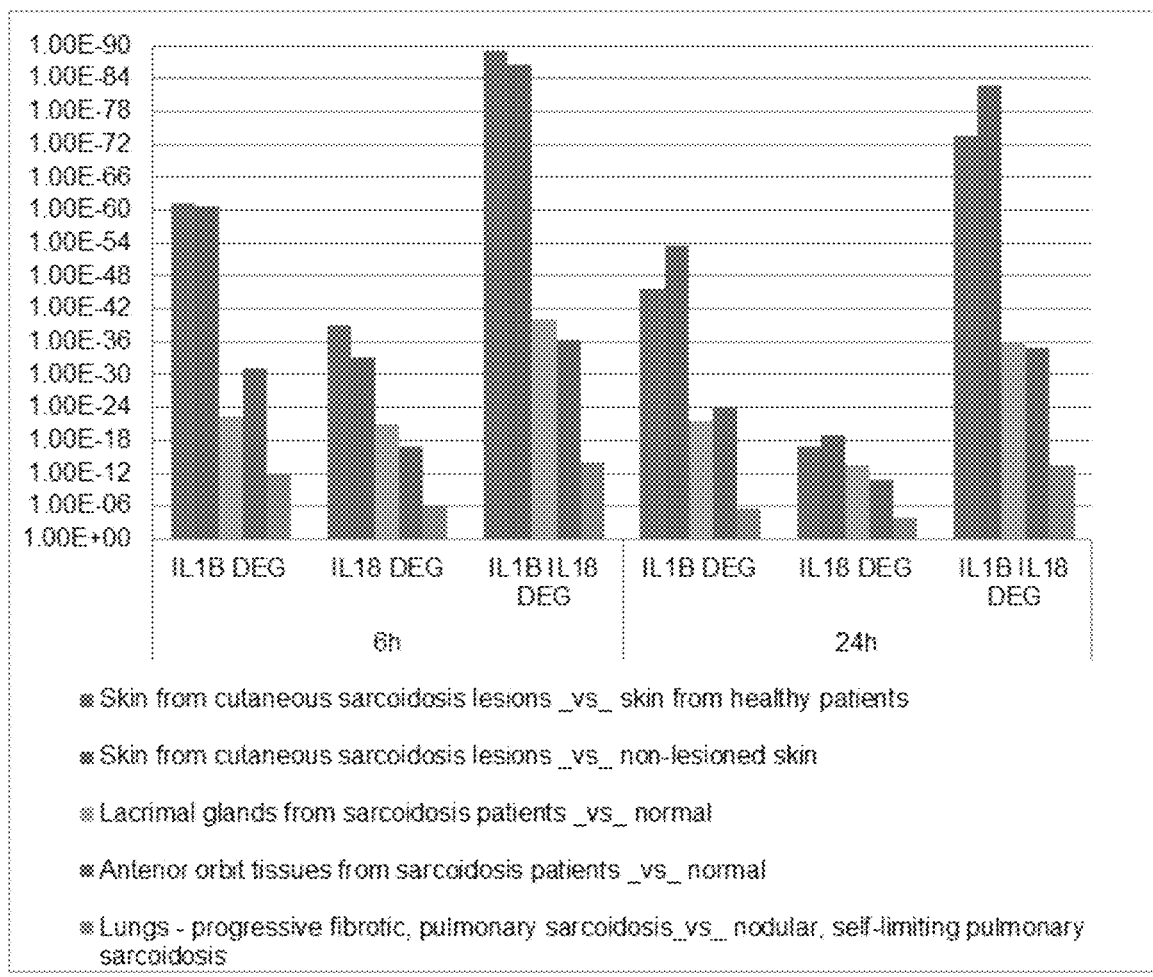
FIG. 11 is a graph showing statistical correlations according to an Example.

Previously established PBMC culture conditions where recombinant IL-1β stimulation resulted in either IL-6 production or recombinant IL-18/IL-12 stimulation resulted in IFNγ production was combined to reveal additive or synergistic downstream target genes or signatures (data not shown). With PBMCs from n=4 donors sampled at two different time points (6 h and 24 h) an Affymetrix microarray evaluation for unbiased assessment of the gene expression profiles was conducted. Genes that were synergistically upregulated at 6 h and at 24 h with the combined stimulation by IL-1β and IL-18 were revealed (data not shown). The addition of IL-12 to the IL-1β/IL-18 combination largely increased the synergy for a series of upregulated genes. The generated signalling signatures of single or combined IL-1β/IL-18 pathway stimulation (UP-regulated genes only) were used to interrogate dataset from patients across several autoimmune diseases. For example, correlation to public sarcoidosis datasets is shown as an example in FIG. 11. P-values (calculated with a Fisher's exact test) show a significant correlation to several public studies comparing healthy to diseased tissues from sarcoidosis patients. Tissues include skin as well as lung, lacrimal glands and anterior orbit. Across all datasets, the combination of IL1β/IL18 signaling shows the best correlation to disease, followed by IL-1β and IL-18. IL-1β/IL-18 differentially up-regulated genes (DEG) in PBMC (x-axis) compared to 5 different sarcoidosis tissue 'diseased vs healthy' DEG. P-values (y-axis) represent the statistical significance of observing an overlap between the signature and the 'disease gene list'. Black bar is skin from cutaneous sarcoidosis lesion vs skin from healthy patients. Light grey bar is skin from cutaneous sarcoidosis lesion vs non-lesioned skin. White bar is lacrimal glands from sarcoidosis patients vs normal. Dark grey bar is anterior orbit tissues from sarcoidosis patients vs normal. Striped bar is lung samples with progressive fibrotic, pulmonary sarcoidosis vs nodular self-limiting pulmonary sarcoidosis.

(e) Conclusion

LPS and recombinant IL-12 was used to mimic pathogen associated molecular pattern (PAMP)-dependent NLRP3 inflammasome activation within the first 24 h of in vitro culture. It was demonstrated that combined inhibition of IL-1β and IL-18, by using bbmAb1, acts additively to decrease/inhibit IFNγ production in PBMC stimulated with LPS/IL-12. IL-12 was previously described to act synergistically with IL-18 to induce IFNγ production in T, B, NK cells, macrophages and dendritic cells (as reviewed by Nakanishi, 2001) but now an additional stimulatory effect of IL-1β on IFNγ production could be demonstrated under the experimental conditions used. Thus, the co-incubation of PBMC with LPS/IL-12 drives efficiently the production of "native" IL-1β and IL-18 which contribute both to a strong IFNγ response. By using unbiased microarray transcriptomics, additional genes were identified that were additively down-regulated by combined IL-1β/IL-18 neutralization vs. single IL-1β or IL-18 blockade. Amongst those was IL-26, a member of the IL-20 cytokine subfamily (IL-19, IL-20, IL-22, IL-24, and IL-26), which is conserved in most vertebrate species but absent in most rodent strains (including mice and rats) (Donnelly 2010). It signals through a heterodimeric receptor complex composed of the IL-20R1 and IL-10R2 chains. IL-26 receptors are primarily expressed on non-hematopoietic cell types, particularly epithelial cells. Increased levels of IL-26 were reported in serum and particularly in the synovial fluid of RA patients (Corvaisier 2012) where it could act as factor to promote Th17 cell growth and differentiation. Unfortunately, the discovery of further genes/pathways induced by the combined blockade of IL-1β and IL-18 was hampered by the strong effect of the LPS/IL-12 stimulation of the PBMC samples. Nevertheless, both IFNγ and IL-26 and to some extend also IL-22 were also among the genes that were synergistically upregulated by the combined stimulation with recombinant IL-1β and IL-18 in PBMC, confirming that these two factors are downstream effectors in this activation pathway. Thus, the IL-20 subfamily of cytokines (including IL-26 and IL-22) seems to be strongly dependent on the simultaneous signals from IL-1β and IL-18. With all due caution about selectivity of the individual signalling signatures as well as potential efficacy of blocking, these comparisons are useful to show that the respective pathways are active in diseases like sarcoidosis.

8. Example 4: Therapeutic Use

Combined targeting of IL-1β and IL-18 may represent a more effective treatment strategy than single cytokine blockade in inflammasome-driven inflammatory conditions where both innate and adaptive immunity components are involved. Simultaneous neutralization of IL-1β and IL-18 targets both innate and adaptive immunity components, including neutrophils, Th1/Tc1 and NK cells, adhesion molecules on immune and endothelial cells and pro-inflammatory cytokines (e.g. IL-6, IFNγ and IL-17). The advantage of blocking both IL-1β and IL-18 is supported by data obtained in a pre-clinical mouse model of Familial Cold Autoimmune Syndrome (FCAS) which is driven by constitutive NIrp3 inflammasome activation and overproduction of IL-1β and IL-18 (Brydges 2013). There, a partial rescue from the FCAS condition was achieved in mice when either IL-1β or IL-18 signalling was genetically ablated demonstrating involvement of both cytokines in disease pathogenesis. Importantly, FCAS mice lacking both IL-18 and IL-1βsignalling developed even less disease compared to mice in which only one of the two cytokines was inactivated demonstrating additive effects of dual IL-1β/IL-18 neutralization. Additive effects of IL-1β and IL-18 neutralization were also demonstrated in another mouse model, where high doses of LPS were injected in mice to cause septic shock (van den Berghe 2014). In this model either genetic deficiency for both IL-1β and IL-18 or the combined neutralization of both cytokines by neutralizing antibodies completely prevented LPS lethality whereas single cytokine deficiency/neutralization was only partly protective.

The overall clinical strategy for a bispecific, which targets both IL-1β and IL-18 simultaneously, may represent a more effective means of treatment than currently available options. To identify candidate diseases, preclinical and translational research was utilized to demonstrate active involvement of both IL-1β and IL-18 downstream pathways in the underlying pathophysiology of candidate diseases. There is novel evidence that chronic pulmonary sarcoidosis is an inflammasome-driven disease with both innate and adaptive immunity involvement. Furthermore, initial findings indicate important roles for both IL-1β and IL-18 effector cytokines in this disease. Thus, sarcoidosis represents an ideal opportunity to demonstrate the dual specificities of bbmAb1 in a disease with established, chronic tissue inflammation. Efficacy of bbmAb1 in sarcoidosis may lead to development in other interstitial lung diseases such as hypersensitivity (occupational) lung diseases due to silica or beryllium. Other candidate diseases are granulomatous inflammation involving other organ tissues, such as Crohn's disease.

Vascular inflammation with tissue injury and endothelial dysfunction also represents a potential target for bbmAb1. Dysfunctional endothelial cells can respond to effective anti-inflammatory treatment, resulting in improved vascular flow even in the presence of fixed intravascular defects. Recent literature evidence has identified sickle cell disease (SCD) to have a strong inflammasome-driven component via high rates of constitutive intravascular hemolysis. Inflammasome activation due to release of danger signals (uric acid, heme/Fe3+, other intracellular components) from chronic RBC lysis triggers inflammasome receptors, activation of same and leads to intravascular inflammatory cascade, giving upregulation of endothelial cell adhesion molecules, activation of neutrophils and platelets, resulting in chronic activation of endothelial cells. This unremitting vascular inflammation in SCD patients leads to recurrent, painful vaso-occlusive crises and acute on chronic tissue damage. Preliminary internal evidence provides support for involvement of IL-18 as well as IL-1β in the underlying disease process of SCD. Thus, reducing the basal inflammation in SCD patients by bbmAb1 treatment could attenuate chronic background inflammation and prevent acute crises with associated end-organ damage, prevent acute sickle cell crises and associated end organ damage, along with improving patients' general quality of life by reducing associated chronic pain and fatigue. Demonstration of bbmAb1 therapeutic efficacy in SCD patients may lead to development in other chronic or acute on chronic inflammatory conditions involving high rates of hemolysis, such as malaria and hemodialysis-dependent, chronic kidney disease. Further indications that might benefit from both IL-1β and IL-18 modulation are indications associated with ischemia-reperfusion tissue injury, such as cardiovascular diseases or improved healing of wounds of all types, but in particular the most severe soft tissue injury of burn.

Thus, in an embodiment of the invention, a method of treating an inflammasome related disorder comprising administering to a subject, afflicted with an inflammasome related disorder, an effective amount of a bbmAb disclosed herein, such as bbmAb1. Potential inflammasome related disorders are cryopyrin-associated autoinflammatory syndrome (CAPS), familial Mediterranean fever (FMF), systemic juvenile idiopathic arthritis (SJIA), lupus nephritis, diabetic nephropathy, acute kidney injury, renal hypertension, IgA nephropathy, glomerulonephritis (GN), frontotemporal dementia (FTD), Alzheimer's disease (AD), epilepsy, stroke, Parkinson's disease (PD), depression, sarcoidosis, such as pulmonary sarcoidosis, pancreatitis, idiopathic pulmonary fibrosis (IPF), non-alcoholic steatohepatitis (NASH), atherosclerosis, giant-cell arteritis, anti-neutrophil cytoplasmic antibody (ANCA)-associated vasculitis, age-related macular degeneration (AMD), graft-versus-host disease, type 2 diabetes, acne, sickle cell disease, vasculopathy, ischemia-reperfusion injury, cardiovascular disease, peripheral artery disease (PAD), atherosclerosis, vascular dysfunction, skeletal muscle ischemia, fibrosis, malaria, hemodialysis-dependent, chronic kidney disease or Crohn's disease.

In one embodiment, a method of treating sickle cell disease, vasculopathy, ischemia-reperfusion injury, cardiovascular disease, peripheral artery disease, atherosclerosis, vascular dysfunction, skeletal muscle ischemia, pulmonary sarcoidosis, fibrosis, malaria, hemodialysis-dependent, chronic kidney disease or Crohn's disease in a subject is provided, by administering an effective amount of a bbmAb disclosed herein, such as bbmAb1, to the subject.

9. Example 5: Pharmaceutical Compositions

Provided herein are pharmaceutical compositions comprising the bbmAb antibodies, such as bbmAb1, formulated together with a pharmaceutically acceptable carrier. The compositions can additionally contain one or more other therapeutic agents that are suitable for treating a medical condition. Pharmaceutically acceptable carriers enhance or stabilize the composition, or can be used to facilitate preparation of the composition. Pharmaceutically acceptable carriers include solvents, dispersion media, coatings, antibacterial and antifungal agents, isotonic and absorption delaying agents, and the like that are physiologically compatible.

A pharmaceutical composition described herein can be administered by a variety of methods known in the art. The route and/or mode of administration vary depending upon the desired results. It is preferred that administration be intravitreal, intravenous, intramuscular, intraperitoneal, or subcutaneous, or administered proximal to the site of the target. The pharmaceutically acceptable carrier should be suitable for intravitreal, intravenous, intramuscular, subcutaneous, parenteral, spinal or epidermal administration (e.g., by injection or infusion). Depending on the route of administration, the active compound, i.e. bbmAb, may be coated in a material to protect the compound from the action of acids and other natural conditions that may inactivate the compound.

The composition should be sterile and fluid. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

Pharmaceutical compositions described herein can be prepared in accordance with methods well known and routinely practiced in the art. See, e.g., Remington: The Science and Practice of Pharmacy, Mack Publishing Co., 20th ed., 2000; and Sustained and Controlled Release Drug Delivery Systems, J. R. Robinson, ed., Marcel Dekker, Inc., New York, 1978. Pharmaceutical compositions are preferably manufactured under GMP conditions. Typically, a therapeutically effective dose or efficacious dose of the bbmAb is employed in the pharmaceutical compositions described herein. The bbmAbs are formulated into pharmaceutically acceptable dosage forms by conventional methods known to those of skill in the art. Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Actual dosage levels of the active ingredients in the pharmaceutical compositions described herein can be varied so as to obtain an amount of the active ingredient which is effective to achieve the desired therapeutic response for a particular patient, composition, and mode of administration, without being toxic to the patient. The selected dosage level depends upon a variety of pharmacokinetic factors including the activity of the particular compositions described herein employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors.

A physician or veterinarian can start doses of the antibodies described herein employed in the pharmaceutical composition at levels lower than that required to achieve the desired therapeutic effect and gradually increase the dosage until the desired effect is achieved. In general, effective doses of the compositions described herein, for the treatment of a wasting disorders described herein vary depending upon many different factors, including means of administration, target site, physiological state of the patient, whether the patient is human or an animal, other medications administered, and whether treatment is prophylactic or therapeutic. Treatment dosages need to be titrated to optimize safety and efficacy. For systemic administration with an antibody, the dosage ranges from about 0.0001 to 100 mg/kg, and more usually 0.01 to 15 mg/kg, of the host body weight. For intravitreal administration with an antibody, the dosage may range from 0.1 mg/eye to 5 mg/eye. An exemplary treatment regime entails systemic administration once per every two weeks or once a month or once every 3 to 6 months. An exemplary treatment regime entails systemic administration once per every two weeks or once a month or once every 3 to 6 months, or as needed (PRN).

Biological therapeutics, such as bbmAb1, are usually administered on multiple occasions. Intervals between single dosages can be weekly, monthly or yearly. Intervals can also be irregular as indicated by measuring blood levels of bbmAb1 in the patient. In addition alternative dosing intervals can be determined by a physician and administered monthly or as necessary to be efficacious. In some methods of systemic administration, dosage is adjusted to achieve a plasma antibody concentration of 1-1000 µg/ml and in some methods 25-500 µg/ml. Alternatively, antibody can be administered as a sustained release formulation, in which case less frequent administration is required. Dosage and frequency vary depending on the half-life of the antibody in the patient. In general, human antibodies show longer half-life than that of chimeric antibodies and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Sequence Table

Useful amino acid and nucleotide sequences for practicing the invention are disclosed in Table 15.

TABLE 15

Sequences according to embodiments of the invention

| SEQ ID NUMBER | Ab region | Sequence |
|---|---|---|
| mAb1 | | |
| SEQ ID NO: 1 (Kabat) | HCDR1 | SYAIS |
| SEQ ID NO: 2 (Kabat) | HCDR2 | NIIPMTGQTYYAQKFQG |
| SEQ ID NO: 3 (Kabat) | HCDR3 | AAYHPLVFDN |
| SEQ ID NO: 4 (Chothia) | HCDR1 | GGTFKSY |
| SEQ ID NO: 5 (Chothia) | HCDR2 | IPMTGQ |
| SEQ ID NO: 6 (Chothia) | HCDR3 | AAYHPLVFDN |
| SEQ ID NO: 7 | VH | EVQLVQSGAEVKKPGSSVKVSCKASG GTFKSYAISWVRQAPGQGLEWMGNIIP MTGQTYYAQKFQGRVTITADESTSTAY MELSSLRSEDTAVYYCARAAYHPLVFD NWGQGTLVTVSS |
| SEQ ID NO: 8 | DNA VH | GAGGTGCAGCTGGTGCAGAGCGGCG CCGAGGTGAAGAAGCCCGGCAGCAG CGTGAAGGTGAGCTGCAAGGCCAGC GGCGGCACCTTCAAGAGCTACGCCA TCAGCTGGGTGAGGCAGGCCCCCGG CCAGGGCCTGGAGTGGATGGGCAAC ATCATCCCCATGACCGGCCAGACCTA CTACGCCCAGAAGTTCCAGGGCAGG GTGACCATCACCGCCGACGAGAGCA CCAGCACCGCCTACATGGAGCTGAG CAGCCTGAGGAGCGAGGACACCGCC GTGTACTACTGCGCCAGGGCCGCCT ACCACCCCCTGGTGTTCGACAACTG GGCCAGGGCACCCTGGTGACCGTGA GCAGC |
| SEQ ID NO: 9 | Heavy Chain | EVQLVQSGAEVKKPGSSVKVSCKASG GTFKSYAISWVRQAPGQGLEWMGNIIP MTGQTYYAQKFQGRVTITADESTSTAY MELSSLRSEDTAVYYCARAAYHPLVFD NWGQGTLVTVSSASTKGPSVFPLAPS SKSTSGGTAALGCLVKDYFPEPVTVS WNSGALTSGVHTFPAVLQSSGLYSLSS VVTVPSSSLGTQTYICNVNHKPSNTKV DKRVEPKSCDKTHTCPPCPAPEAAGG PSVFLFPPKPKDTLMISRTPEVTCVVVD VSHEDPEVKFNWYVDGVEVHNAKTKP REEQYNSTYRVVSVLTVLHQDWLNGK EYKCKVSNKALPAPIEKTISKAKGQPRE PQVYTLPPSREEMTKNQVSLTCLVKGF YPSDIAVEWESNGQPENNYKTTPPVLD SDGSFFLYSKLTVDKSRWQQGNVFSC SVMHEALHNHYTQKSLSLSPGK |
| SEQ ID NO: 10 | DNA Heavy Chain | GAGGTGCAGCTGGTGCAGAGCGGCG CCGAGGTGAAGAAGCCCGGCAGCAG CGTGAAGGTG AGCTGCAAGGCCAGCGGCGGCACCT TCAAGAGCTACGCCATCAGCTGGGT GAGGCAGGCC CCCGGCCAGGGCCTGGAGTGGATGG GCAACATCATCCCCATGACCGGCCA GACCTACTAC GCCCAGAAGTTCCAGGGCAGGGTGA CCATCACCGCCGACGAGAGCACCAG CACCGCCTAC ATGGAGCTGAGCAGCCTGAGGAGCG AGGACACCGCCGTGTACTACTGCGC CAGGGCCGCC TACCACCCCCTGGTGTTCGACAACTG GGCCAGGGCACCCTGGTGACCGTGA GCAGCGCC AGCACCAAGGGCCCCAGCGTGTTCC CCCTGGCCCCCAGCAGCAAGAGCAC CAGCGGCGGC ACCGCCGCCCTGGGCTGCCTGGTGA |

TABLE 15-continued

Sequences according to embodiments of the invention

| SEQ ID NUMBER | Ab region | Sequence |
|---|---|---|
| | | AGGACTACTTCCCCGAGCCCGTGAC CGTGAGCTGG AACAGCGGCGCCCTGACCAGCGGCG TGCACACCTTCCCCGCCGTGCTGCA GAGCAGCGGC CTGTACAGCCTGAGCAGCGTGGTGA CCGTGCCCAGCAGCAGCCTGGGCAC CCAGACCTAC ATCTGCAACGTGAACCACAAGCCCAG CAACACCAAGGTGGACAAGAGGGTG GAGCCCAAG AGCTGCGACAAGACCCACACCTGCC CCCCCTGCCCCGCCCCCGAGGCCGC CGGCGGCCCC AGCGTGTTCCTGTTCCCCCCCAAGCC CAAGGACACCCTGATGATCAGCAGG ACCCCCGAG GTGACCTGCGTGGTGGTGGACGTGA GCCACGAGGACCCCGAGGTGAAGTT CAACTGGTAC GTGGACGGCGTGGAGGTGCACAACG CCAAGACCAAGCCCAGGGAGGAGCA GTACAACAGC ACCTACAGGGTGGTGAGCGTGCTGA CCGTGCTGCACCAGGACTGGCTGAA CGGCAAGGAG TACAAGTGCAAGGTGAGCAACAAGG CCCTGCCCGCCCCCATCGAGAAGAC CATCAGCAAG GCCAAGGGCCAGCCCAGGGAGCCC CAGGTGTACACCCTGCCCCCCAGCA GGGAGGAGATG ACCAAGAACCAGGTGAGCCTGACCT GCCTGGTGAAGGGCTTCTACCCCAG CGACATCGCC GTGGAGTGGGAGAGCAACGGCCAGC CCGAGAACAACTACAAGACCACCCC CCCCGTGCTG GACAGCGACGGCAGCTTCTTCCTGTA CAGCAAGCTGACCGTGGACAAGAGC AGGTGGCAG CAGGGCAACGTGTTCAGCTGCAGCG TGATGCACGAGGCCCTGCACAACCA CTACACCCAG AAGAGCCTGAGCCTGAGCCCCGGCA AG |
| SEQ ID NO: 11 (Kabat) | LCDR1 | SGSSSNIGNHYVN |
| SEQ ID NO: 12 (Kabat) | LCDR2 | RNNHRPS |
| SEQ ID NO: 13 (Kabat) | LCDR3 | QSWDYSGFSTV |
| SEQ ID NO: 14 (Chothia) | LCDR1 | SSSNIGNHY |
| SEQ ID NO: 15 (Chothia) | LCDR2 | RNN |
| SEQ ID NO: 16 (Chothia) | LCDR3 | WDYSGFST |
| SEQ ID NO: 17 | VL | DIVLTQPPSVSGAPGQRVTISCSGSSS NIGNHYVNWYQQLPGTAPKLLIYRNNH RPSGVPDRFSGSKSGTSASLAITGLQS EDEADYYCQSWDYSGFSTVFGGGTKL TVL |
| SEQ ID NO: 18 | DNA VL | GATATCGTCCTGACTCAGCCCCCTAG CGTCAGCGGCGCTCCCGGTCAGAGA GTGACTATTAGCTGTAGCGGCTCTAG CTCTAATATCGGTAATCACTACGTGA ACTGGTATCAGCAGCTGCCCGGCAC CGCCCCTAAGCTGCTGATCTATAGAA ACAATCACCGGCCTAGCGGCGTGCC CGATAGGTTTAGCGGATCTAAGTCAG GCACTAGCGCTAGTCTGGCTATCACC GGACTGCAGTCAGAGGACGAGGCCG ACTACTACTGTCAGTCCTGGGACTAT |

TABLE 15-continued

Sequences according to embodiments of the invention

| SEQ ID NUMBER | Ab region | Sequence |
|---|---|---|
| | | AGCGGCTTTAGCACCGTGTTCGGCG<br>GAGGCACTAAGCTGACCGTGCTG |
| SEQ ID NO: 19 | Light Chain | DIVLTQPPSVSGAPGQRVTISCSGSSS<br>NIGNHYVNWYQQLPGTAPKLLIYRNNH<br>RPSGVPDRFSGSKSGTSASLAITGLQS<br>EDEADYYCQSWDYSGFSTVFGGGTKL<br>TVLGQPKAAPSVTLFPPSSEELQANKA<br>TLVCLISDFYPGAVTVAWKADSSPVKA<br>GVETTTPSKQSNNKYAASSYLSLTPEQ<br>WKSHRSYSCQVTHEGSTVEKTVAPTE<br>CS |
| SEQ ID NO: 20 | DNA Light Chain | GATATCGTCCTGACTCAGCCCCCTAG<br>CGTCAGCGGCGCTCCCGGTCAGAGA<br>GTGACTATTAGCTGTAGCGGCTCTAG<br>CTCTAATATCGGTAATCACTACGTGA<br>ACTGGTATCAGCAGCTGCCCGGCAC<br>CGCCCCTAAGCTGCTGATCTATAGAA<br>ACAATCACCGGCCTAGCGGCGTGCC<br>CGATAGGTTTAGCGGATCTAAGTCAG<br>GCACTAGCGCTAGTCTGGCTATCACC<br>GGACTGCAGTCAGAGGACGAGGCCG<br>ACTACTACTGTCAGTCCTGGGACTAT<br>AGCGGCTTTAGCACCGTGTTCGGCG<br>GAGGCACTAAGCTGACCGTGCTGGG<br>TCAGCCTAAGGCTGCCCCCAGCGTG<br>ACCCTGTTCCCCCCCAGCAGCGAGG<br>AGCTGCAGGCCAACAAGGCCACCCT<br>GGTGTGCCTGATCAGCGACTTCTACC<br>CAGGCGCCGTGACCGTGGCCTGGAA<br>GGCCGACAGCAGCCCCGTGAAGGCC<br>GGCGTGGAGACCACCACCCCCAGCA<br>AGCAGAGCAACAACAAGTACGCCGC<br>CAGCAGCTACCTGAGCCTGACCCCC<br>GAGCAGTGGAAGAGCCACAGGTCCT<br>ACAGCTGCCAGGTGACCCACGAGGG<br>CAGCACCGTGGAAAAGACCGTGGCC<br>CCAACCGAGTGCAGC | mAb2

| SEQ ID NO: 21 (Kabat) | HCDR1 | VYGMN |
| SEQ ID NO: 22 (Kabat) | HCDR2 | IIWYDGDNQYYADSVKG |
| SEQ ID NO: 23 (Kabat) | HCDR3 | DLRTGPFDY |
| SEQ ID NO: 24 (Chothia) | HCDR1 | GFTFSVY |
| SEQ ID NO: 25 (Chothia) | HCDR2 | WYDGDN |
| SEQ ID NO: 26 (Chothia) | HCDR3 | DLRTGPFDY |
| SEQ ID NO: 27 | VH | QVQLVESGGGVVQPGRSLRLSCAASG<br>FTFSVYGMNWVRQAPGKGLEWVAIIW<br>YDGDNQYYADSVKGRFTISRDNSKNTL<br>YLQMNGLRAEDTAVYYCARDLRTGPF<br>DYWGQGTLVTVSS |
| SEQ ID NO: 28 | DNA VH | CAGGTGCAGCTGGTGGAGAGCGGCG<br>GCGGCGTGGTGCAGCCCGGCAGGA<br>GCCTGAGGCTGAGCTGCGCCGCCAG<br>CGGCTTCACCTTCAGCGTGTACGGC<br>ATGAACTGGGTGAGGCAGGCCCCCG<br>GCAAGGGCCTGGAGTGGGTGGCCAT<br>CATCTGGTACGACGGCGACAACCAG<br>TACTACGCCGACAGCGTGAAGGGCA<br>GGTTCACCATCAGCAGGGACAACAG<br>CAAGAACACCCTGTACCTGCAGATGA<br>ACGGCCTGAGGGCCGAGGACACCGC<br>CGTGTACTACTGCGCCAGGGACCTG<br>AGGACCGGCCCCTTCGACTACTGGG<br>GCCAGGGCACCCTGGTGACCGTGAG<br>CAGC |

TABLE 15-continued

Sequences according to embodiments of the invention

| SEQ ID NUMBER | Ab region | Sequence |
| --- | --- | --- |
| SEQ ID NO: 29 | Heavy Chain | QVQLVESGGGVVQPGRSLRLSCAASG<br>FTFSVYGMNWVRQAPGKGLEWVAIIW<br>YDGDNQYYADSVKGRFTISRDNSKNTL<br>YLQMNGLRAEDTAVYYCARDLRTGPF<br>DYWGQGTLVTVSSASTKGPSVFPLAP<br>SSKSTSGGTAALGCLVKDYFPEPVTVS<br>WNSGALTSGVHTFPAVLQSSGLYSLSS<br>VVTVPSSSLGTQTYICNVNHKPSNTKV<br>DKRVEPKSCDKTHTCPPCPAPELLGG<br>PSVFLFPPKPKDTLMISRTPEVTCVVVD<br>VSHEDPEVKFNWYVDGVEVHNAKTKP<br>REEQYNSTYRVVSVLTVLHQDWLNGK<br>EYKCKVSNKALPAPIEKTISKAKGQPRE<br>PQVYTLPPSREEMTKNQVSLTCLVKGF<br>YPSDIAVEWESNGQPENNYKTTPPVLD<br>SDGSFFLYSKLTVDKSRWQQGNVFSC<br>SVMHEALHNHYTQKSLSLSPGK |
| SEQ ID NO: 30 | DNA Heavy Chain | CAGGTGCAGCTGGTGGAGAGCGGCG<br>GCGGCGTGGTGCAGCCCGGCAGGA<br>GCCTGAGGCTG<br>AGCTGCGCCGCCAGCGGCTTCACCT<br>TCAGCGTGTACGGCATGAACTGGGT<br>GAGGCAGGCC<br>CCCGGCAAGGGCCTGGAGTGGGTG<br>GCCATCATCTGGTACGACGGCGACA<br>ACCAGTACTAC<br>GCCGACAGCGTGAAGGGCAGGTTCA<br>CCATCAGCAGGGACAACAGCAAGAA<br>CACCCTGTAC<br>CTGCAGATGAACGGCCTGAGGGCCG<br>AGGACACCGCCGTGTACTACTGCGC<br>CAGGGACCTG<br>AGGACCGGCCCCTTCGACTACTGGG<br>GCCAGGGCACCCTGGTGACCGTGAG<br>CAGCGCCAGC<br>ACCAAGGGCCCCAGCGTGTTCCCCC<br>TGGCCCCCAGCAGCAAGAGCACCAG<br>CGGCGGCACC<br>GCCGCCCTGGGCTGCCTGGTGAAGG<br>ACTACTTCCCCGAGCCCGTGACCGT<br>GAGCTGGAAC<br>AGCGGCGCCCTGACCAGCGGCGTGC<br>ACACCTTCCCCGCCGTGCTGCAGAG<br>CAGCGGCCTG<br>TACAGCCTGAGCAGCGTGGTGACCG<br>TGCCCAGCAGCAGCCTGGGCACCCA<br>GACCTACATC<br>TGCAACGTGAACCACAAGCCCAGCA<br>ACACCAAGGTGGACAAGAGGGTGGA<br>GCCCAAGAGC<br>TGCGACAAGACCCACACCTGCCCCC<br>CCTGCCCCGCCCCCGAGCTGCTGGG<br>CGGCCCCAGC<br>GTGTTCCTGTTCCCCCCCAAGCCCAA<br>GGACACCCTGATGATCAGCAGGACC<br>CCCGAGGTG<br>ACCTGCGTGGTGGTGGACGTGAGCC<br>ACGAGGACCCCGAGGTGAAGTTCAA<br>CTGGTACGTG<br>GACGGCGTGGAGGTGCACAACGCCA<br>AGACCAAGCCCAGGGAGGAGCAGTA<br>CAACAGCACC<br>TACAGGGTGGTGAGCGTGCTGACCG<br>TGCTGCACCAGGACTGGCTGAACGG<br>CAAGGAGTAC<br>AAGTGCAAGGTGAGCAACAAGGCCC<br>TGCCCGCCCCCATCGAGAAGACCAT<br>CAGCAAGGCC<br>AAGGGCCAGCCCAGGGAGCCCCAG<br>GTGTACACCCTGCCCCCCAGCAGGG<br>AGGAGATGACC<br>AAGAACCAGGTGAGCCTGACCTGCC<br>TGGTGAAGGGCTTCTACCCCAGCGA<br>CATCGCCGTG<br>GAGTGGGAGAGCAACGGCCAGCCCG |

TABLE 15-continued

Sequences according to embodiments of the invention

| SEQ ID NUMBER | Ab region | Sequence |
|---|---|---|
| | | AGAACAACTACAAGACCACCCCCCCC GTGCTGGAC AGCGACGGCAGCTTCTTCCTGTACAG CAAGCTGACCGTGGACAAGAGCAGG TGGCAGCAG GGCAACGTGTTCAGCTGCAGCGTGA TGCACGAGGCCCTGCACAACCACTA CACCCAGAAG AGCCTGAGCCTGAGCCCCGGCAAG |
| SEQ ID NO: 31 (Kabat) | LCDR1 | RASQSIGSSLH |
| SEQ ID NO: 32 (Kabat) | LCDR2 | YASQSFS |
| SEQ ID NO: 33 (Kabat) | LCDR3 | HQSSSLPFT |
| SEQ ID NO: 34 (Chothia) | LCDR1 | SQSIGSS |
| SEQ ID NO: 35 (Chothia) | LCDR2 | YAS |
| SEQ ID NO: 36 (Chothia) | LCDR3 | SSSLPF |
| SEQ ID NO: 37 | VL | EIVLTQSPDFQSVTPKEKVTITCRASQS IGSSLHWYQQKPDQSPKLLIKYASQSF SGVPSRFSGSGSGTDFTLTINSLEAED AAAYYCHQSSSLPFTFGPGTKVDIK |
| SEQ ID NO: 38 | DNA VL | GAGATCGTGCTGACCCAGTCACCCG ACTTTCAGTCAGTGACCCCTAAAGAA AAAGTGACTATCACCTGTAGGGCCTC CCAGTCTATCGGCTCTAGCCTGCACT GGTATCAGCAGAAGCCCGATCAGTC ACCTAAGCTGCTGATTAAGTACGCCT CTCAGTCCTTTAGCGGCGTGCCCTCT AGGTTTAGCGGCTCAGGCTCAGGCA CCGACTTCACCCTGACTATCAATAGC CTGGAAGCCGAGGACGCCGCTGCCT ACTACTGTCATCAGTCAAGTAGCCTG CCCTTCACCTTCGGCCCTGGCACTAA AGTGGATATTAAG |
| SEQ ID NO: 39 | Light Chain | EIVLTQSPDFQSVTPKEKVTITCRASQS IGSSLHWYQQKPDQSPKLLIKYASQSF SGVPSRFSGSGSGTDFTLTINSLEAED AAAYYCHQSSSLPFTFGPGTKVDIKRT VAAPSVFIFPPSDEQLKSGTASVVCLLN NFYPREAKVQWKVDNALQSGNSQESV TEQDSKDSTYSLSSTLTLSKADYEKHK VYACEVTHQGLSSPVTKSFNRGEC |
| SEQ ID NO: 40 | DNA Light Chain | GAGATCGTGCTGACCCAGTCACCCG ACTTTCAGTCAGTGACCCCTAAAGAA AAAGTGACTATCACCTGTAGGGCCTC CCAGTCTATCGGCTCTAGCCTGCACT GGTATCAGCAGAAGCCCGATCAGTC ACCTAAGCTGCTGATTAAGTACGCCT CTCAGTCCTTTAGCGGCGTGCCCTCT AGGTTTAGCGGCTCAGGCTCAGGCA CCGACTTCACCCTGACTATCAATAGC CTGGAAGCCGAGGACGCCGCTGCCT ACTACTGTCATCAGTCAAGTAGCCTG CCCTTCACCTTCGGCCCTGGCACTAA AGTGGATATTAAGCGTACGGTGGCC GCTCCCAGCGTGTTCATCTTCCCCCC CAGCGACGAGCAGCTGAAGAGCGGC ACCGCCAGCGTGGTGTGCCTGCTGA ACAACTTCTACCCCCGGGAGGCCAA GGTGCAGTGGAAGGTGGACAACGCC CTGCAGAGCGGCAACAGCCAGGAGA GCGTCACCGAGCAGGACAGCAAGGA CTCCACCTACAGCCTGAGCAGCACC CTGACCCTGAGCAAGGCCGACTACG AGAAGCATAAGGTGTACGCCTGCGA GGTGACCCACCAGGGCCTGTCCAGC CCCGTGACCAAGAGCTTCAACAGGG GCGAGTGC |

TABLE 15-continued

Sequences according to embodiments of the invention

| SEQ ID NUMBER | Ab region | Sequence |
| --- | --- | --- |
| Second part from mAb2 | | |
| SEQ ID NO: 41 (Combined) | HCDR1 | GFTFSVYGMN |
| SEQ ID NO: 42 (Combined) | HCDR2 | IIWYDGDNQYYADSVKG |
| SEQ ID NO: 43 (Combined) | HCDR3 | DLRTGPFDY |
| SEQ ID NO: 44 (Kabat) | HCDR1 | VYGMN |
| SEQ ID NO: 45 (Kabat) | HCDR2 | IIWYDGDNQYYADSVKG |
| SEQ ID NO: 46 (Kabat) | HCDR3 | DLRTGPFDY |
| SEQ ID NO: 47 (Chothia) | HCDR1 | GFTFSVY |
| SEQ ID NO: 48 (Chothia) | HCDR2 | WYDGDN |
| SEQ ID NO: 49 (Chothia) | HCDR3 | DLRTGPFDY |
| SEQ ID NO: 50 (IMGT) | HCDR1 | GFTFSVYG |
| SEQ ID NO: 51 (IMGT) | HCDR2 | IWYDGDNQ |
| SEQ ID NO: 52 (IMGT) | HCDR3 | ARDLRTGPFDY |
| SEQ ID NO: 53 | VH | QVQLVESGGGVVQPGRSLRLSCAASGFTFSVYGMNWVRQAPGKGLEWVAIIWYDGDNQYYADSVKGRFTISRDNSKNTLYLQMNGLRAEDTAVYYCARDLRTGPFDYWGQGTLVTVSS |
| SEQ ID NO: 54 | DNA VH | CAGGTGCAGCTGGTGGAATCAGGCGGCGGAGTGGTGCAGCCTGGTAGATCACTGAGACTGAGCTGCGCTGCTAGTGGCTTCACCTTTAGCGTCTACGGAATGAACTGGGTCCGACAGGCCCCTGGGAAAGGCCTGGAGTGGGTGGCAATTATCTGGTACGACGGCGATAATCAGTACTACGCCGATAGCGTGAAGGGACGGTTCACTATCTCTAGGGATAACTCTAAGAACACCCTGTACCTGCAGATGAACGGCCTGAGAGCCGAGGACACCGCCGTCTACTACTGCGCTAGGGACCTGAGAACCGGCCCCTTCGACTACTGGGGACAGGGCACCCTGGTCACCGTGTCTAGC |
| SEQ ID NO: 55 | Heavy Chain | QVQLVESGGGVVQPGRSLRLSCAASGFTFSVYGMNWVRQAPGKGLEWVAIIWYDGDNQYYADSVKGRFTISRDNSKNTLYLQMNGLRAEDTAVYYCARDLRTGPFDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVCTLPPSREEMTKNQVSLSCAVKGFYPSDIAVEWESNGQPENNYKTTPPVLDSDGSFFLVSKLTVDKSRWQQGNVFSCSVMHEALHNHYTQKSLSLSPGK |
| SEQ ID NO: 56 | DNA Heavy Chain | CAGGTGCAGCTGGTGGAATCAGGCGGCGGAGTGGTGCAGCCTGGTAGATCACTGAGACTGAGCTGCGCTGCTAGTGGCTTCACCTTTAGCGTCTACGGAATGAACTGGGTCCGACAGGCCCCTGGGAAAGGCCTGGAGTGGGTGGCAATTATCTGGTACGACGGCGATAATCAGTACTACGCCGATAGCGTGAAGGGACGGTTCACTATCTCTAGGGATAACTCTAAGAACACCCTGTACCTGCAGATGAACGG |

TABLE 15-continued

Sequences according to embodiments of the invention

| SEQ ID NUMBER | Ab region | Sequence |
|---|---|---|
| | | CCTGAGAGCCGAGGACACCGCCGTC<br>TACTACTGCGCTAGGGACCTGAGAAC<br>CGGCCCCTTCGACTACTGGGGACAG<br>GGCACCCTGGTCACCGTGTCTAGCG<br>CCTCTACTAAGGGCCCAAGCGTGTTC<br>CCCCTGGCCCCTAGCTCTAAGTCTAC<br>TAGCGGAGGCACCGCCGCTCTGGGC<br>TGCCTGGTCAAGGACTACTTCCCCGA<br>GCCCGTGACCGTCAGCTGGAATAGC<br>GGCGCTCTGACTAGCGGAGTGCACA<br>CCTTCCCCGCCGTGCTGCAGTCTAG<br>CGGCCTGTATAGCCTGTCTAGCGTC<br>GTGACCGTGCCTAGCTCTAGCCTGG<br>GCACTCAGACCTATATCTGTAACGTG<br>AACCACAAGCCCTCTAACACTAAGGT<br>GGACAAGCGGGTGGAACCTAAGTCC<br>TGCGATAAGACTCACACCTGTCCTCC<br>CTGCCCTGCCCCTGAGGCTGCCGGA<br>GGACCTAGCGTGTTCCTGTTCCCACC<br>TAAGCCTAAAGACACCCTGATGATCT<br>CTAGGACCCCCGAAGTGACCTGCGT<br>GGTGGTGGACGTCTCACACGAGGAC<br>CCTGAAGTGAAGTTTAATTGGTACGT<br>GGACGGCGTGGAAGTGCACAACGCT<br>AAGACTAAGCCTAGAGAGGAACAGTA<br>TAACTCTACCTATAGGGTCGTCAGCG<br>TGCTGACAGTGCTGCACCAGGACTG<br>GCTGAACGGGAAAGAGTATAAGTGTA<br>AAGTGTCTAACAAGGCCCTGCCAGC<br>CCCTATCGAAAAGACTATCTCTAAGG<br>CTAAGGGGCAGCCTAGAGAACCCCA<br>AGTGTGCACTCTGCCCCCTAGTAGAG<br>AAGAGATGACTAAGAATCAGGTGTCA<br>CTGAGCTGTGCCGTGAAGGGCTTCT<br>ACCCTAGCGATATCGCCGTGGAGTG<br>GGAGAGCAACGGCCAGCCCGAGAAC<br>AACTACAAGACCACCCCCCAGTGCT<br>GGACAGCGACGGCAGCTTCTTCCTG<br>GTGAGCAAGCTGACCGTGGACAAGT<br>CCAGGTGGCAGCAGGGCAACGTGTT<br>CAGCTGCAGCGTGATGCACGAGGCC<br>CTGCACAACCACTACACCCAGAAGTC<br>CCTGAGCCTGAGCCCCGGCAAG |
| SEQ ID NO: 57 (Combined) | LCDR1 | RASQSIGSSLH |
| SEQ ID NO: 58 (Combined) | LCDR2 | YASQSFS |
| SEQ ID NO: 59 (Combined) | LCDR3 | HQSSSLPFT |
| SEQ ID NO: 60 (Kabat) | LCDR1 | RASQSIGSSLH |
| SEQ ID NO: 61 (Kabat) | LCDR2 | YASQSFS |
| SEQ ID NO: 62 (Kabat) | LCDR3 | HQSSSLPFT |
| SEQ ID NO: 63 (Chothia) | LCDR1 | SQSIGSS |
| SEQ ID NO: 64 (Chothia) | LCDR2 | YAS |
| SEQ ID NO: 65 (Chothia) | LCDR3 | SSSLPF |
| SEQ ID NO: 66 (IMGT) | LCDR1 | QSIGSS |
| SEQ ID NO: 67 (IMGT) | LCDR2 | YASQSFSGVP |
| SEQ ID NO: 68 (IMGT) | LCDR3 | HQSSSLPFT |
| SEQ ID NO: 69 | VL | EIVLTQSPDFQSVTPKEKVTITCRASQS<br>IGSSLHWYQQKPDQSPKLLIKYASQSF<br>SGVPSRFSGSGSGTDFTLTINSLEAED<br>AAAYYCHQSSSLPFTFGPGTKVDIK |
| SEQ ID NO: 70 | DNA VL | GAGATCGTGCTGACCCAGTCACCCG<br>ACTTTCAGTCAGTGACCCCTAAAGAA<br>AAAGTGACTATCACCTGTAGGGCCTC |

TABLE 15-continued

Sequences according to embodiments of the invention

| SEQ ID NUMBER | Ab region | Sequence |
|---|---|---|
| | | CCAGTCTATCGGCTCTAGCCTGCACT<br>GGTATCAGCAGAAGCCCGATCAGTC<br>ACCTAAGCTGCTGATTAAGTACGCCT<br>CTCAGTCCTTTAGCGGCGTGCCCTCT<br>AGGTTTAGCGGCTCAGGCTCAGGCA<br>CCGACTTCACCCTGACTATCAATAGC<br>CTGGAAGCCGAGGACGCCGCTGCCT<br>ACTACTGTCATCAGTCAAGTAGCCTG<br>CCCTTCACCTTCGGCCCTGGCACTAA<br>AGTGGATATTAAG |
| SEQ ID NO: 71 | Light Chain | EIVLTQSPDFQSVTPKEKVTITCRASQS<br>IGSSLHWYQQKPDQSPKLLIKYASQSF<br>SGVPSRFSGSGSGTDFTLTINSLEAED<br>AAAYYCHQSSSLPFTFGPGTKVDIKRT<br>VAAPSVFIFPPSDEQLKSGTASVVCLLN<br>NFYPREAKVQWKVDNALQSGNSQESV<br>TEQDSKDSTYSLSSTLTLSKADYEKHK<br>VYACEVTHQGLSSPVTKSFNRGEC |
| SEQ ID NO: 72 | DNA Light Chain | GAGATCGTGCTGACCCAGTCACCCG<br>ACTTTCAGTCAGTGACCCCTAAAGAA<br>AAAGTGACTATCACCTGTAGGGCCTC<br>CCAGTCTATCGGCTCTAGCCTGCACT<br>GGTATCAGCAGAAGCCCGATCAGTC<br>ACCTAAGCTGCTGATTAAGTACGCCT<br>CTCAGTCCTTTAGCGGCGTGCCCTCT<br>AGGTTTAGCGGCTCAGGCTCAGGCA<br>CCGACTTCACCCTGACTATCAATAGC<br>CTGGAAGCCGAGGACGCCGCTGCCT<br>ACTACTGTCATCAGTCAAGTAGCCTG<br>CCCTTCACCTTCGGCCCTGGCACTAA<br>AGTGGATATTAAGCGTACGGTGGCC<br>GCTCCCAGCGTGTTCATCTTCCCCCC<br>CAGCGACGAGCAGCTGAAGAGCGGC<br>ACCGCCAGCGTGGTGTGCCTGCTGA<br>ACAACTTCTACCCCCGGGAGGCCAA<br>GGTGCAGTGGAAGGTGGACAACGCC<br>CTGCAGAGCGGCAACAGCCAGGAGA<br>GCGTCACCGAGCAGGACAGCAAGGA<br>CTCCACCTACAGCCTGAGCAGCACC<br>CTGACCCTGAGCAAGGCCGACTACG<br>AGAAGCATAAGGTGTACGCCTGCGA<br>GGTGACCCACCAGGGCCTGTCCAGC<br>CCCGTGACCAAGAGCTTCAACAGGG<br>GCGAGTGC |

First part from mAb1

| SEQ ID NO: 73 (Combined) | HCDR1 | GGTFKSYAIS |
| SEQ ID NO: 74 (Combined) | HCDR2 | NIIPMTGQTYYAQKFQG |
| SEQ ID NO: 75 (Combined) | HCDR3 | AAYHPLVFDN |
| SEQ ID NO: 76 (Kabat) | HCDR1 | SYAIS |
| SEQ ID NO: 77 (Kabat) | HCDR2 | NIIPMTGQTYYAQKFQG |
| SEQ ID NO: 78 (Kabat) | HCDR3 | AAYHPLVFDN |
| SEQ ID NO: 79 (Chothia) | HCDR1 | GGTFKSY |
| SEQ ID NO: 80 (Chothia) | HCDR2 | IPMTGQ |
| SEQ ID NO: 81 (Chothia) | HCDR3 | AAYHPLVFDN |
| SEQ ID NO: 82 (IMGT) | HCDR1 | GGTFKSYA |
| SEQ ID NO: 83 (IMGT) | HCDR2 | IIPMTGQT |
| SEQ ID NO: 84 (IMGT) | HCDR3 | ARAAYHPLVFDN |
| SEQ ID NO: 85 | VH | EVQLVQSGAEVKKPGSSVKVSCKASG<br>GTFKSYAISWVRQAPGQGLEWMGNIIP<br>MTGQTYYAQKFQGRVTITADESTSTAY |

TABLE 15-continued

Sequences according to embodiments of the invention

| SEQ ID NUMBER | Ab region | Sequence |
| --- | --- | --- |
| | | MELSSLRSEDTAVYYCARAAYHPLVFD<br>NWGQGTLVTVSS |
| SEQ ID NO: 86 | DNA VH | GAGGTGCAGCTGGTGCAGTCAGGCG<br>CCGAAGTGAAGAAACCCGGCTCTAG<br>CGTGAAAGTCAGCTGTAAAGCTAGTG<br>GCGGCACCTTCAAGTCCTACGCTATT<br>AGCTGGGTCAGACAGGCCCCAGGTC<br>AGGGCCTGGAGTGGATGGGCAATAT<br>TATCCCTATGACCGGTCAGACCTACT<br>ACGCTCAGAAATTTCAGGGTAGAGTG<br>ACTATCACCGCCGACGAGTCTACTAG<br>CACCGCCTATATGGAACTGTCTAGCC<br>TGAGATCAGAGGACACCGCCGTCTA<br>CTACTGCGCTAGAGCCGCCTATCACC<br>CCCTGGTGTTCGATAACTGGGGTCA<br>GGGCACCCTGGTCACCGTGTCTAGC |
| SEQ ID NO: 87 | Heavy Chain | EVQLVQSGAEVKKPGSSVKVSCKASG<br>GTFKSYAISWVRQAPGQGLEWMGNIIP<br>MTGQTYYAQKFQGRVTITADESTSTAY<br>MELSSLRSEDTAVYYCARAAYHPLVFD<br>NWGQGTLVTVSSASTKGPSVFPLAPS<br>SKSTSGGTAALGCLVKDYFPEPVTVS<br>WNSGALTSGVHTFPAVLQSSGLYSLSS<br>VVTVPSSSLGTQTYICNVNHKPSNTKV<br>DKRVEPKSCDKTHTCPPCPAPEAAGG<br>PSVFLFPPKPKDTLMISRTPEVTCVVVD<br>VSHEDPEVKFNWYVDGVEVHNAKTKP<br>REEQYNSTYRVVSVLTVLHQDWLNGK<br>EYKCKVSNKALPAPIEKTISKAKGQPRE<br>PQVYTLPPCREEMTKNQVSLWCLVKG<br>FYPSDIAVEWESNGQPENNYKTTPPVL<br>DSDGSFFLYSKLTVDKSRWQQGNVFS<br>CSVMHEALHNHYTQKSLSLSPGK |
| SEQ ID NO: 88 | DNA Heavy Chain | GAGGTGCAGCTGGTGCAGTCAGGCG<br>CCGAAGTGAAGAAACCCGGCTCTAG<br>CGTGAAAGTCAGCTGTAAAGCTAGTG<br>GCGGCACCTTCAAGTCCTACGCTATT<br>AGCTGGGTCAGACAGGCCCCAGGTC<br>AGGGCCTGGAGTGGATGGGCAATAT<br>TATCCCTATGACCGGTCAGACCTACT<br>ACGCTCAGAAATTTCAGGGTAGAGTG<br>ACTATCACCGCCGACGAGTCTACTAG<br>CACCGCCTATATGGAACTGTCTAGCC<br>TGAGATCAGAGGACACCGCCGTCTA<br>CTACTGCGCTAGAGCCGCCTATCACC<br>CCCTGGTGTTCGATAACTGGGGTCA<br>GGGCACCCTGGTCACCGTGTCTAGC<br>GCTAGCACTAAGGGCCCCTCAGTGTT<br>CCCCCTGGCCCCTAGCTCTAAGTCTA<br>CTAGCGGCGGCACCGCCGCTCTGGG<br>CTGCCTGGTGAAAGACTACTTCCCCG<br>AGCCCGTGACCGTGTCATGGAATAG<br>CGGCGCTCTGACTAGCGGAGTGCAC<br>ACCTTCCCCGCCGTGCTGCAGTCTA<br>GCGGCCTGTATAGCCTGTCTAGCGT<br>GGTGACCGTGCCTAGCTCTAGCCTG<br>GGCACTCAGACCTACATCTGTAACGT<br>GAACCACAAGCCCTCTAACACTAAGG<br>TGGACAAGCGGGTGGAACCTAAGTC<br>CTGCGATAAGACTCACACCTGTCCCC<br>CCTGCCCTGCCCCTGAGGCTGCCGG<br>AGGACCTAGCGTGTTCCTGTTCCCAC<br>CTAAGCCTAAGGACACCCTGATGATC<br>TCTAGGACCCCCGAAGTGACCTGCG<br>TGGTGGTGGATGTGTCTCACGAGGA<br>CCCTGAAGTGAAGTTCAATTGGTACG<br>TGGACGGCGTGGAAGTGCACAACGC<br>TAAGACTAAGCCTAGAGAGGAACAGT<br>ATAACTCCACCTATAGAGTGGTGTCA<br>GTGCTGACCGTGCTGCATCAGGACT<br>GGCTGAACGGCAAAGAGTATAAGTGT<br>AAAGTCTCTAACAAGGCCCTGCCAGC<br>CCCTATCGAAAAGACTATCTCTAAGG |

TABLE 15-continued

Sequences according to embodiments of the invention

| SEQ ID NUMBER | Ab region | Sequence |
|---|---|---|
| | | CTAAGGGCCAGCCTAGAGAACCTCA<br>GGTGTACACCCTGCCCCCCTGTAGA<br>GAAGAGATGACTAAGAATCAGGTGTC<br>CCTGTGGTGTCTGGTGAAAGGCTTCT<br>ACCCTAGCGATATCGCCGTGGAATG<br>GGAGTCTAACGGCCAGCCCGAGAAC<br>AACTATAAGACTACCCCCCTGTGCT<br>GGATAGCGACGGCTCATTCTTCCTGT<br>ACTCTAAGCTGACCGTGGACAAGTCT<br>AGGTGGCAGCAGGGCAATGTGTTTA<br>GCTGTAGCGTGATGCACGAGGCCCT<br>GCATAATCACTACACTCAGAAGTCAC<br>TGAGCCTGAGCCCCGGCAAG |
| SEQ ID NO: 89 (Combined) | LCDR1 | SGSSSNIGNHYVN |
| SEQ ID NO: 90 (Combined) | LCDR2 | RNNHRPS |
| SEQ ID NO: 91 (Combined) | LCDR3 | QSWDYSGFSTV |
| SEQ ID NO: 92 (Kabat) | LCDR1 | SGSSSNIGNHYVN |
| SEQ ID NO: 93 (Kabat) | LCDR2 | RNNHRPS |
| SEQ ID NO: 94 (Kabat) | LCDR3 | QSWDYSGFSTV |
| SEQ ID NO: 95 (Chothia) | LCDR1 | SSSNIGNHY |
| SEQ ID NO: 96 (Chothia) | LCDR2 | RNN |
| SEQ ID NO: 97 (Chothia) | LCDR3 | WDYSGFST |
| SEQ ID NO: 98 (IMGT) | LCDR1 | SSNIGNHY |
| SEQ ID NO: 99 (IMGT) | LCDR2 | RNN |
| SEQ ID NO: 100 (IMGT) | LCDR3 | QSWDYSGFSTV |
| SEQ ID NO: 101 | VL | DIVLTQPPSVSGAPGQRVTISCSGSSS<br>NIGNHYVNWYQQLPGTAPKLLIYRNNH<br>RPSGVPDRFSGSKSGTSASLAITGLQS<br>EDEADYYCQSWDYSGFSTVFGGGTKL<br>TVL |
| SEQ ID NO: 102 | DNA VL | GATATCGTCCTGACTCAGCCCCCTAG<br>CGTCAGCGGCGCTCCCGGTCAGAGA<br>GTGACTATTAGCTGTAGCGGCTCTAG<br>CTCTAATATCGGTAATCACTACGTGA<br>ACTGGTATCAGCAGCTGCCCGGCAC<br>CGCCCCTAAGCTGCTGATCTATAGAA<br>ACAATCACCGGCCTAGCGGCGTGCC<br>CGATAGGTTTAGCGGATCTAAGTCAG<br>GCACTAGCGCTAGTCTGGCTATCACC<br>GGACTGCAGTCAGAGGACGAGGCCG<br>ACTACTACTGTCAGTCCTGGGACTAT<br>AGCGGCTTTAGCACCGTGTTCGGCG<br>GAGGCACTAAGCTGACCGTGCTG |
| SEQ ID NO: 103 | Light Chain | DIVLTQPPSVSGAPGQRVTISCSGSSS<br>NIGNHYVNWYQQLPGTAPKLLIYRNNH<br>RPSGVPDRFSGSKSGTSASLAITGLQS<br>EDEADYYCQSWDYSGFSTVFGGGTKL<br>TVLGQPKAAPSVTLFPPSSEELQANKA<br>TLVCLISDFYPGAVTVAWKADSSPVKA<br>GVETTTPSKQSNNKYAASSYLSLTPEQ<br>WKSHRSYSCQVTHEGSTVEKTVAPTE<br>CS |
| SEQ ID NO: 104 | DNA Light Chain | GATATCGTCCTGACTCAGCCCCCTAG<br>CGTCAGCGGCGCTCCCGGTCAGAGA<br>GTGACTATTAGCTGTAGCGGCTCTAG<br>CTCTAATATCGGTAATCACTACGTGA<br>ACTGGTATCAGCAGCTGCCCGGCAC<br>CGCCCCTAAGCTGCTGATCTATAGAA<br>ACAATCACCGGCCTAGCGGCGTGCC<br>CGATAGGTTTAGCGGATCTAAGTCAG |

TABLE 15-continued

Sequences according to embodiments of the invention

| SEQ ID NUMBER | Ab region | Sequence |
|---|---|---|
| | | GCACTAGCGCTAGTCTGGCTATCACC |
| | | GGACTGCAGTCAGAGGACGAGGCCG |
| | | ACTACTACTGTCAGTCCTGGGACTAT |
| | | AGCGGCTTTAGCACCGTGTTCGGCG |
| | | GAGGCACTAAGCTGACCGTGCTGGG |
| | | TCAGCCTAAGGCTGCCCCCAGCGTG |
| | | ACCCTGTTCCCCCCCAGCAGCGAGG |
| | | AGCTGCAGGCCAACAAGGCCACCCT |
| | | GGTGTGCCTGATCAGCGACTTCTACC |
| | | CAGGCGCCGTGACCGTGGCCTGGAA |
| | | GGCCGACAGCAGCCCCGTGAAGGCC |
| | | GGCGTGGAGACCACCACCCCCAGCA |
| | | AGCAGAGCAACAACAAGTACGCCGC |
| | | CAGCAGCTACCTGAGCCTGACCCCC |
| | | GAGCAGTGGAAGAGCCACAGGTCCT |
| | | ACAGCTGCCAGGTGACCCACGAGGG |
| | | CAGCACCGTGGAAAAGACCGTGGCC |
| | | CCAACCGAGTGCAGC |

Throughout the text of this application, should there be a discrepancy between the text of the specification (e.g. Table 15) and the sequence listing, the text of the specification shall prevail.

---

The invention claimed is:

1. A bispecific antibody, wherein the bispecific antibody binds to IL-18 and IL-1β and comprises:
   a first immunoglobulin heavy chain comprising the amino acid sequence SEQ ID NO. 87;
   a first immunoglobulin light chain comprising the amino acid sequence SEQ ID NO. 103;
   a second immunoglobulin heavy chain comprising the amino acid sequence SEQ ID NO. 55; and
   a second immunoglobulin light chain comprising the amino acid sequence SEQ ID No. 71.

2. A pharmaceutical composition comprising the bispecific antibody according to claim 1 and a pharmaceutically acceptable carrier.

3. A method of treating an inflammasome related disorder comprising administering to a subject afflicted with an inflammasome related disorder an effective amount of a bispecific antibody according to claim 1.

4. The method of claim 3, wherein the inflammasome related disorder is sickle cell disease, vasculopathy, ischemia-reperfusion injury, cardiovascular disease, peripheral artery disease, atherosclerosis, vascular dysfunction, skeletal muscle ischemia, pulmonary sarcoidosis, fibrosis, malaria, hemodialysis-dependent chronic kidney disease, or Crohn's disease.

* * * * *